United States Patent [19]
Stevens et al.

[11] Patent Number: 5,829,447
[45] Date of Patent: Nov. 3, 1998

[54] METHOD AND APPARATUS FOR THORACOSCOPIC INTRACARDIAC PROCEDURES

[75] Inventors: John H. Stevens, Palo Alto; Bruce A. Reitz, Stanford, both of Calif.

[73] Assignee: Heartport, Inc., Redwood City, Calif.

[21] Appl. No.: 646,425

[22] Filed: May 7, 1996

Related U.S. Application Data

[60] Division of Ser. No. 425,179, Apr. 20, 1995, which is a continuation-in-part of Ser. No. 163,241, Dec. 6, 1993, Pat. No. 5,571,215, which is a continuation-in-part of Ser. No. 23,778, Feb. 22, 1993, Pat. No. 5,452,733.

[51] Int. Cl.$^6$ ........................................... A61M 9/00
[52] U.S. Cl. ........................... 128/898; 600/374; 607/122
[58] Field of Search ........................... 606/21, 29, 31, 606/41, 42, 47; 600/372, 374, 393; 607/101, 122; 128/898, 899

[56] References Cited

U.S. PATENT DOCUMENTS

| | | |
|---|---|---|
| 3,124,136 | 3/1964 | Usher . |
| 3,874,388 | 4/1975 | King et al. . |
| 4,007,743 | 2/1977 | Blake . |
| 4,061,135 | 12/1977 | Widran et al. . |
| 4,345,600 | 8/1982 | Rothfuss . |
| 4,573,473 | 3/1986 | Hess . |

(List continued on next page.)

FOREIGN PATENT DOCUMENTS

| | | |
|---|---|---|
| 1045304 | 1/1979 | Canada . |
| 0 573 273 A3 | 6/1993 | European Pat. Off. . |
| 42 22 291 C1 | 7/1992 | Germany . |
| WO 93/10714 | 6/1993 | WIPO . |
| WO 93/13712 | 7/1993 | WIPO . |
| WO 94/13211 | 6/1994 | WIPO . |
| WO 95/01190 | 1/1995 | WIPO . |
| WO 95 30374 | 11/1995 | WIPO . |

OTHER PUBLICATIONS

Mack, et al, "Present Role of Thoracoscopy in the Diagnosis and Treatment of Diseases of the Chest", Ann Thoracic Surgery, Feb. 1992, pp. 403–409.

Boutin et al. "Echocardiographic Follow–up of Atrial Septal Defect After Catheter Closure by Double–Umbrella Device" Circulation 88:621–627 (1993).

Burke et al. "Surgery for congenital heart disease" J. Thorac Cardiovasc Surg 109(3):499–508 (1995).

(List continued on next page.)

*Primary Examiner*—David Isabella
*Attorney, Agent, or Firm*—Jeffry J. Grainger; Jens E. Hoekendijk

[57] ABSTRACT

Devices, systems, and methods are provided for accessing the interior of the heart and performing procedures therein while the heart is beating. In one embodiment, a tubular access device having an inner lumen is provided for positioning through a penetration in a muscular wall of the heart, the access device having a means for sealing within the penetration to inhibit leakage of blood through the penetration. The sealing means may comprise a balloon or flange on the access device, or a suture placed in the heart wall to gather the heart tissue against the access device. An obturator is removably positionable in the inner lumen of the access device, the obturator having a cutting means at its distal end for penetrating the muscular wall of the heart. The access device is preferably positioned through an intercostal space and through the muscular wall of the heart. Elongated instruments may be introduced through the tubular access device into an interior chamber of the heart to perform procedures such as septal defect repair and electrophysiological mapping and ablation. A method of septal defect repair includes positioning a tubular access device percutaneously through an intercostal space and through a penetration in a muscular wall of the heart, passing one or more instruments through an inner lumen of the tubular access device into an interior chamber of the heart, and using the instruments to close the septal defect. Devices and methods for closing the septal defect with either sutures or with patch-type devices are disclosed.

14 Claims, 34 Drawing Sheets

U.S. PATENT DOCUMENTS

| | | |
|---|---|---|
| 4,598,698 | 7/1986 | Siegmund . |
| 4,605,002 | 8/1986 | Rebuffat . |
| 4,621,638 | 11/1986 | Silvestrini . |
| 4,628,937 | 12/1986 | Hess et al. . |
| 4,665,906 | 5/1987 | Jervis . |
| 4,779,611 | 10/1988 | Grooters et al. . |
| 4,786,155 | 11/1988 | Fantone et al. . |
| 4,822,345 | 4/1989 | Danforth . |
| 4,836,204 | 6/1989 | Landymore et al. . |
| 4,901,721 | 2/1990 | Hakki . |
| 4,915,107 | 4/1990 | Rebuffat et al. . |
| 4,917,089 | 4/1990 | Sideris . |
| 4,960,424 | 10/1990 | Grooters . |
| 5,029,574 | 7/1991 | Shimamura et al. . |
| 5,053,046 | 10/1991 | Janese . |
| 5,067,957 | 11/1991 | Jervis . |
| 5,108,420 | 4/1992 | Marks . |
| 5,122,122 | 6/1992 | Allgood ............................... 604/174 |
| 5,147,374 | 9/1992 | Fernandez . |
| 5,178,133 | 1/1993 | Pena . |
| 5,183,464 | 2/1993 | Dubrul et al. . |
| 5,188,636 | 2/1993 | Fedotov . |
| 5,192,301 | 3/1993 | Kamiya et al. . |
| 5,209,747 | 5/1993 | Knoepfler . |
| 5,242,457 | 9/1993 | Akopov et al. . |
| 5,275,166 | 1/1994 | Vaitekunas et al. . |
| 5,284,488 | 2/1994 | Sideris . |
| 5,293,869 | 3/1994 | Edwards et al. . |
| 5,309,896 | 5/1994 | Moll et al. . |
| 5,309,910 | 5/1994 | Edwards et al. . |
| 5,312,341 | 5/1994 | Turi . |
| 5,313,943 | 5/1994 | Houser et al. . |
| 5,314,466 | 5/1994 | Stern et al. . |
| 5,318,525 | 6/1994 | West et al. . |
| 5,328,467 | 7/1994 | Edwards et al. . |
| 5,329,927 | 7/1994 | Gardineer et al. . |
| 5,330,492 | 7/1994 | Haugen . |
| 5,334,210 | 8/1994 | Gainturco . |
| 5,334,217 | 8/1994 | Das . |
| 5,336,182 | 8/1994 | Lundquist et al. . |
| 5,338,317 | 8/1994 | Hasson et al. . |
| 5,345,937 | 9/1994 | Middleman et al. . |
| 5,346,459 | 9/1994 | Allen . |
| 5,353,783 | 10/1994 | Nakao et al. . |
| 5,358,478 | 10/1994 | Thompson et al. . |
| 5,358,488 | 10/1994 | Suriyapa . |
| 5,361,752 | 11/1994 | Moll et al. . |
| 5,363,861 | 11/1994 | Edwards et al. . |
| 5,364,351 | 11/1994 | Heinzelman et al. . |
| 5,368,592 | 11/1994 | Stern et al. . |
| 5,380,291 | 1/1995 | Kaali . |
| 5,381,794 | 1/1995 | Tei et al. . |
| 5,381,795 | 1/1995 | Nordgren et al. . |
| 5,383,466 | 1/1995 | Partika . |
| 5,383,888 | 1/1995 | Zvenyatsky et al. . |
| 5,386,817 | 2/1995 | Jones . |
| 5,391,156 | 2/1995 | Hildwein et al. . |
| 5,397,331 | 3/1995 | Himpens et al. . |
| 5,400,770 | 3/1995 | Nakao et al. . |
| 5,402,772 | 4/1995 | Moll et al. . |
| 5,403,328 | 4/1995 | Shallman . |
| 5,403,329 | 4/1995 | Hinchcliffe . |
| 5,405,360 | 4/1995 | Tovey . |
| 5,409,483 | 4/1995 | Campbell et al. . |
| 5,411,481 | 5/1995 | Allen et al. . |
| 5,421,323 | 6/1995 | Hermann et al. . |
| 5,425,357 | 6/1995 | Moll et al. . |
| 5,425,737 | 6/1995 | Burbank et al. . |
| 5,425,744 | 6/1995 | Fagan et al. . |
| 5,425,747 | 6/1995 | Brotz . |
| 5,433,727 | 7/1995 | Sideris . |
| 5,450,843 | 9/1995 | Moll et al. . |
| 5,451,235 | 9/1995 | Lock et al. . |
| 5,486,193 | 1/1996 | Bourne et al. . |
| 5,507,811 | 4/1996 | Koike et al. . |
| 5,564,440 | 10/1996 | Swartz et al. . |

OTHER PUBLICATIONS

Cox et al. "The surgical treatment of atrial fibrillation I. Summary of the current concepts of the mechanisms of atrial flutter and atrial fibrillation" J. Thorac Cardiovasc Surg 101(3):402–405 (1991).

Cox et al. "The surgical treatment of atrial fibrillation II. Intraoperative electrophysiologic mapping and description of the electrophysiologic basis of atrial flutter and atrial fibrillation." J Thorac Cardiovasc Surg 101(3):406–426 (1991).

Cox et al. "The surgical treatment of atrial fibrillation III. Development of a definitive surgical procedure." J Thorac Cardiovasc Surg 103(4):569–583 (1991).

Cox et al. "The surgical treatment of atrial fibrillation IV. Surgical technique." J Thorac Cardiovasc Surg 101(4):584–592 (1991).

Cox et al. "Five–year experience with the Maze procedure for atrial fibrillation" Ann Thorac Surg 56:814–824 (1993).

Das et al. "Experimental atrial septal closure with a new, transcatheter, self–centering device" Circulation 88[part 1]:1754–1765 (1993).

Fishberger et al. "Intraoperative Device Closure of Ventricular Septal Defects" Circulation 88[part 2]:205–209 (1993).

Ganz et al. "Supraventricular Tachycardia" New England J of Med 332(3):162–173 (1995).

Gray et al. "Clinical outcomes and costs of transcatheter as compared with surgical closure of patent ductus arteriosus" 329(21):1517–1523 (1993).

Guffi et al. "Surgical closure of the patent ductus arteriosus with an intravascular prosthesis: Clinical experience" J. Card Surg 9:343–347 (1994).

Hickey et al. "Transscatheter closure of atrial septal defects: Hemodynamic complications and anesthetic management" Anesth Analg 74:44–50 (1992).

Khan et al. "Blade atrial septostomy: Experience with the first 50 procedures" Catheterization and Cardiovasc Diagn 23:257–262 (1991).

Khan et al. "Experience with 205 procedures of transcatheter closure of ductus arteriosus in 182 patients, with special reference to residual shunts and long–term follow–up." J. Thorac and Cardiovasc Surg. 104(6):1721–1727 (1992).

Lock et al. "Transcatheter umbrella closure of congenital heart defects" Circulation 75(3):593–599 (1987).

Lock et al. "Transcatheter closure of atrial septal defects—Experimental studies" Circulation 79:1091–1099 (1989).

Lloyd et al. "Atrial sepal defect occlusion with the buttoned device (a multi–institutional U.S. trial)" Am J Cardiol 73:286–291 (1994).

Mandell et al. "Devices for transcatheter closure of intracardiac defects" AJR 160:179–184 (1993).

Mills et al. "Umbrella catheter for nonoperative closure of atrial septal defects" Medical Instrumentation 12(1):65–69 (1978).

Minich et al. "Echocardiographic guidance during placement of the buttoned double–disk device for atrial septal defect closure" Echocardiography 10(6):567–572 (1993).

Mills et al. "Nonoperative closure of left–to–right shunts" J. Thorac Cardiovasc Surg 72(3):371–378 (1976).

Nykanen et al. "Transcatheter pataent ductus arteriosus occlusion: Application in the small child" J Am Coll Cardiol 23(7):1666–1670 (1994).

Park et al. "Clinical use of blade atrial septostomy" Circulation 58(4):600–606 (1978).

Pavcnik et al. "Monodisk: Device for percutaneous transcatheter closure of cardiac septal defects" Cardiovasc Intervent Radiol 16:308–312 (1993).

Rao et al. "Role of buttoned double–disc device in the management of atrial septal defects" Am Heart J 123(1):191–200 (1992).

Rao et al. "Relationship of echocardiographic, shunt flow, and angiographic size to the stretched diameter of the atrial septal defect" Am Heart J 122:505–508 (1991).

Rao et al. "Echocardiographic estimation of balloon–stretched diameter of secundum atrial septal defect for transcatheter occlusion" Am Heart J 124:172–175 (1992).

Rao et al. "Transcatheter closure of atrial septal defect by Buttoned devices" Am J Cardiol 69:1056–1061 (1992).

Redington et al. "Novel uses of the Rashkind ductal umbrella in adults and children with congenital heart disease" Br Heart J 69:47–51 (1993).

Williamson et al. "Radiofrequency catheter modification of atrioventricular conduction to control the ventricular rate during atrial fibrillatioln" New Engl J Med 331(14):910–917 (1994).

Tynan et al. "Transcatheter occlusioln of persistent arterial duct" The Lancet 340:1062–1066 (1992).

Archives of Surgery 9(3)[part II]:689–821 (1924).

van der Velde et al. "Transesophageal echocardiographic guidance of transcatheter ventricular septal defect closure" JACC 23(7):1660–1665 (1994).

Nykanen et al. "Transcatheter patent ductus arteriosus occlusion: Application in the small child" JACC 23(7):1666–1670 (1994).

Friedman et al. "Successful Closure of a previously unsuspected atrial septal defect by an implantable Clamshell™ Device and subsequent transvenous pacemaker implantation." Texas Heart J 21:11–6 (1994).

Grifka et al. "New Gianturco–Grifka Vascular Occlusion Device. Initial Studies in a Canine Model.", Circulation 91:1840–1846 (1995).

Pozza et al. "Transcatheter Occlusion of Patent Ductus Arteriosus Using a Newly Developed Self–Expanding Device. Evaluation in a Canine Model" Investigative Radiology. 30(2):104–109 (1995).

Latson et al. "Endocarditis Risk of the USCI PDA Umbrella for Transcatheter Closure of Patent Ductus Arteriosus", Circulation, 90:2525–2528 (1994).

Rosenfeld et al. "Echocardiographic Predictors of Candidacy for Successful Transcatheter Atrial Septal Defect Closure", Catheterization and Cardiovasc Diagnosis, 34:29–34 (1995).

Rigby et al. "Primary transcatheter umbrella closure of perimembranous ventricular septal defect", Br Heart J. 72:368–371 (1994).

Gray et al. "Examination of the early 'learning curve' for transcatheter closure of patent ductus arteriosus using the Rashkind occuluder", Circulation, 90:II–36–II–42 (1994).

Laussen et al. "Transcatheter closure of ventricular septal defects: Hemodynamic instability and anesthetic management", Anesth Analg, 80:1076–82 (1995).

Reddy et al. "Echocardiographic predictors of success of catheter closure of atrial septal defect with the buttoned device", Am Heart J, 129:76–82 (1995).

Rao et al. "International experience with secundum atrial septal defect occlusion by the buttoned device", Am Heart J, 128(5):1022–1035, (1994).

Galal et al. "Peri–operative complications following surgical closure of atrial septal defect type II in 232 patients—a baseline study.", European Heart J. 15:1381–1384 (1994).

Pearl et al. "Spontaneous Closure of Fenestrations in an Inteatrial Gore–Tex Patch: Application to the Fontan Procedure", Ann Thorac Surg. 57:611–4 (1994).

Mack et al., "Present Role of Thoracoscopy in the Diagnosis and Treatment of Diseases of the Chest," *The Society of Thoracic Surgeons,* 1992, pp. 403–409.

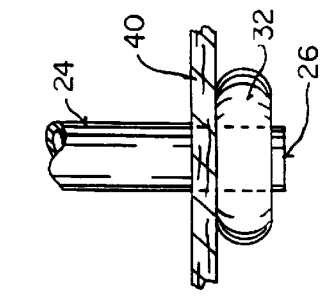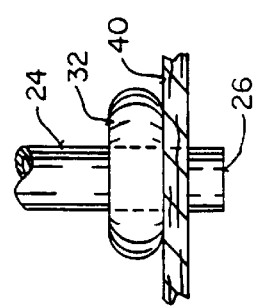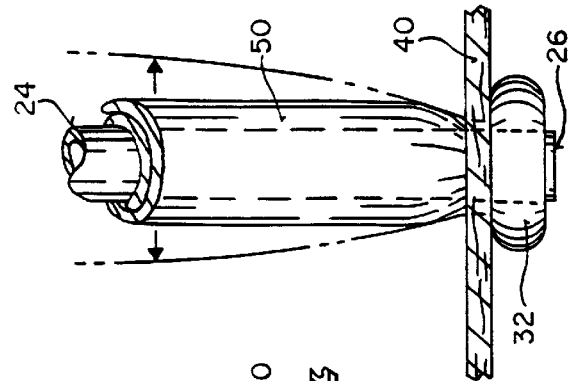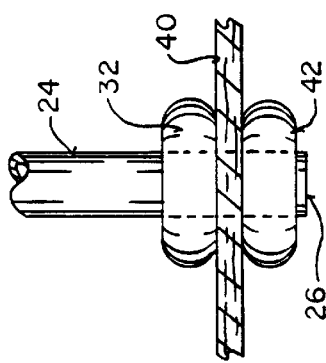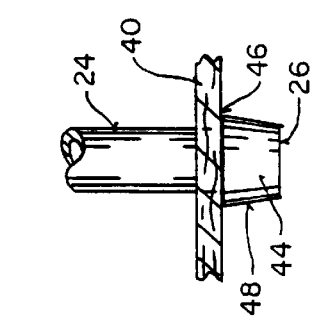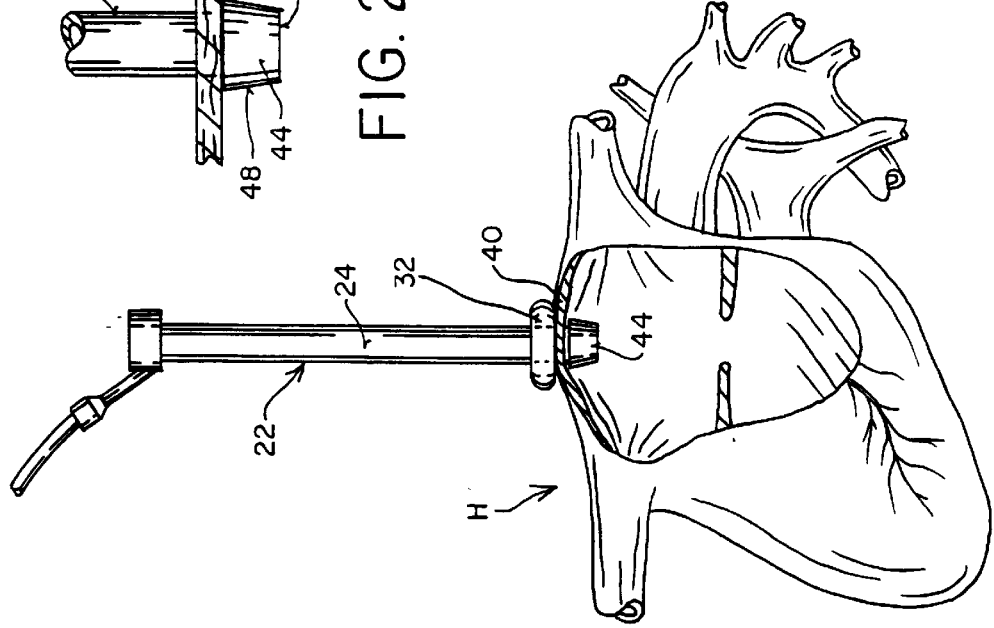

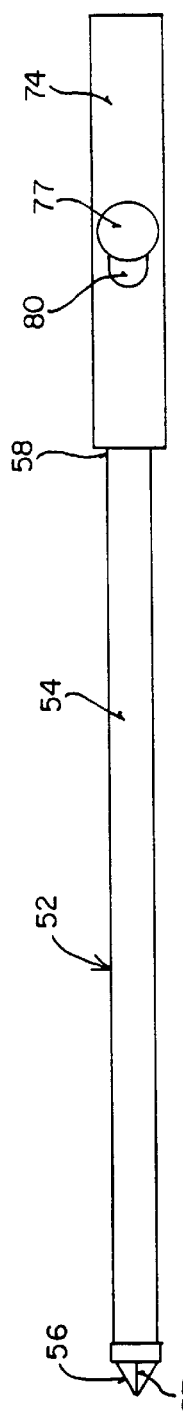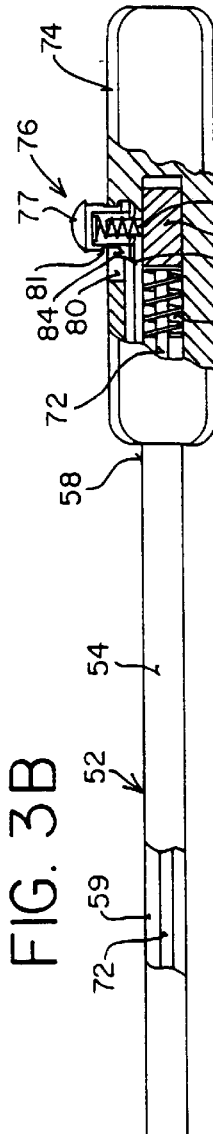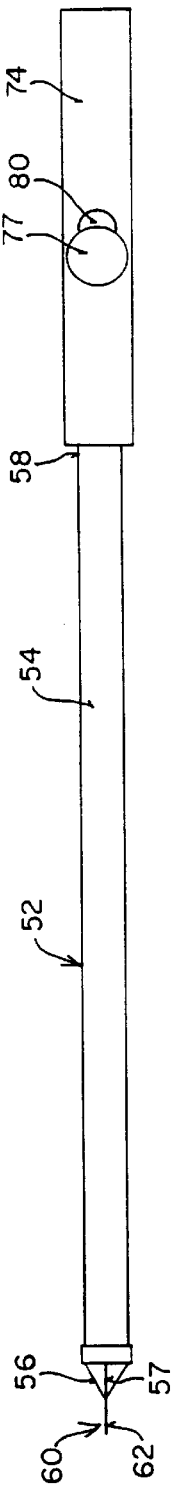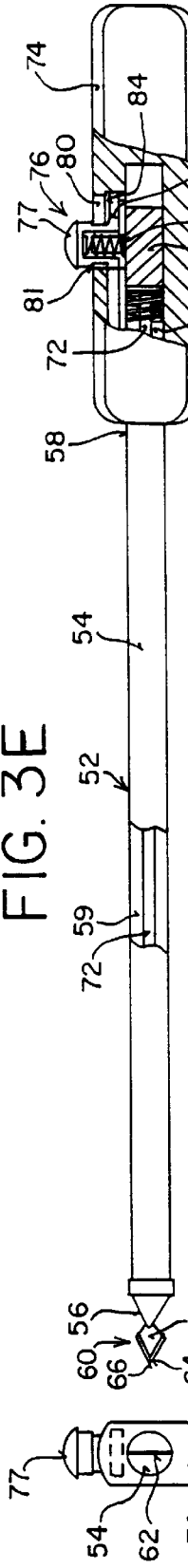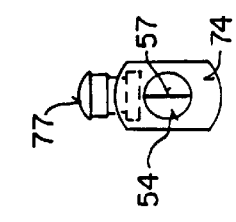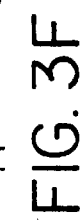

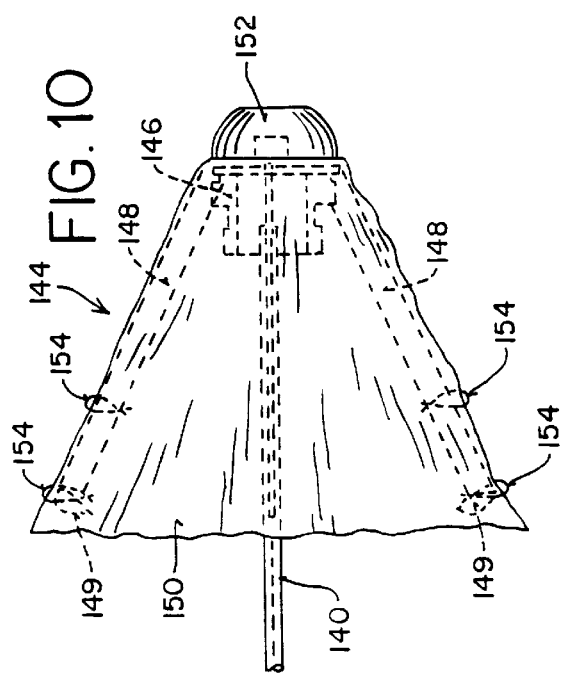
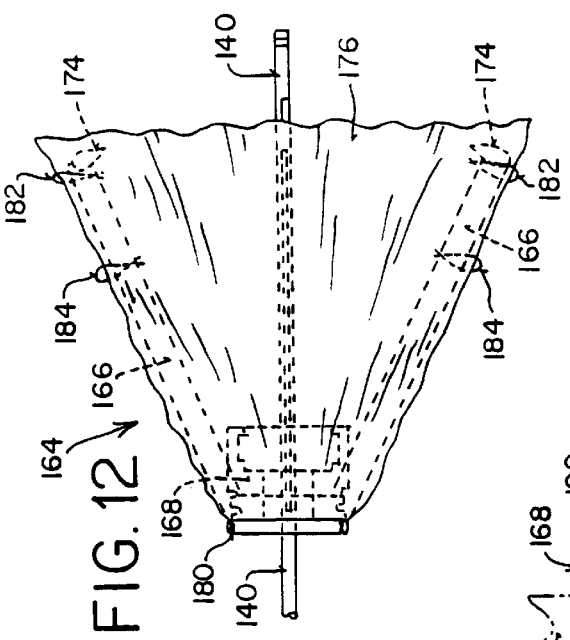
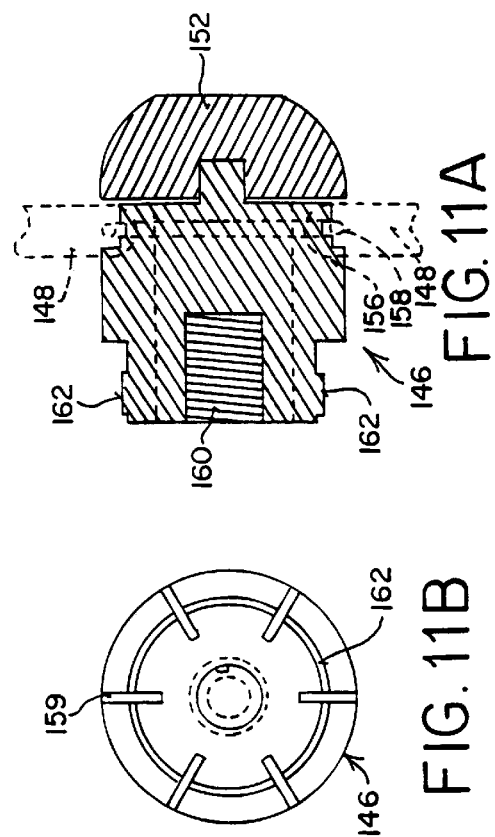
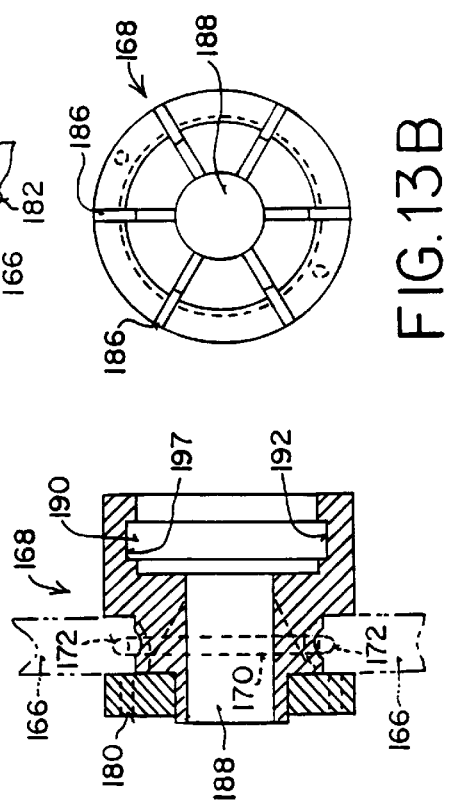

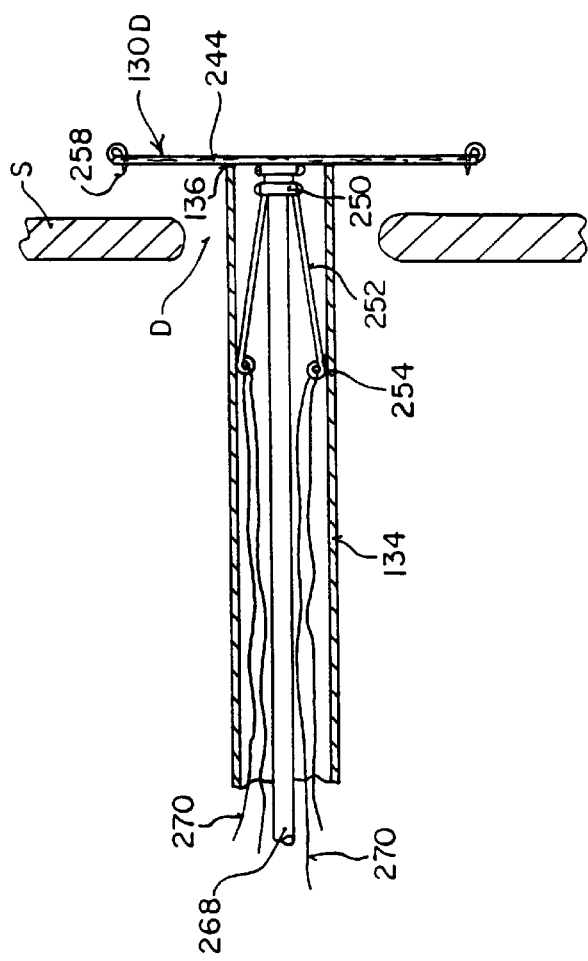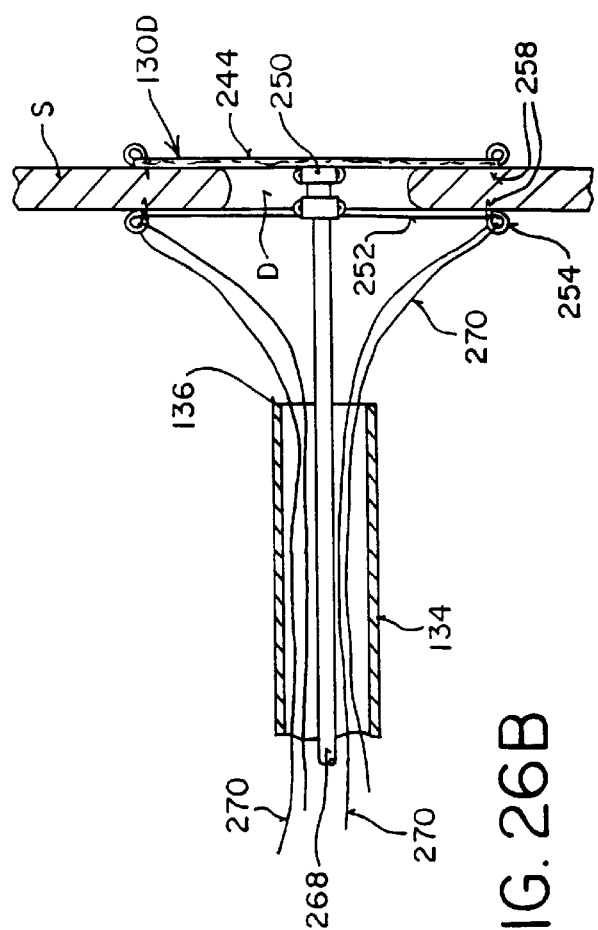
FIG. 26A
FIG. 26B

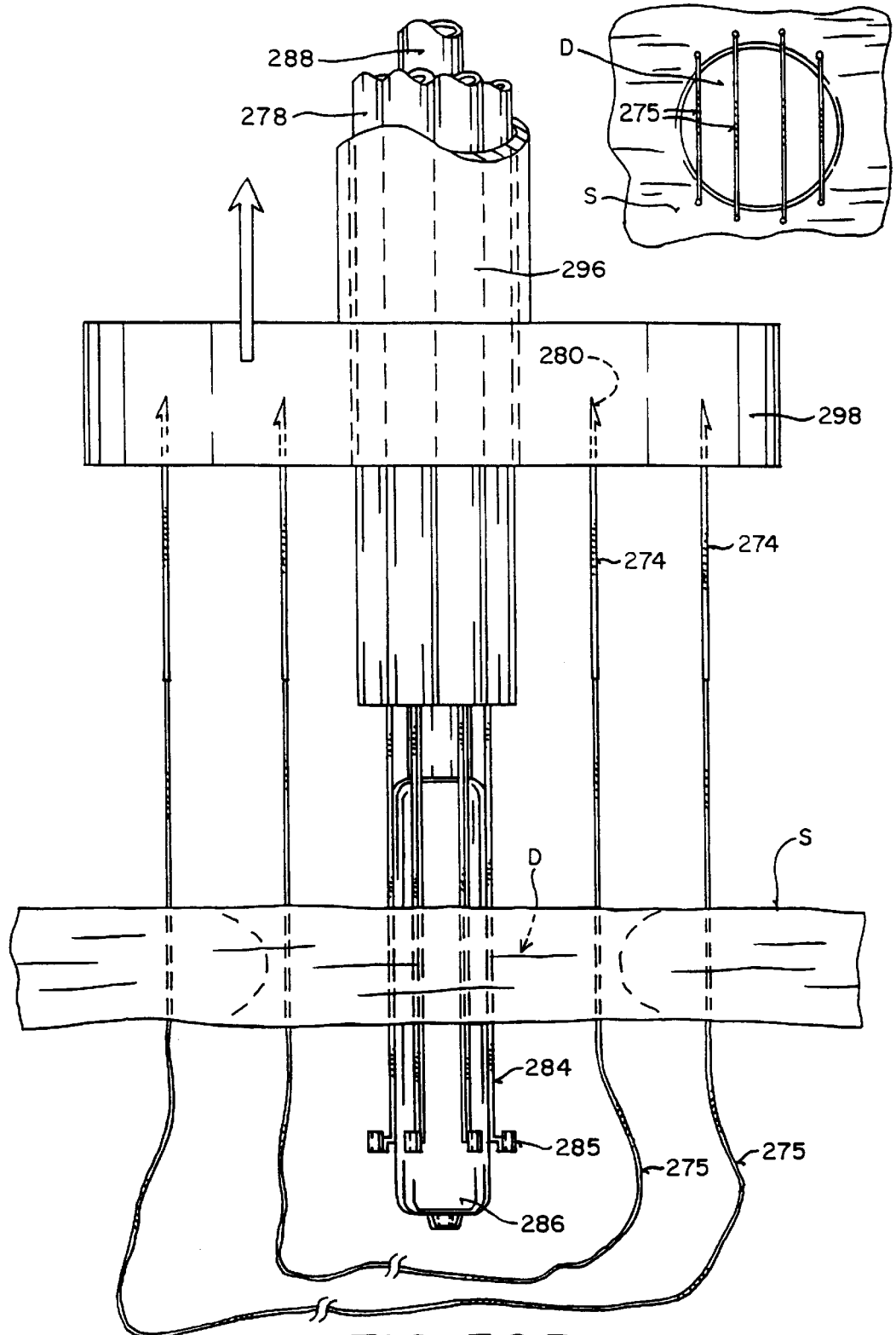

METHOD AND APPARATUS FOR THORACOSCOPIC INTRACARDIAC PROCEDURES

CROSS-REFERENCE TO RELATED APPLICATIONS

This is a division of application Ser. No. 08/425,179, filed Apr. 20, 1995 pending, which is a continuation-in-part of application Ser. No. 08/163,241, filed Dec. 6, 1993 now U.S. Pat. No. 5,571,215, which is a continuation-in-part of application Ser. No. 08/023,778, filed Feb. 22, 1993 now U.S. Pat. No. 5,452,733.

FIELD OF THE INVENTION

The present invention relates generally to less-invasive surgery of the cardiovascular system. More specifically, the invention relates to thoracoscopic devices and techniques for performing surgical procedures within the heart and great vessels while the heart is beating.

BACKGROUND OF THE INVENTION

Tens of thousands of people are born each year with congenital defects of the heart. Some of the more common types of congenital cardiac defects include atrial septal defect (ASD), ventricular septal defect (VSD), and patent ductus arteriosis (PDA). An ASD is a hole in the cardiac septum between the left and right atria, while a VSD is a hole in the septum between the left and right ventricles. Patent ductus arteriosis is incomplete closure of the opening between the pulmonary artery and the aorta that is present during fetal development. These conditions may cause blood to abnormally shunt from the right side of the heart to the left side of the heart without being properly oxygenated in the lungs, so that the body tissues supplied by the blood are deprived of oxygen. In addition, blood in the left side of the heart may shunt back to the right side through the defect rather than being pumped into the arterial system, causing abnormal enlargement of the right chambers of the heart.

ASD's, VSD's and PDA can frequently be surgically repaired with significant success. Smaller defects may be reparable by simply suturing the defect closed, while larger defects may require a patch of polyester, expanded polytetrafluoroethylene, or a portion of the patient's own pericardium to be sutured into the heart to cover and occlude the defect.

Ordinarily, such surgery is performed using open-chest techniques while the heart is under cardioplegic arrest and circulation is maintained by cardiopulmonary bypass. Using such techniques, a gross thoracotomy is created in order to gain access to the heart and great vessels, facilitating clamping and cannulation of the aorta for inducing cardioplegic arrest, and allowing instruments to be introduced into the chest cavity and into the heart to perform the surgical repair. The necessity of stopping the heart significantly heightens the risks attendant such procedures, particularly the risks of causing ischemic damage to the heart muscle, and of causing stroke or other injury due to circulatory emboli produced by aortic clamping and vascular cannulation. In addition, the creation of a gross thoracotomy produces significant morbidity and mortality, lengthens hospital stay and subsequent recovery, increases costs, and worsens the pain and trauma suffered by the patient. Moreover, many congenital defects are repaired in children under the age of ten years for whom the morbidity and mortality of openchest surgery and cardioplegic arrest can be even greater than for older patients.

In an effort to avoid the necessity of grossly opening the chest and stopping the heart, a number of intravascular devices have been developed for repair of ASD's, VSD's, and PDA. For example, U.S. Pat. No. 3,874,388 to King et al. discloses an intravascular delivery catheter introduced intraluminally from a peripheral vein into the right side of the heart which can be used to position an artificial umbrella-like patch across a septal defect and to anchor the patch to the cardiac septum. Other intravascular delivery devices and artificial patches for the repair of septal defects can be seen in U.S. Pat. No. 5,334,217, U.S. Pat. No. 5,284,488, U.S. Pat. No. 4,917,089, U.S. Pat. No. 4,007,743, and PCT Application No. PCT/US92/10141.

While intravascular approaches to the repair of congenital defects may provide certain advantages, the most significant of which is the elimination of the need for gross thoracotomy and cardioplegic arrest, these techniques have suffered from a number of problems. One such problem is the difficulty in manipulating the artificial patches into position across a defect using only the proximal end of a long and flexible delivery catheter positioned through a tortuous right lumen. Also problematic is the inadequacy of fixation of endovascularly-placed patches, creating a tendency of such patches to migrate or embolize after placement, which can allow blood to again shunt through the defect. In addition, once such a patch has been placed and the delivery catheter detached from the patch, relocating and repositioning the patch with the catheter is difficult, if not impossible, and may require open surgical correction. Moreover, in young children, the size of the peripheral vessels is extremely small, and damage to such vessels could have serious effects upon the growth of the child. Thus, the size of the devices which can be introduced through such vessels is greatly limited.

In addition to ASD, VSD, and PDA, various other types of cardiac disease also may be diagnosed and treated by intervention within the interior chambers of the heart. For example, some cardiac arrhythmias such as ventricular tachycardias, supraventricular tachycardias, and atrial fibrillation, may be diagnosed by obtaining access into an interior chamber of the heart and by performing electrophysiological mapping to identify abnormal conduction pathways. Once these abnormal conduction pathways are identified, in some cases the disease may be treated by ablating selected cardiac tissue using radiofrequency (RF) energy or a medical laser to eliminate the abnormal pathways. A number of endovascular approaches have been developed which attempt to allow intracardiac mapping and ablation using catheters introduced transluminally from peripheral vessels into the heart. Such devices are disclosed, for example, in U.S. Pat. Nos. 4,960,134, 4,573,473, 4,628, 937, and 5,327,889. However, endovascular mapping and ablation devices suffer from many of the same problems suffered by endovascular septal defect repair devices, including a lack of control and precise positionability from the proximal end of these highly flexible and elongated devices, the significant size constraints of peripheral vessels, and the inability to position the devices in all potentially diseased sites within the heart.

What are needed, therefore, are devices and methods to enable the repair of ASD, VSD, PDA, and other congenital defects, as well as cardiac arrhythmias and other diseases of the heart, which eliminate the need for gross thoracotomy and cardioplegic arrest, but which overcome the forementioned problems with intravascular techniques. The devices and methods should facilitate a high level of control for precise manipulation within the heart. The devices and methods should produce a septal defect or PDA repair which is reliable and long-lasting, and should not be susceptible to migration, embolization, or reopening of a defect. The devices and methods for septal defect and PDA repair should allow the position of a repair patch to be inspected after initial placement and to be repositioned if necessary. Finally, the devices and methods should not risk damaging the peripheral vessels of the patient, nor should the size and configuration of the devices be limited by the size of the patient's peripheral vessels.

SUMMARY OF THE INVENTION

The invention provides devices and methods that facilitate thoracoscopic access into the interior of the heart while the heart is beating. This intracardiac access can be used to perform a variety of diagnostic and treatment procedures within the heart without the need for a gross thoracotomy or cardioplegic arrest. The invention provides devices and methods for the performance of a number of different procedures including the repair of ASD, VSD, PDA, and other cardiac abnormalities, electrophysiological mapping and ablation for the treatment of cardiac arrhythmias, as well as a variety of other intracardiac procedures that can be performed thoracoscopically on a beating heart.

In a first aspect of the invention, a tubular access device is provided for accessing an interior chamber of a beating heart. The access device includes an elongated tubular body configured to extend percutaneously through an intercostal space between the ribs of the chest and through a muscular wall of the heart, and an inner lumen extending through the tubular body which provides an access channel into the heart. In an exemplary embodiment, the tubular access device has a length of at least 10 cm, and the inner lumen has a diameter of at least 5 mm. Preferably, the tubular access device is rigid to facilitate responsive and precise positionability from its proximal end.

In one embodiment, the access device includes means near a distal end thereof for sealing peripherally around a surrounding penetration in the muscular heart wall through which the access device is positioned. The sealing means may comprise one or a pair of inflatable balloons, a radially-expandable portion of the tubular body, or a flange at the distal end of the body. A purse string suture or other tissue-gathering means may be applied to the muscular heart wall surrounding the tubular body and tightened to prevent blood from flowing through the penetration around the access device.

The invention may further include an obturator positionable within an inner lumen of the tubular access device. The obturator may have means at its distal end for penetrating the muscular wall of the heart. The penetrating means may comprise a blade, radiofrequency electrode, or other type of cutting element. In a preferred embodiment, the obturator further includes means for selectively exposing the penetrating means, which may include a movable actuator for extending and retracting the cutting means from the distal end of the obturator.

The access device may include a hemostasis valve in the inner lumen to prevent blood flow out of the heart through the inner lumen, and to allow instruments to be introduced through the inner lumen while maintaining hemostasis in the inner lumen. The hemostasis valve may be disposed at either the proximal end or the distal end of the access device. Alternatively, when the access device is utilized in the lower-pressure right atrium, right ventricle, or left atrium, the access device may be positioned in a generally vertical orientation so that blood flow through the inner lumen is prevented by the pressure head of blood within the inner lumen being greater than the pressure in the cardiac chamber, eliminating the need for a hemostasis valve.

With the access device positioned through an intercostal space and through a wall of the heart, a straight and relatively large channel directly into the interior of the heart is available for the introduction of devices for diagnostic and treatment procedures. In a preferred embodiment, the invention provides systems and methods for repairing atrial and ventricular septal defects through the inner lumen of the access device. The septal defect repair system includes, in addition to the above-described access device, a closure means for closing or occluding the septal defect, and a means for introducing the closure means through the access device into the interior of the heart.

In a first embodiment, the closure means comprises a patch that may be attached to the cardiac septum to cover and occlude the septal defect. The patch includes a collapsible frame, and a flexible patch material attached to the frame. The flexible patch material may be an artificial biocompatible material such as polyester or expanded polytetrafluorethylene, or a portion of the patient's pericardium or other natural body membrane. The frame is configured to support the patch material at its outer edges in a generally flat configuration, and is sufficiently rigid to retain its shape against the pressure of blood within the heart, while having sufficient flexibility and resiliency to be collapsible for introduction through the inner lumen of the access device. In an exemplary embodiment the frame comprises a hub and a plurality of spokes extending radially outward from the hub. A circumferential wire or suture thread extending between the outer tips of the spokes may be provided to continuously support the outer edges of the patch. The hub is a rigid material such as stainless steel, is small enough to fit within the inner lumen of the access device, and is configured to be detachably coupled to the distal end of an delivery shaft (described below). The spokes are flexible, resilient wires of Nitinol™ or other material exhibiting similar super-elastic characteristics. The patch may be mounted to the frame by sutures, heat welding, adhesive, or other means.

The patch includes a means for securing the patch to the cardiac septum. The securing means may comprise a second patch coupled to a central portion of the first patch and parallel thereto such that one patch may be positioned through the septal defect on the left side of the cardiac septum and the second patch positioned on the right side of the cardiac septum, with the outer edges of the two patches compressively engaging the cardiac septum between them. For example, in the hub and spoke embodiment describe above, two sets of spokes may be mounted to the hub and a patch mounted to each set of spokes so that the two patches are generally parallel to each other and spaced slightly apart. Alternatively, the securing means may comprise a plurality of flexible wire struts coupled to a central part of the frame such that the outer ends of the struts will compressively engage the cardiac septum on the side opposite that on which the patch is positioned. Like the patch, the securing means is collapsible to allow introduction through the inner lumen of the access device. To facilitate secure fixation to the septum, the frame or the securing means may include pins or spikes pointing generally perpendicular to the patch to partially penetrate the cardiac septum when the patch has been positioned across the defect, preventing migration of the patch.

The patch is introduced into the heart and positioned across the septal defect by means of a rigid delivery shaft which may be positioned through the inner lumen of the access device. The delivery shaft includes an interior lumen or aperture at its distal end for receiving the patch and securing means in a collapsed configuration. The delivery shaft further includes a means for deploying the patch and the securing means, which may comprise a rod slidably disposed in a lumen through the delivery shaft. The rod includes means at its distal end for releasably coupling to the patch, such as a threaded extension which couples to a threaded hub in the patch frame. The rod may be advanced distally relative to the delivery shaft to deploy the patch from the aperture into the heart chamber on the side of the cardiac septum further away from the point of introduction, e.g., the left atrium if the device has been introduced into the heart through the right atrium. The patch is positioned against the septum, and the securing means is deployed on the side of the cardiac septum opposite the patch, e.g., the right atrium in the aforementioned case. The rod may then be decoupled from the patch and the delivery shaft is removed from the patient through the access device.

Advantageously, the delivery shaft and deployment means are configured to allow the patch to be re-collapsed and repositioned if the position of the patch is not satisfactory after initial deployment. In one embodiment, the rod is drawn proximally relative to the delivery shaft, whereby the patch is collapsed by engagement with the distal end of the delivery shaft. The patch securing means may be collapsed in a similar manner, or by a separate mechanism. In an exemplary embodiment, one or more wires or sutures extend through a lumen in the delivery shaft and are coupled to the securing means, e.g. to the outer ends of the spokes or struts of the securing means. By exerting tension on the wires, the securing means is drawn proximally into a collapsed configuration to allow it to be received in the aperture in the delivery shaft. This allows the patch and securing means to be drawn back into the aperture in the delivery shaft and redeployed at the desired position.

In an alternative embodiment, the septal defect closure means comprises a suturing device for applying at least one suture across the septal defect. The suturing device includes a rigid delivery shaft suitable for introduction through the inner lumen of the access device, and a plurality of needle holders mounted to the delivery shaft for releasably holding at least two needles connected by a suture thread. The needle holders are movable between a contracted position suitable for introducing the needles through the septal defect into the cardiac chamber on the opposite side of the septum, and an expanded position in which the tips of the needles are aimed proximally toward the cardiac septum on opposing sides of the septal defect. In one embodiment, the needle holders are mounted on opposing sides of a balloon which may be deflated during introduction through a septal defect and then inflated to move the needles into the expanded position. The needle holders are then pulled proximally so that the needles penetrate the cardiac septum. A means is mounted to the delivery shaft for capturing the distal tips of the needles after penetrating the septum. For example, the needles may have barbed tips which engage a porous fabric disk slidably mounted to the delivery shaft. The needle capture means is retracted to draw the needles through the septum and out of the heart through the inner lumen of the access device. In this way, a plurality of sutures may be applied to the cardiac septum simultaneously. Knots may then be tied in the sutures extracorporeally, and, using a long-handled endoscopic knot-pusher, pushed through the access device into the heart so as to tighten the sutures and draw the opposing sides of the septal defect together.

In a further aspect of the invention, a method of accessing an interior chamber of a beating heart is provided. According to the method of the invention, a penetration is formed in a muscular wall of the heart into an interior chamber of the heart, and a distal end of a tubular access device having an inner lumen is positioned through the penetration. The penetration may be formed with various types of endoscopic cutting devices, but, in a preferred embodiment, is formed with the cutting means at the distal end of the obturator, which is positioned in the inner lumen of the access device. This allows the access device to be introduced immediately upon forming the penetration, minimizing blood loss through the penetration. The method further includes the step of forming a hemostasis seal between the access device and the penetration to inhibit blood loss through the penetration. This step may include placing a purse string suture in the wall of the heart around the penetration, inflating a balloon mounted to the access device within the chamber of the heart, or radially-expanding a portion of the access device within the penetration.

The method also includes preventing blood flow out of the chamber of the heart through the inner lumen of the access device. This may be accomplished by positioning the access device in a vertical orientation so that the pressure head of blood in the inner lumen is sufficient to prevent blood flow out of the heart, or a hemostasis valve may be provided in the inner lumen.

While the method of accessing an interior chamber of the heart may find use in openchest surgical procedures, it is preferably performed using thoracoscopic techniques, wherein the ribs and sternum remain intact and are not significantly retracted during each step of the procedure. Using such techniques, a working space may be created in the patient's chest cavity by collapsing one of the patient's lungs or using jet ventilation techniques. A viewing space such as an endoscope or endoscopic surgical microscope may then be introduced through an intercostal space into the working space to view the exterior of the heart while the penetration is formed and the access device is introduced. The viewing scope may include a video camera to provide a video image of the heart for display on a monitor which can be viewed during the procedure. Alternatively, the heart may be viewed directly through a lens on the viewing scope or through a trocar sleeve positioned in an intercostal space.

The method of accessing an interior chamber of the heart facilitates the performance of a variety of intracardiac diagnostic and treatment procedures. While it may be desirable to place the patient on cardiopulmonary bypass and arrest the heart during certain procedures, the invention facilitates the performance of a number of cardiac procedures while the heart is beating, without the need for cardiopulmonary bypass or cardioplegic arrest, and with significantly reduced risk of injury resulting from embolism.

In a further aspect of the invention, a method is provided for closing a cardiac septal defect in a patient's heart. The patient is first placed under general anesthesia. The method is initiated by positioning the distal end of the tubular access device in an interior chamber of the heart and creating a hemostatic seal around the access device, as described above. These steps are preferably performed under visualization by means of an endoscope or other percutaneous visualization device. One or more instruments are then passed through the inner lumen of the access device and out of the distal end thereof. The one or more instruments are then used to close the septal defect.

In a preferred embodiment, the method of the invention is performed while the patient's ribs and sternum remain intact and unretracted, and while the patient's heart is beating. Access into the chest cavity is obtained through small percutaneous incisions or punctures in the intercostal spaces between the ribs. Trocar sleeves, ports, or other types of percutaneous access cannulae may be placed in these incisions or punctures to protect and retract surrounding tissue to facilitate introduction of instruments into the chest cavity.

Usually, the interior chamber of the heart will be the right atrium, right ventricle, or left atrium, in which blood pressure is lower than in the left ventricle. Preferably, the access device is positioned in a vertical orientation, usually from a lateral side of the chest, with the distal end of the access device disposed in the interior chamber. In this way, the static pressure head of blood within the inner lumen is equal to the pressure within the interior chamber, preventing the flow of blood out of the interior chamber through the inner lumen. In an exemplary embodiment, small incisions and/or access ports are placed in the third, fourth, fifth, or sixth intercostal spaces on a lateral side of the chest. At least three such ports are usually required, one for introduction of the access device, one for introduction of a visualization device such as an endoscope, and one for introduction of other instruments for suturing, retraction, and other purposes.

Visualization within the interior of the heart may be provided by various means. Preferably, an ultrasonic probe is positioned in the patient's esophagus, on the surface of the patient's chest, or in the chest cavity adjacent or in contact with the exterior of the heart to ultrasonically image the interior of the heart. Alternatively, an endoscope with a translucent bulb or balloon over its distal end may be introduced into the heart through the access device or through a separate incision in the wall of the heart to allow video-based or direct visualization of the interior of the heart. An angioscope introduced into the heart endovascularly through a peripheral vessel may also be used for intracardiac visualization. Fluoroscopy is an additional technique for visualization.

The septal defect may be repaired in any of several ways. A patch may be attached to the cardiac septum to cover the defect, or the defect may be sutured closed. As described above, the patch may be an artificial biocompatible material, or it may be created out of a portion of the patient's pericardium or other natural membrane in the patient's body. The patch is introduced through the inner lumen of the access device by means of a rigid delivery shaft to which the patch is detachably coupled, allowing the patch to be positioned with a high degree of control and precision. The patch is inserted through the septal defect into the left side of the heart in a collapsed configuration, and then expanded to cover the defect. When the patch has been positioned across the defect, the interior of the heart is visualized by ultrasonic imaging, fluoroscopy with contrast dye injection, or other means to determine whether the defect has been closed adequately. If not, the patch may be retrieved and repositioned with the delivery shaft. Once positioned properly, the patch is anchored to the cardiac septum, preferably by the compressive force of an opposing patch, frame or series of struts disposed on the right side of the septum. A number of pins or spikes may be provided on the patch to partially penetrate the septum to prevent migration. The patch is then released from the delivery shaft.

In those embodiments in which the patch comprises a portion of the pericardium or other natural membrane, the invention allows the portion of membrane to be harvested from the patient's body and then affixed to a frame outside of the body cavity. Preferably, the membrane is harvested using instruments introduced percutaneously through intercostal spaces, while keeping the ribs and sternum intact. The membrane may be affixed to the frame using sutures, tissue adhesive, staples, or the like. Once the membrane is attached to the frame, the two may be coupled to the delivery shaft and introduced through the inner lumen of the access device into the heart for attachment to the cardiac septum.

Where the septal defect is to be closed by means of sutures, at least two needles connected by a length of suture are introduced through the access device and inserted through the defect while the needles are in a radially retracted position. The needles are held in needle holders coupled to the end of a delivery shaft. After insertion through the defect, the needles are repositioned into a radially expanded position in which they are further separated from one another. A balloon, expandable wire basket, scissors-type linkage, or camming device may be used for this purpose, or the needles may be held in needle holding rods having a shape memory so as to assume the radially expanded configuration when unrestrained. The needles are then drawn through the cardiac septum while in the expanded position. The needles are captured, and both ends of the length of suture are then tensioned to close the defect. Usually the length of suture is long enough to allow the suture needles to be drawn outside of the body cavity through the inner lumen of the access device. Knots are then formed extracorporeally and pushed through the access device up to the cardiac septum using an endoscopic knot pusher. The sutures are trimmed using endoscopic scissors, and the repair is examined using one of the aforementioned visualization techniques.

Once the septal defect has been closed, the access device is withdrawn from the penetration in the wall of the heart. If a balloon or a radially expanding portion of the access device has been utilized for hemostasis, it is first deflated or radially contracted. As the distal end of the access device is withdrawn, the purse string suture in the heart wall surrounding the access device is pulled tight, closing the penetration. Knots are then formed in the purse string suture, either intracorporeally using endoscopic instruments, or extracorporeally, after which the knots are pushed into the body cavity and against the heart wall using an endoscopic knot pusher. Alternatively, the penetration in the heart wall may be closed using endoscopic suturing or stapling techniques after the access device has been withdrawn. All access ports are then withdrawn, percutaneous incisions and punctures are closed, and the patient is recovered from anesthesia.

In a further aspect of the invention, devices and methods are provided for performing electrophysiological procedures within the heart. Such procedures include electrophysiological cardiac mapping and ablative treatment of cardiac arrhythmias, including ventricular and supraventricular tachycardias and atrial fibrillation. The invention provides devices and methods for diagnosis and treatment of such diseases by accessing the interior of the heart through the intracardiac access device described above. Such techniques avoid the need for a gross thoracotomy, and offer more control and precision in diagnosing and treating these diseases than are offered by intravascular electrophysiological treatment techniques.

An electrophysiological device according to the invention comprises a rigid shaft suitable for introduction through the inner lumen of the access device. A deflectable tip is attached to the distal end of the shaft. The deflectable tip has at least one and usually a plurality of electrodes mounted to it. A steering means is provided in the shaft for deflecting the tip into the desired orientation. The electrodes are electrically coupled to a connector at the proximal end of the shaft, which may be connected to a sensitive electrocardiogram (ECG) monitoring apparatus or a radiofrequency generator?. The deflectable tip may be introduced into a chamber of the heart through the access device, and the electrodes positioned against a site on an interior wall of the heart to perform an electrophysiological procedure. For example, a plurality of electrode bands may be mounted in a spaced-apart relationship on the deflectable tip, and the voltage difference can be measured across selected electrodes to identify aberrant conduction pathways in the heart wall, a process known as cardiac mapping. In addition, radiofrequency current may be delivered through one or more electrodes to ablate tissue at selected sites on the heart wall.

In a second embodiment, an electrophysiological device according to the invention comprises an expandable electrode array mounted to the distal end of the rigid shaft. The electrode array includes a plurality of electrodes mounted to an expandable support structure such as a frame, basket, balloon, or series of rods. The support structure is coupled to an actuator at the proximal end of the shaft to facilitate selective deployment of the electrode array from a contracted configuration, in which it may be introduced through inner lumen of the access device, to an expanded configuration, in which the electrodes are spread apart into a two-dimensional or three-dimensional array. In one embodiment, the electrode array is configured to conform generally to the shape of an interior chamber of the heart in the expanded configuration. In this way, the electrodes may be positioned in a pattern along the interior walls of the heart chamber to facilitate mapping or ablation of a large area without moving the device.

The electrophysiological devices of the invention are particularly advantageous in that they offer a high degree of control and precision in positioning within the heart. Because the devices are manipulated by means of a rigid shaft that spans only the relatively short distance from the interior of the heart to the exterior of the chest cavity, the electrodes can be easily and precisely positioned at most locations within the heart chamber. Moreover, because the electrophysiological devices are not introduced endovascularly, they are not limited in size and configuration by blood vessel size. The devices may therefore have electrodes which are larger than those of endovascular electrophysiology devices, permitting the delivery of greater amounts of energy to a tissue site. Further, the electrodes may be greater in number and spread out over a larger area than endovascular electrophysiology devices, allowing a greater area of a heart chamber to be mapped or ablated without moving the device, thus increasing the precision and efficiency of the procedure.

In a method of electrophysiological intervention according to the invention, the tubular access device is introduced into a chamber of the heart in the manner described above. An electrophysiology device including at least one electrode coupled to the distal end of a shaft is introduced through the tubular access device into the heart chamber. The electrode is positioned at a tissue site on a wall of the heart chamber, and either radiofrequency current is delivered to the tissue site through the electrode, or electrical potential is sensed between two or more selected electrodes. This technique may be used for either cardiac mapping or ablation of tissue. The method may further include deflecting a flexible tip attached to the shaft so that the electrode is positioned away from a longitudinal axis of the shaft, permitting the electrode to be positioned at various locations within the heart chamber. Alternatively, the method may include a step of expanding an electrode array into an expanded configuration within the heart chamber. In the expanded configuration, a plurality of electrodes of the electrode array are positioned in a two or three dimensional array which may be positioned adjacent a treatment area on an interior wall of the heart chamber. Electrical potentials in the heart wall tissue may then be sensed between selected electrodes, or radiofrequency current may be delivered to the treatment area through one or more electrodes of the electrode array.

The method may be performed in either the right side or the left side of the heart, and in either the atria or the ventricles. In ventricular procedures, because it may be undesirable to form a penetration in the wall of a ventricle, the electrophysiology device may be introduced through the access device into an atrium, from which it is advanced through the tricuspid valve or mitral valve into the ventricle. Alternatively, the electrophysiology device may be positioned transeptally through a puncture in the cardiac septum, wherein, after electrophysiological treatment is complete, the device is withdrawn and the septal puncture closed.

The devices and methods of the invention may also be useful in combination with other types of cardiac treatment procedures. For example, the electrophysiology devices of the invention may be useful for mapping conduction pathways in the heart, which are then treated by means of thoracoscopic, endovascular, or open-chest techniques. Alternatively, thoracoscopic or endovascular techniques may be used for mapping, and the intracardiac electrophysiological devices of the invention may then be used for ablation or other treatments. In one exemplary procedure, a thoracoscopic mapping device is introduced through an intercostal port in the chest for mapping cardiac conduction pathways on the exterior surface of the heart. The intracardiac electrophysiology device of the invention is then utilized in the interior of the heart to perform ablation, utilizing the mapping information generated on the exterior of the heart. Such a technique could be used for treatment of ventricular and supraventricular tachycardias. Similarly, to treat atrial fibrillation, intracardiac mapping may be performed using the electrophysiology device of the invention, and thoracoscopic or endovascular cutting or ablation instruments may then be utilized through intercostal ports to perform a Cox "maze"-type surgical transection of the atrium, whereby the mapping information is used to make precise incisions or ablation lines in the myocardium to create a directed conduction pathway between the sinoatrial node and the atrioventricular node.

By providing access to the interior of the heart without requiring a gross thoracotomy and without the need to induce cardioplegic arrest, the invention enables a variety of intracardiac procedures to be performed on a beating heart. In addition to septal defect repair and the electrophysiological procedures described above, these procedures may include repair of other types of congenital defects, transmyocardial laser revascularization, mitral, aortic, pulmonary, or tricuspid valve inspection and repair, pulmonary thrombectomy, intracardiac inspection, removal of growths, myxomas, neoplasms, hypertrophic obstructive cardiopmyopathy and vegetations, and other diagnostic and treatment procedures.

The nature and advantages of the invention will become more apparent from the following detailed description of the invention when taken in conjunction with the accompanying exemplary drawings.

BRIEF DESCRIPTION OF THE DRAWINGS

FIG. 2 is a front partial cut-away view of a patient's heart showing the intracardiac access device positioned through a wall thereof.

FIGS. 2A–2E are side views of a distal portion of the intracardiac access device of FIG. 1 showing various alternative types of sealing means.

FIGS. 3A–3C are side, top, and end views, respectively, of the obturator of an intracardiac access device according to the invention with the cutting means retracted.

FIGS. 3D–3F are side, top, and end views, respectively, of the obturator of an intracardiac access device according to the invention with the cutting means extended.

FIG. 10 is a side elevational view of a partially-deployed distal patch of a septal defect repair device useful in the method of the invention.

FIGS. 11A–11B are side cross-sectional and end views, respectively, of a hub of the distal patch of FIG. 10.

FIG. 12 is a side elevational view of a proximal patch of a septal defect repair device useful in the method of the invention.

FIGS. 13A–13B are side cross-sectional and end views, respectively, of a hub of the proximal patch of FIG. 12.

FIGS. 26A–26B is a side cross-sectional view showing the attachment of the septal defect repair device of FIGS. 24A–24B to a cardiac septum according to the method of the invention.

FIG. 30B is a side view of the cardiac septum of FIG. 30A showing withdrawing the needles from the cardiac septum according to the method of the invention.

FIG. 31A is a top view of the cardiac septum of FIG. 30A showing the position of the sutures across the septal defect according to the method of the invention.

DETAILED DESCRIPTION OF SPECIFIC EMBODIMENTS

Figure 1:
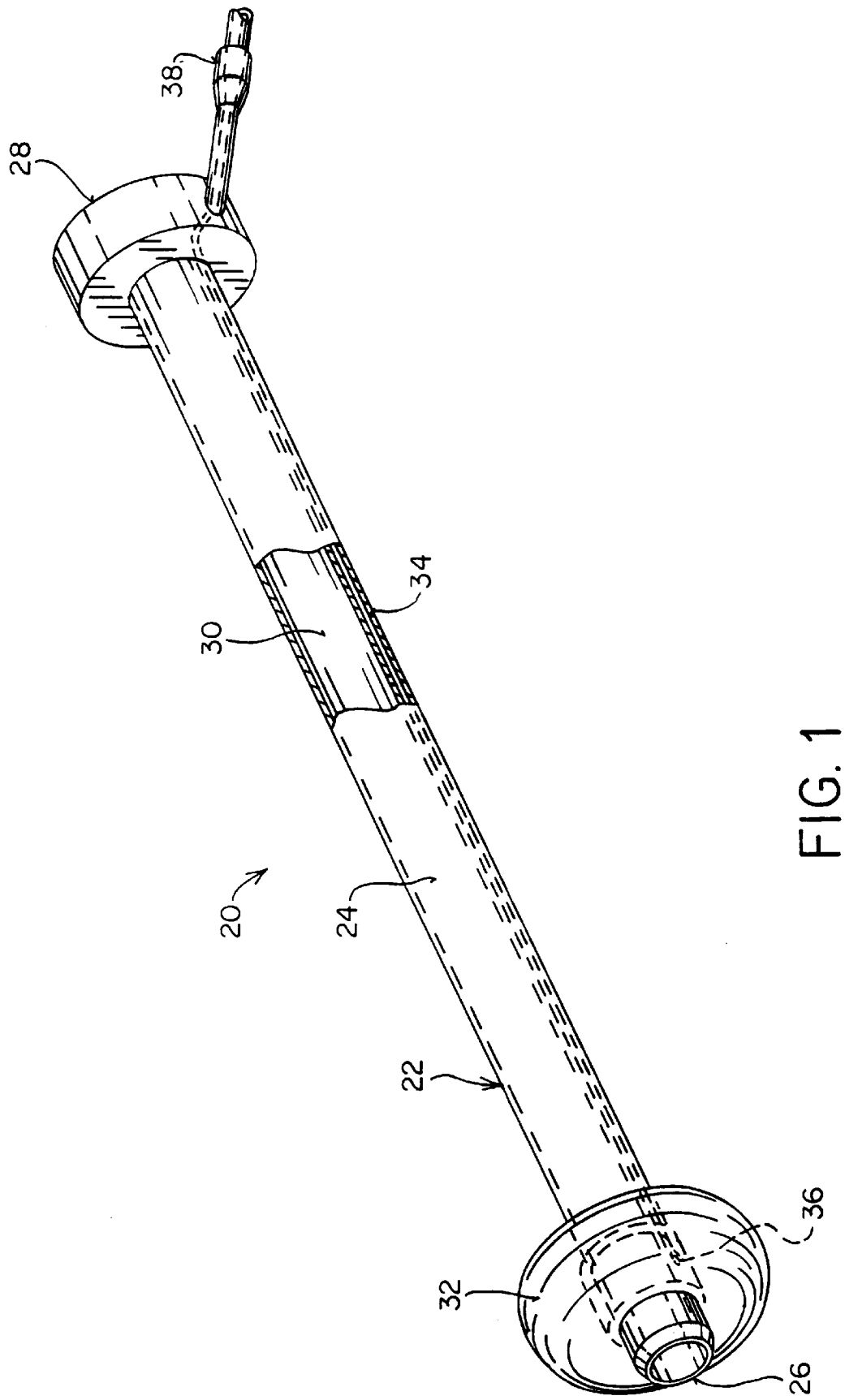
FIG. 1 is a perspective view of an intracardiac access device according to the invention.

A first representative embodiment of an intracardiac access system according to the invention is illustrated in FIG. 1. The intracardiac access system 20 includes a tubular access device 22 comprising a rigid shaft 24 having a distal end 26, a proximal end 28, and an inner lumen 30 extending therebetween. Access device 22 includes a means near distal end 26 for hemostatically sealing a cardiac penetration through which shaft 24 is introduced, which may comprise a toroidal balloon 32. An inflation lumen 34 extends through shaft 24 and has an opening 36 in communication with the interior of balloon 32. An inflation fluid port 38 is mounted to shaft 24 at proximal end 28 in communication with inflation lumen 34 and is configured for connection to an inflation fluid delivery source such as a syringe or other balloon inflation device.

Access device 22 is configured to extend percutaneously through an intercostal space and through a muscular wall of the heart with distal end 26 positioned in an interior chamber of the heart and proximal end 28 positioned outside of the patient's chest cavity. In an exemplary embodiment, the tubular access device has a length of about 10 to 30 cm, preferably about 25 cm, and an outer diameter of less than about 15 mm, and preferably about 5–10 mm. To allow introduction of instruments for visualization and surgical intervention within the heart, inner lumen 30 has a diameter of at least about 5 mm. Preferably, access device 22 is a rigid material such as stainless steel, titanium, or a rigid polymer, with a minimum durometer of about 75 Shore A. Alternatively, shaft 24 of access device 22 may be all or partially flexible with a minimum durometer of about 35 Shore A, and may also include pull wires or other means for steering or deflecting distal end 26.

As illustrated in FIG. 2, distal end 26 of access device 22 is configured to be introduced through a penetration in cardiac wall 40 of heart H. The hemostatic sealing means, e.g. balloon 32, functions to seal the penetration around the exterior of shaft 24 to prevent leakage of blood through the penetration from the interior of heart H. As illustrated in FIGS. 2A–2E, a variety of hemostatic sealing means may be utilized. Balloon 32 may be mounted to shaft 24 spaced a short distance from distal end 26 so as to be positionable against the exterior surface of cardiac wall 40, as shown in FIG. 2A. Balloon 32 may alternatively be mounted close to distal end 26 so as to be positionable against the interior surface of cardiac wall 40 as shown in FIG. 2B. In addition, a pair of balloons 32, 42 may be mounted to shaft 24 spaced slightly apart to provide a seal on both sides of cardiac wall 40, as shown in FIG. 2C.

In a further alternative embodiment, not pictured, either or both of balloons 32, 42 of FIG. 2C may be replaced by expanding mechanical elements, such as moly-type fittings which are expanded under compression exerted by, for example, sliding a slidable sleeve axially over shaft 24 which engages the proximal ends of the fittings.

In a further embodiment, shown in FIG. 2D, shaft 24 may have a flange 44 disposed at distal end 26, flange 44 having a proximal end 46 with an outer diameter larger than that of shaft 24. When flange 44 is introduced through a cardiac penetration, proximal end 46 of flange 44 may be positioned so as to abut and seal against the interior surface of cardiac wall 40. Flange 44 preferably has tapered side walls 48 to facilitate introduction through the cardiac penetration. As shown in FIG. 2, balloon 32 may be mounted to shaft 24 spaced proximal to flange 44 to compress cardiac wall 40 between the balloon and the flange and seal the cardiac penetration both interiorly and exteriorly.

In another embodiment, illustrated in FIG. 2E, shaft 24 has a radially-expanding portion 50 near distal end 26 which may be selectively expanded when distal end 26 has been positioned through the cardiac penetration. Exemplary radially-expanding dilators and cannulae having a construction suitable for application to the present invention are disclosed in U.S. Pat. Nos. 5,183,464 and 4,921,479, which are incorporated herein by reference. A balloon 32 may also be mounted to shaft 24 distally of radially-expanding portion 50 to seal against the interior surface of cardiac wall 40.

In each of the forementioned embodiments, it will frequently be advantageous to place a purse string suture in cardiac wall 40 or apply another means of gathering tissue around the cardiac penetration through which shaft 24 is introduced to enhance hemostasis. The placement of such a purse-string suture is described in detail below.

Referring now to FIGS. 3A–3C and 3D–3F, cardiac access system 20 further includes an obturator 52 removably positionable in inner lumen 30. Obturator 52 comprises a tubular shaft 54 having a distal end 56, a proximal end 58, and an axial lumen 59. Distal end 56 is conical in shape and has a transverse slot 57 in communication with axial lumen 59. A cutting means 60 for forming a penetration in a heart wall is slidably received within slot 57, and, in an exemplary embodiment, comprises a stainless steel blade 62 having a sharpened distal edge 64 tapering to a point 66. Blade 62 is coupled to a linkage 72 slidably disposed in axial lumen 59. A handle 74 is mounted to proximal end 58 of shaft 54, and a sliding actuator 76 is mounted to handle 74. Linkage 72 is coupled to actuator 76, so that actuator 76 may be used to slide blade 62 distally to expose edge 64 and point 66. A compression spring 78 is disposed within an aperture in handle 74 and engages a collar 79 on linkage 72 to bias blade 62 proximally so that it is protected within slot 57.

Actuator 76 may be configured to lock in a distal position in which blade 62 is fully exposed, in a proximal position in which blade 62 is fully exposed, or in any other position between the two. In an exemplary configuration, actuator 76 comprises a button 77 having an upper portion 81 of smaller diameter which is slidable within a channel 80 in handle 74, and having a lower portion 82 of larger diameter designed to seat within a detent 84 at the proximal end of channel 80. Button 77 is biased upward by a spring 85 to automatically lock into detent 84 when aligned therewith. In this way, blade 62 is locked in the proximal position and is unlikely to be inadvertently exposed by the user. When exposure of blade 62 is desired, button 77 is pushed downward and distally. Release of pressure on button 77 causes blade 62 to retract automatically.

The length of shaft 54 is selected so that when obturator 52 is disposed within inner lumen 30, cutting means 60 extends distally of distal end 26 of access device 22 and handle 74 is near or against proximal end 28 of access device 22. In this way, blade 62 may be used to create a penetration in the heart wall while obturator 52 is positioned within access device 22, allowing access device 22 to be introduced through the heart wall as or immediately after the penetration is formed, thereby minimizing blood loss through the penetration. Once access device 22 is introduced through the cardiac penetration, obturator 52 is withdrawn from inner lumen 30.

As will be described more fully below, access device 22 is usually introduced into the right atrium, right ventricle, or left atrium in a vertical or near-vertical orientation so that blood flow out of the heart through inner lumen 30 is prevented by gravity—i.e., the pressure head of blood in inner lumen 30 is equal to that in the cardiac chamber. In such cases, there is no need for a hemostasis valve within inner lumen 30. However, in cases in which access device 22 is to be introduced into the higher pressure chamber such as the left ventricle, or in which access device 22 is to be positioned in an orientation in which blood might flow through inner lumen 30, a hemostasis valve (not shown) may be provided within inner lumen 30. The hemostasis valve may be positioned at the proximal end, the distal end, or a mid-position within inner lumen 30, and will be configured to allow instruments to be introduced through inner lumen 30 with minimal blood loss. Suitable hemostasis valves are described, for example, in U.S. Pat. Nos. 4,000,739, 4,436,519, 5,154,701, 4,946,133, 5,000,745, 4,177,814, and 5,300,033, which are incorporated herein by reference.

A method of accessing the interior of the heart according to the invention will now be described with reference to FIGS. 4–8. The method will be described in relation to accessing a left or right atrium of the heart from the right side of the chest, but it should be understood that the principles described will be equally applicable to accessing the left or right ventricle and using any of a variety of approaches.

The patient is prepared for cardiac surgery in the conventional manner, and general anesthesia is induced. The patient is positioned on the patient's left side so that the right lateral side of the chest is disposed upward. Two to three small incisions 2–3 cm in length are made between the ribs, usually in the third, fourth, or fifth intercostal spaces. Thoracoscopic access ports 90 (e.g. trocar sleeves or other tubular cannulae), are positioned in each incision to retract away adjacent tissue and protect it from trauma as instruments are introduced into the chest cavity. Access ports 90 have an outer diameter which does not require retraction, cutting or removal of ribs, preferably less than 14 mm, and an axial passage with a diameter less than about 12 mm. Access ports 90 may also be non-circular in cross-section, or may be made of a flexible material to deform into a non-circular shape when introduced between two ribs. The right lung is deflated using conventional techniques, usually by introducing a tube through the patient's trachea into the right lung and applying a vacuum through the tube to deflate the lung. An endoscopic visualization device such as a thoracoscope 92 connected to a video monitor (not shown) by a cable 93 is introduced through one of access ports 90 to visualize the interior of the chest cavity. Atraumatic retraction instruments may be introduced through access ports 90 to assist in deflating and retracting the lung, thereby providing a working space within the chest cavity.

Figure 4:
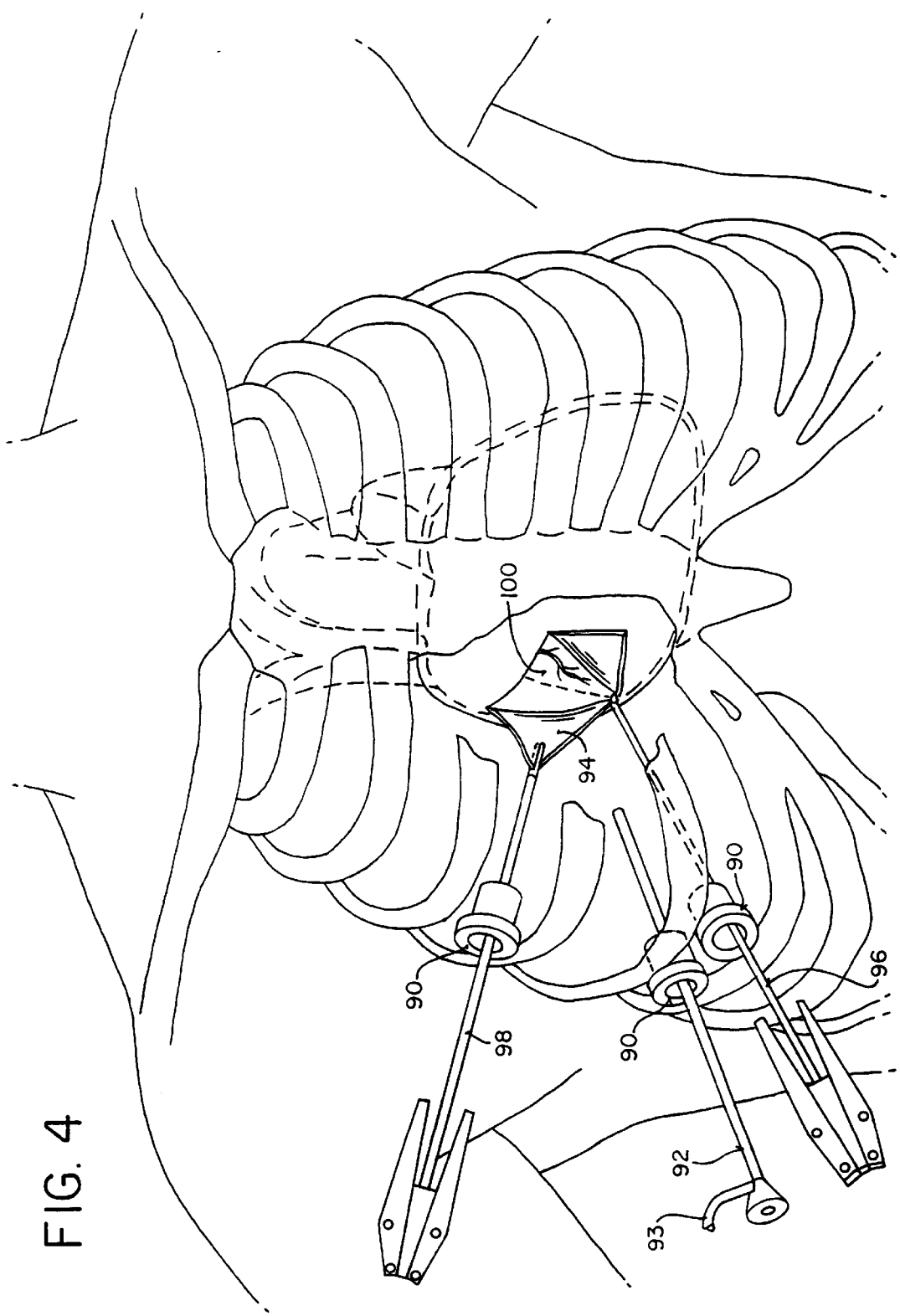
FIG. 4 is a front cut-away view of a patient's chest showing cutting the pericardium to expose the heart according to the method of the invention.

Referring to FIG. 4, in order to gain access to the heart, an opening is made in the pericardium 94 using thoracoscopic instruments introduced through access ports 90, including thoracoscopic scissors 96 and thoracoscopic forceps 98. Instruments suitable for use in this procedure are described in copending application Ser. No. 08/194,946, filed Feb. 11, 1994, now U.S. Pat. No. 5,501,698, which is incorporated herein by reference. An opening approximately 2 cm–8 cm square is formed in the pericardium, exposing the exterior of the heart 100.

Figure 5:
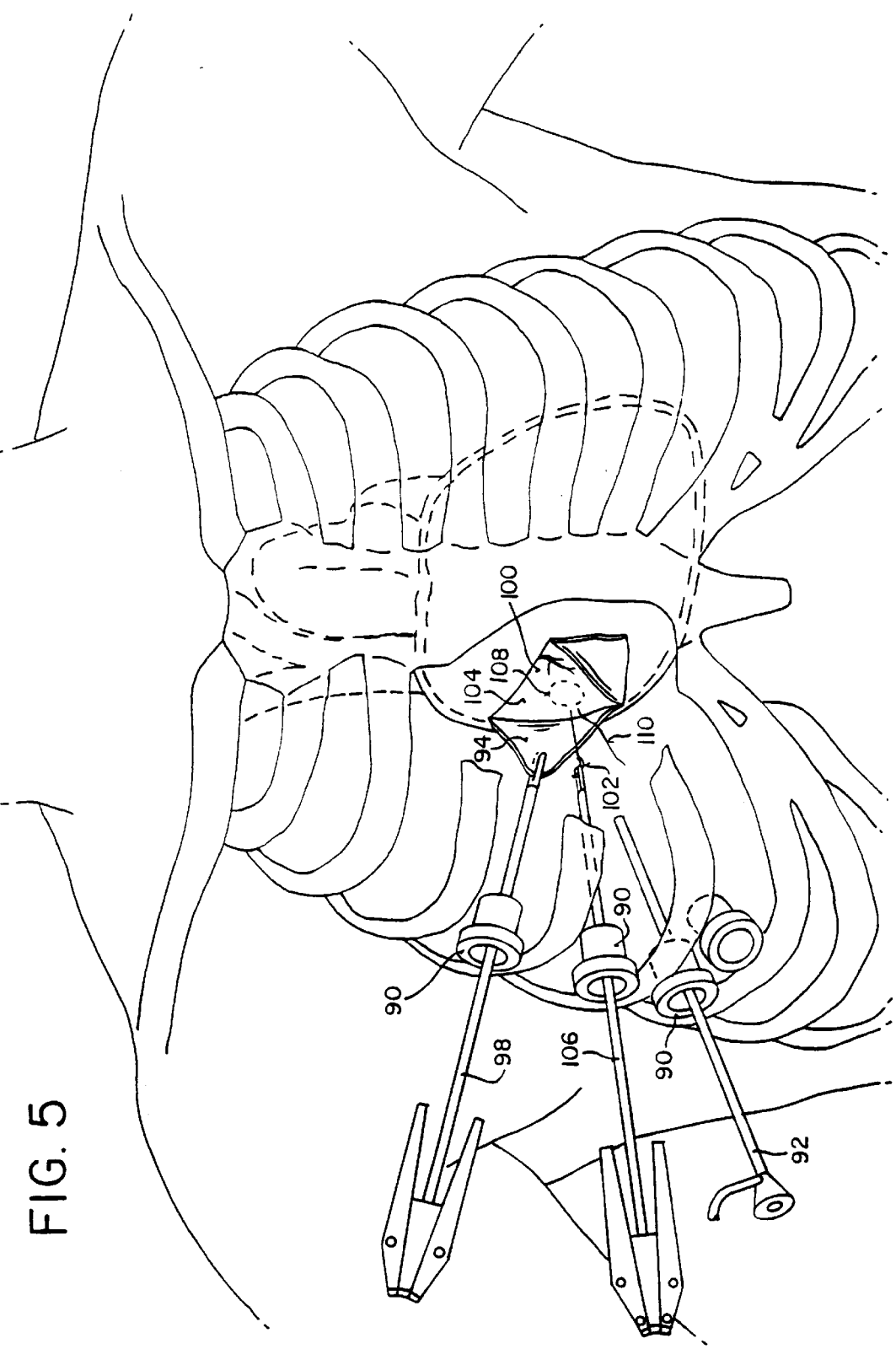
FIG. 5 is a front cut-away view of a patient's chest showing the placement of a pursestring suture in a muscular wall of the heart according to the method of the invention.
Figure 6:
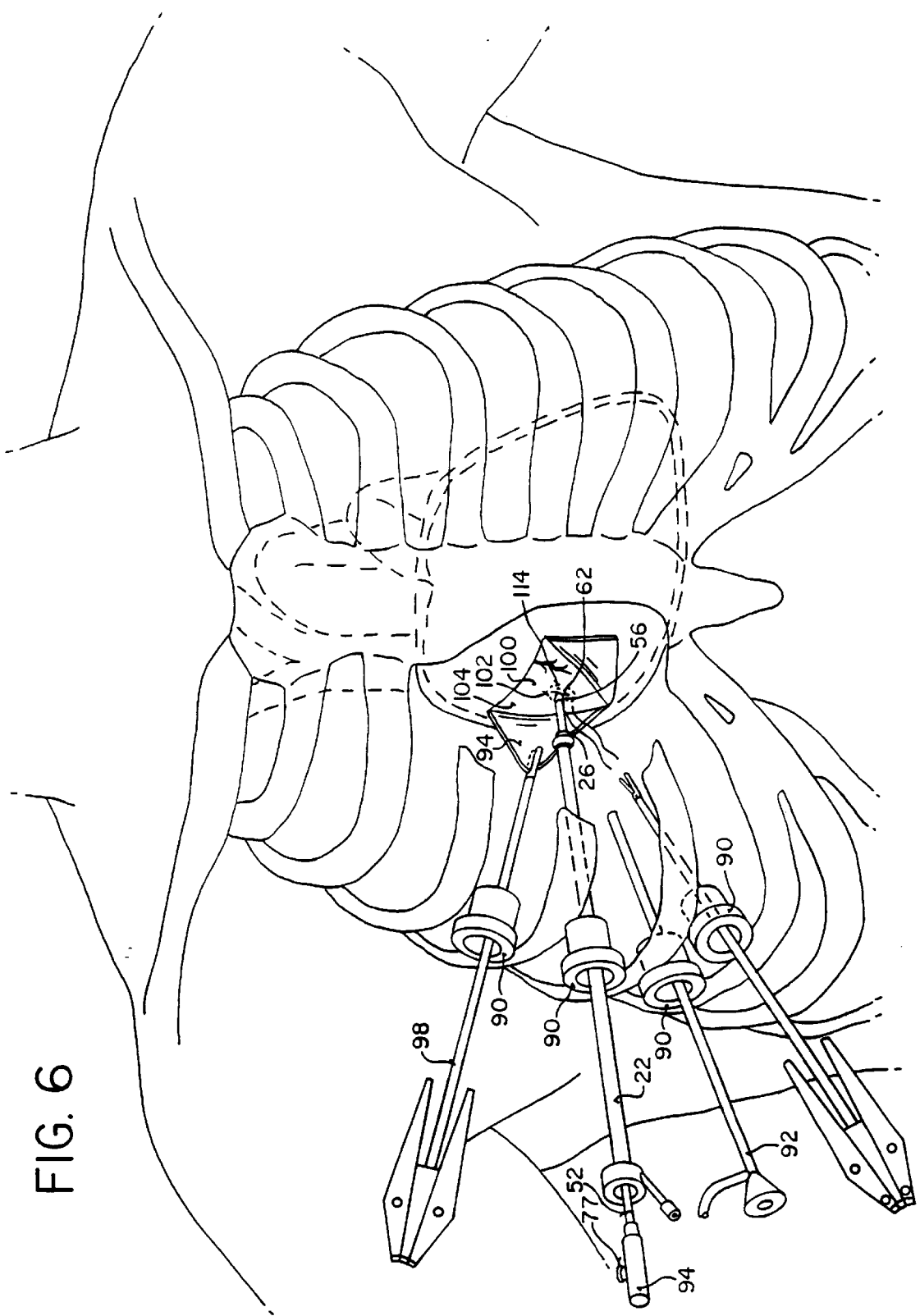
FIG. 6 is a front cut-away view of a patient's chest showing the penetration of the muscular wall of the heart according the method of the invention.

As shown in FIG. 5, a purse string suture 102 is then placed in the wall 104 of heart 100 around the site at which it is desired to introduce access device 22. This is accomplished by using thoracoscopic needle drivers 106 to introduce into the chest cavity a curved suture needle 108 attached to one end of a suture thread 110, and to drive the needle through the heart wall to form a running stitch in a circular pattern approximately 12–14 mm in diameter. A double-armed suture may also be used, wherein the suture thread 110 has needles at both ends, allowing each needle to be used to form one semi-circular portion of the purse-string. Suture thread 110 may be long enough to allow both ends of the suture to be drawn outside of the chest cavity once purse-string suture 102 has been placed, or it may be shorter and manipulated within the chest cavity using thoracoscopic instruments. Suture needle 108 is then cut from thread 110 using thoracoscopic scissors.

Access device 22 may now be introduced into heart 100. In some cases, it may be advantageous to first place the patient on cardiopulmonary bypass and to place the heart under cardioplegic arrest before introducing access device 22. Preferably, however, heart 100 remains beating during the procedure to avoid the trauma and risks associated with cardioplegic arrest. Obturator 52 is positioned within inner lumen 30 of access device 22 so that distal end 56 of the obturator is exposed distally of distal end 26 of the access device. Access device 22 with obturator 52 positioned therein is introduced through an access port 90 into the chest cavity, and distal end 56 of the obturator is positioned against heart wall 104 centrally within the bounds of purse-string suture 102. Button 77 on handle 94 of the obturator is then pressed downward and distally so as to extend blade 62 from distal end 56, causing blade 62 to penetrate through heart wall 104. A thoracoscopic grasping instrument (not shown) may be used to grasp the heart wall near purse string suture 102 to counter the insertion force of blade 62 and access device 22. As blade 62 penetrates the heart wall, access device 22 is advanced distally in conjunction with obturator 52 so that both devices extend into the heart through the penetration 114 formed in heart wall 104.

Figure 7:
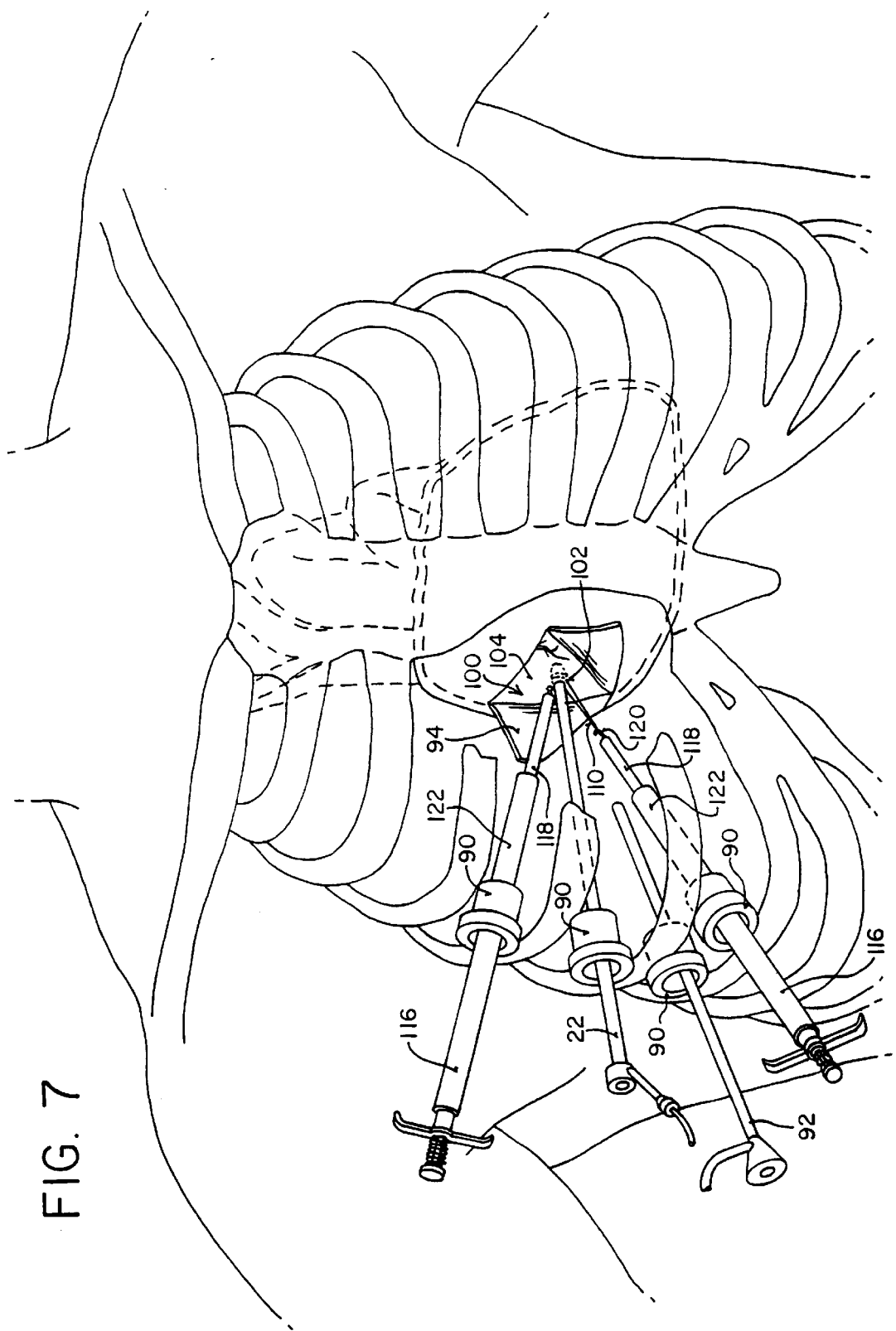
FIG. 7 is a front cut-away view of a patient's chest showing the position of the access device of FIG. 1 through the penetration in the muscular wall of the heart according to the method of the invention.

Once distal end 26 of access device 22, including balloon 32 or flange 44 if used, is within the interior of heart 100, purse-string suture 102 is cinched tightly to form a hemostatic seal around access device 22, as shown in FIG. 7. One or a pair of thoracoscopic cinching devices 116 may be used for this purpose. Each cinching device 116 comprises a shaft 118 with a slidable hook 120 at its distal end which can be used to grasp a loop of purse-string suture 102. Hook 120 may retracted proximally to frictionally retain suture thread 110 against the distal end of shaft 118. Loops on opposing sides of purse-string suture 102 may be grasped in this manner, and cinching devices 116 then withdrawn proximally to cinch purse-string suture 102 tightly, thereby gathering heart wall tissue against the exterior of access cannula 22 to form a hemostatic seal. Cinching devices 116 may be clamped in position to maintain tension on suture thread 110. Alternatively, a slidable sleeve 122 may be provided around shaft 118. Once a suture loop has been secured in hook 120, slidable sleeve 122 may be slid distally relative to shaft 118 until it abuts against the surface of heart wall 104. Shaft 118 is then pulled proximally relative to sleeve 122 to obtain the desired degree of tension on suture thread 110. Sleeve 122 is configured to frictionally retain shaft 118 in position to maintain tension on the suture.

Figure 8A:
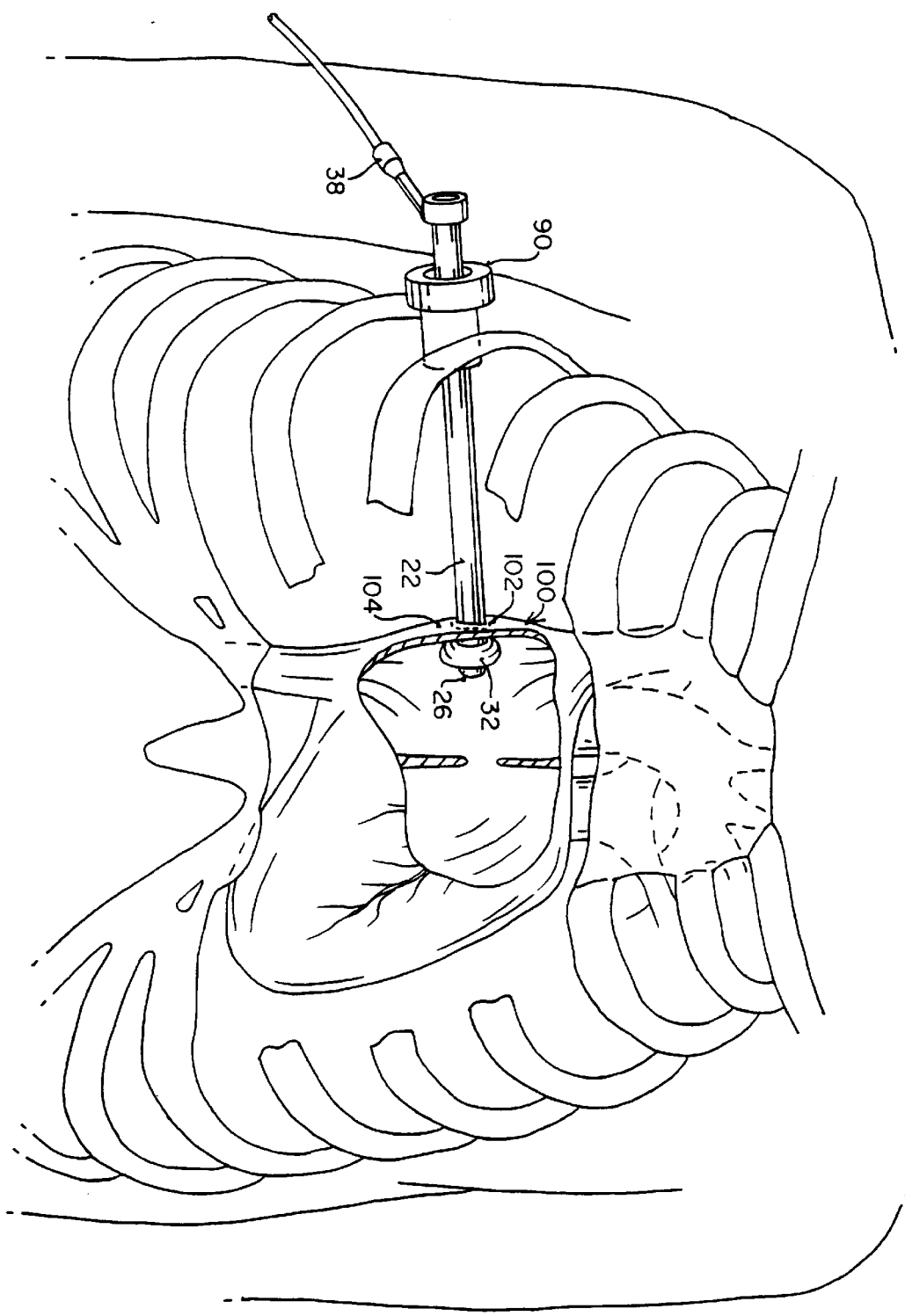
FIG. 8A is a front cut-away view of a patient's chest showing the position of the access device of FIG. 1 through the penetration in the muscular wall of the heart with a balloon-type sealing means expanded according to the method of the invention.

If a balloon or radially-expanding portion of access device 22 is used to enhance hemostasis, it is now activated. The use of a balloon 32, described above in reference to FIG. 2B, is illustrated in FIG. 8A. Once distal end 26 of access device 22 is introduced into the interior of heart 100, balloon 32 is inflated by introducing an inflation fluid such as saline through inflation lumen 34 (FIG. 1). A syringe or other commercially-available inflation device connected to inflation port 38 may be used for this purpose.

Obturator 52 is then withdrawn from inner lumen 30 of access device 22. As described above, access device 22 is preferably positioned in a vertical orientation so that outflow of blood from the heart through inner lumen 30 is prevented by gravity—that is, the pressure head of blood within inner lumen 30 is equal to that in the cardiac chamber. In other cases, a hemostasis valve (not shown) is provided within inner lumen 30 to prevent blood flow from the heart, while allowing instruments to be introduced through the access device.

The patient has now been prepared for a diagnostic or treatment procedure to be carried out within heart 100 through access device 22. Advantageously, the need for gross thoracotomy, cardiopulmonary bypass and cardioplegic arrest have been avoided, while providing a relatively large, straight, and hemostatically-sealed access passage directly into the interior of the heart.

Visualization within the heart may be accomplished in any of several ways. Transesophageal echocardiography may be used, wherein an ultrasonic probe is placed in the patient's esophagus or stomach to ultrasonically image the interior of the heart. An ultrasonic probe may also be placed through one of access ports 90 into the chest cavity and adjacent the exterior of the heart for ultrasonically imaging the interior of the heart.

Figure 8B:
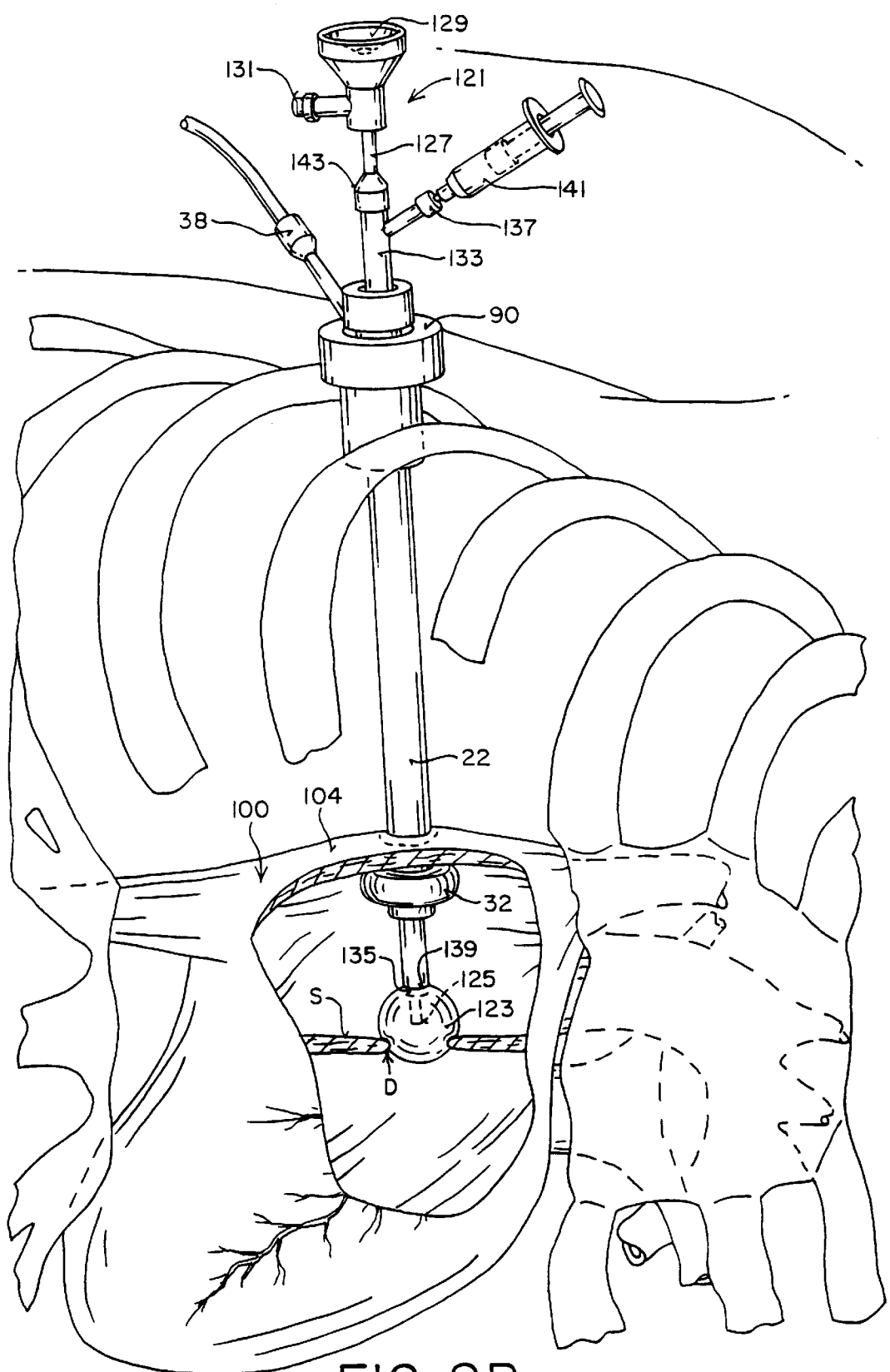
FIG. 8B is a front cut-away view of a patient's chest showing the use of an endoscope having a balloon over its distal end in a method of visualizing the interior of the heart according to the invention.

Alternatively, as illustrated in FIG. 8B, an endoscope 121 having an optically transparent bulb such as an inflatable balloon 123 over its distal end 125 may be introduced through access device 22 into the interior of the heart. Balloon 123 may be inflated with a transparent inflation fluid such as saline to displace blood away from distal end 125 and may be positioned against a site such as septal defect D in septum S, allowing the location, shape, and size of defect D to be visualized. In one embodiment, endoscope 121 is a conventional, commercially-available endoscope such as a V. Mueller Model No. LA 7005 (V. Mueller, Inc, Deerfield, Ill.), having a tubular shaft 127 in which one or more lenses (not shown) are mounted, an eyepiece 129 at its proximal end for looking through tubular shaft 127, and a connector 131 for connection to a light source which transmits light through optical fibers (not shown) extending through tubular shaft 127 to distal end 125. Endoscope 121 is slidably positioned in an outer sleeve 133 having a distal end 135 to which balloon 123 is attached. Outer sleeve 133 has a luer connection 137 on its proximal end in communication with an inflation lumen (not shown) extending through outer sleeve 133 to an outlet port 139 at distal end 135 within the interior of balloon 123. Luer connection 137 is adapted for connection to a syringe 141 for injecting a transparent inflation fluid such as saline into balloon 123 for inflation thereof. A tubular, compliant seal 143 is attached to a proximal end of outer sleeve 133 to provide a fluid-tight seal between endoscope 121 and outer sleeve 133. It will be understood to those of skill in the art that, instead of using separate outer sleeve 133, balloon 123 could be mounted directly to distal end 125 of endoscope 121 and an inflation lumen provided in shaft 127 for inflation of the balloon.

In use, endoscope 121 is positioned in outer sleeve 133 outside of the patient, and the two are together introduced through inner lumen 30 of access device 22 with balloon 123 evacuated of fluid in a collapsed configuration. Once balloon 123 is within the heart, saline is injected into balloon 123 to inflate the balloon to a diameter of approximately 2–6 cm. Balloon 123 is then positioned against the site to be visualized, e.g., septum S around defect D. The size and location of the defect D may then be visualized by looking through eyepiece 129. Additionally, endoscope 121 may include a video camera mount to allow video imaging and remote viewing of the interior of the heart on a video monitor.

Instead of a balloon or bulb over distal end 125, saline may be injected under pressure through a lumen in endoscope 121 or in outer sleeve 133 and out of a port at or near distal end 125 to displace blood away from the distal end to provide a transparent field of view.

As a further visualization alternative, an endoscope may be utilized which employs a specialized light filter, so that only those wavelengths of light not absorbed by blood are transmitted into the heart. The endoscope utilizes a CCD chip designed to receive and react to such light wavelengths and transmit the image received to a video monitor. In this way, the endoscope can be positioned in the heart through access device 22 and used to see through blood to observe a region of the heart. A visualization system based on such principles is described in U.S. Pat. No. 4,786,155, which is incorporated herein by reference.

In still another alternative for visualization, particularly useful in imaging an atrial or ventricular septal defect, a very small-profile light source such as an optical fiber is positioned in the left atrium or left ventricle, opposite the right atrium or right ventricle in which access device 22 is positioned. The light source may be introduced through access device 22 and through the septal defect into the left side of the heart, or it may be introduced through a minute puncture in the left side of the heart. The puncture may be closed by a purse-string suture if needed. An endoscope is then positioned through access device 22 into the right side of the heart opposite the light source. The endoscope utilizes a CCD chip designed to receive and react to those light wavelengths transmitted through blood, as well as any light wavelengths transmitted through the interatrial or interventricular septum. This produces a shadow-like image of the septal defect, which is received by the CCD and displayed on a video monitor, thereby imaging the size, shape and location of the septal defect.

With access device 22 in position in the heart and a means of visualization in place, a number of intracardiac procedures may be performed. One such procedure is the repair of atrial septal defects, which will now be described with reference to FIGS. 9–32.

FIGS. 9–20 illustrate an exemplary embodiment of a system and method for repairing an atrial septal defect according to the invention. In these Figures, an umbrella-type septal defect repair patch is shown which is similar to that that described in U.S. Pat. No. 3,874,388 to King, which is incorporated herein by reference. It should be understood, however, that any of a number of different septal defect repair patches may be utilized in conjunction with the system and method of the invention without departing from the principles thereof. Some of the septal defect repair patches which could be utilized are described, for example, in U.S. Pat. Nos. 4,007,743, 5,334,217, 4,917,089, 5,284,488, and 5,108,420, which are incorporated herein by reference. Another septal defect repair patch which could be used with the present invention is disclosed in PCT application No. PCT/US92/10141 to Pavcnik, published Jun. 10, 1993.

Figure 9:
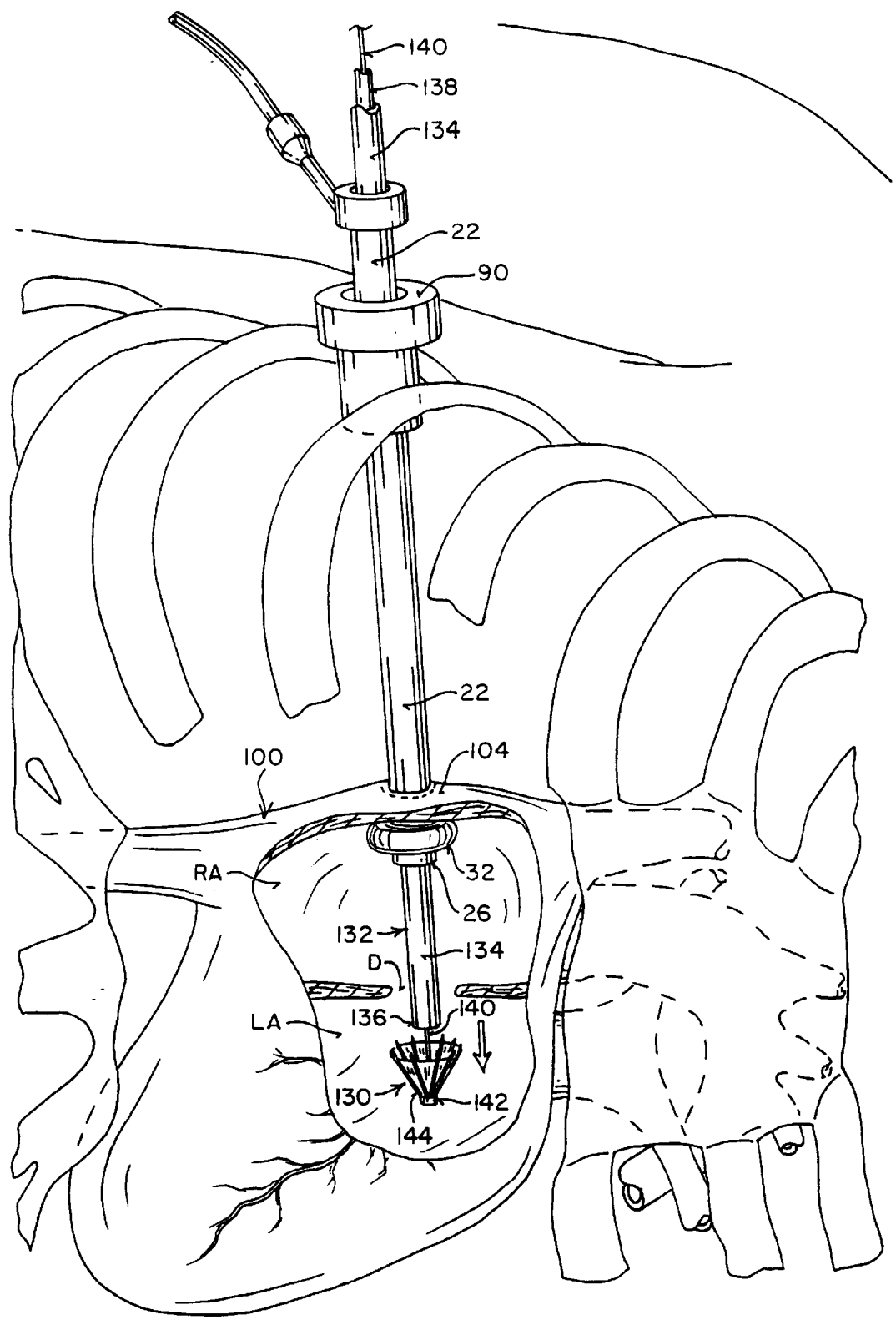
FIG. 9 is a front cut-away view of a patient's chest showing the deployment of a distal patch of a septal defect repair device in a chamber of the heart according to the method of the invention.

As shown in FIG. 9, the septal defect repair system of the invention includes, in addition to access device 22 described above, a defect repair device 130 and a delivery means 132. Defect repair device 130 comprises, in this embodiment, a double umbrella-type patch similar to that described in the '388 patent to King. Delivery means 132 comprises a tubular delivery shaft 134 having a distal end 136 positionable through inner lumen 30 of access device 22, and a proximal end (not illustrated in FIG. 9) which is used to manipulate delivery means 132 from outside of the chest cavity. An outer tubular control rod 138 is slidably disposed within delivery shaft 134, and an inner control rod 140 is slidably disposed within outer control rod 138. Inner control rod 140 has a distal end 142 detachably coupled to a distal patch 144 of defect repair device 130.

Preferably, delivery shaft 134 is generally straight and rigid to facilitate introduction through access device 22 and manipulation of delivery means 132 from its proximal end. Delivery shaft 134 is thus stainless steel, titanium, another biocompatible metal, or a biocompatible polymer with a minimum durometer of 75 Shore A. Outer control rod 138 and inner control rod 140 are preferably also a rigid material such as stainless steel or titanium, although some flexibility may be tolerated in these members since they are supported exteriorly by delivery shaft 134, so long as the inner and outer control rods have sufficient column strength to perform their respective functions, as described below.

The details of an exemplary embodiment of defect repair device 130 are illustrated in FIGS. 11, 12A–12B, 13 and 14A–14B, which show a double-umbrella device similar to that disclosed in the King patent. FIG. 11 illustrates distal patch 144, which includes a central hub 146 to which a plurality, e.g. six, radially-extending struts 148 are coupled. Hub 146 and struts 148 are a rigid material such as stainless steel or a biocompatible polymer. Struts 148 include sharpened points 149 pointing generally perpendicular to the struts at their outer ends for penetrating the cardiac septum. A biocompatible flexible fabric 150 of a polyester such as Dacron™, an expanded polytetrafluoroethylene such as Gore-Tex® (W. L. Gore and Assoc., Inc.), silk, nylon, silastic, a portion of the patient's pericardium, or other biocompatible flexible material impervious to blood is attached to hub 146 by a keeper 152 and to struts 148 by sutures 154.

As shown in FIGS. 11A–11B, struts 148 may be hingedly coupled to hub 146 by means of a hinge ring 156 which extends through an eyelet 158 at the end of each strut. Hinge ring 156 and struts 148 are retained on hub 146 by keeper 152. Alternatively, struts 148 may be a resilient, flexible material and rigidly coupled to hub 146 so as to naturally assume a radially expanded configuration when unrestrained. A plurality of axial grooves 159 are provided on hub 146 to receive struts 148 when collapsed inward. Hub 146 further includes a threaded hole 160 on its proximal end into which the threaded distal end of inner control rod 140 may be threaded. A circumferential flange 162 is disposed about the proximal end of hub 146 for attachment to the proximal patch of the defect repair device, as described below.

Referring to FIGS. 12 and 13A–13B, defect repair device 130 further includes a proximal patch 164 having a construction much like distal patch 144. A plurality of struts 166 are hingedly coupled to a central hub 168 by means of a hinge ring 170 extending through eyelets 172 in the inner ends of the struts. Each strut 166 has an inwardly extending point 174 at its outer end for engaging the cardiac septum. A flexible fabric membrane 176 is attached to hub 168 by a keeper 180 and to struts 166 by sutures 182. Additional suture loops 184 are attached to struts 166 to allow attachment of tie wires for deployment of proximal patch 164, as described below.

As shown in FIGS. 13A–13B, hub 168 has a plurality of axial grooves 186 for receiving struts 166 in a collapsed configuration. Hub 168 also has an axial passage 188 of sufficient diameter to allow inner control rod 140 to extend slidably through it with minimal friction. On its distal end, hub 168 has a cavity 190 having an annular groove 192 for receiving circumferential flange 162 of hub 146 in a snap-fit relationship.

Figure 14:
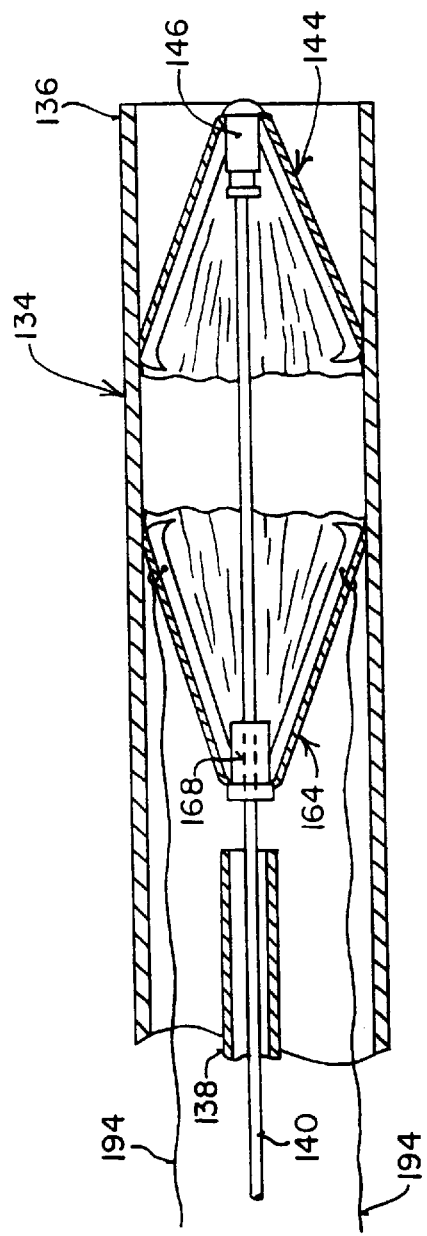
FIG. 14 is a side cross-sectional view of the septal defect repair device of FIGS. 10–13 positioned in a lumen of a delivery shaft according to the method of the invention.

Referring to FIG. 14, during introduction through access device 22, distal patch 144 and proximal patch 64 are preferably positioned in a collapsed configuration within delivery shaft 134 near distal end 136. Inner control rod 140 is positioned slidably through outer control rod 138, through axial passage 188 in hub 168 of proximal patch 164, and threaded into hole 160 in distal patch 144. Tie wires 194 are attached to suture loops 184 and extend proximally through delivery shaft 134 out of the chest cavity. As shown in FIG. 9, delivery shaft 134 is introduced through the right atrium RA and into the left atrium LA through septal defect D. Inner control rod 140 is then advanced distally relative to delivery shaft 134 to deploy distal patch 144 out of delivery shaft 134 into left atrium LA.

Figure 15:
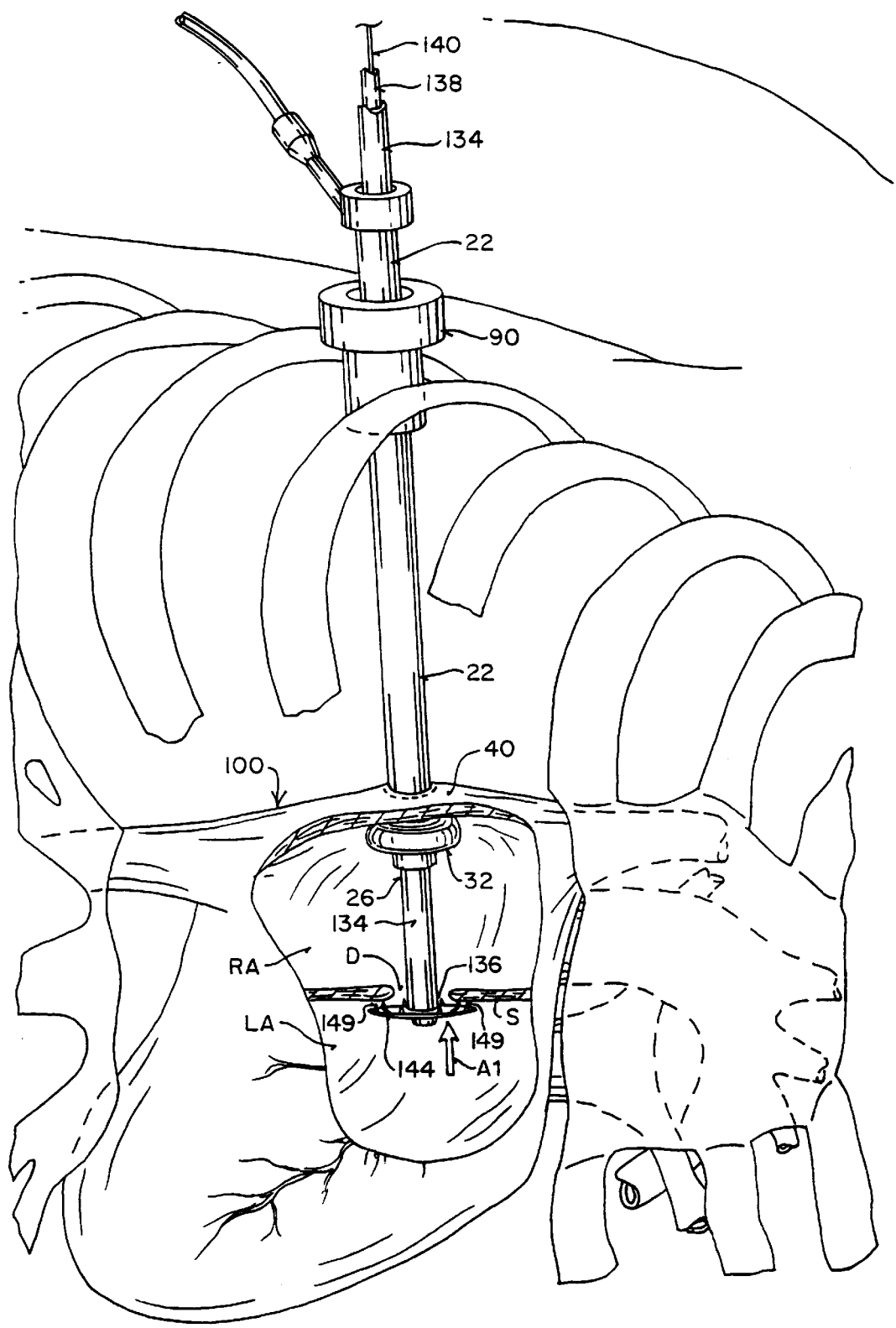
FIG. 15 is a front cut-away view of a patient's chest showing the expansion of the distal patch of FIG. 10 in the left side of the heart according to the method of the invention.

As illustrated in FIG. 15, with distal patch 144 deployed in the left atrium, inner control rod 140 is pulled proximally relative to delivery shaft 134 until distal end 136 of the delivery shaft engages struts 148 (not shown in FIG. 15), urging struts 148 outward to a radially expanded position in which distal patch 144 is generally disk-shaped and parallel to cardiac septum S. Delivery shaft 134 and control rod 140 are then pulled proximally in the direction of arrow A1 until distal patch 144 engages septum S and points 149 of struts 148 partially penetrate septum S. This is done under visualization by TEE or one of the other techniques described above in order to ensure proper positioning of distal patch 144 so as to fully block blood flow across defect D. If, after initial placement, shunting of blood is detected across the defect, distal patch 144 may be repositioned by advancing delivery shaft 134 distally to disengage patch 144 from septum S, then manipulating delivery shaft 134 to position distal patch 144 in the desired location. The straightness, rigidity, and relatively short length of delivery shaft 134 provide the user a high degree of control and precision in placing the patch in the best possible position on septum S.

In some cases it may be desirable to have the capacity to re-collapse distal patch 144 and replace it within delivery shaft 134 for repositioning or removal from the patient. In such cases, tie wires may be provided which are coupled to the inner sides of struts 148 and extend through delivery shaft 134 out of the chest cavity. By tensioning the tie wires, struts 148 may be urged back into a collapsed position and distal patch 144 then pulled back into delivery shaft 134.

Figure 16:
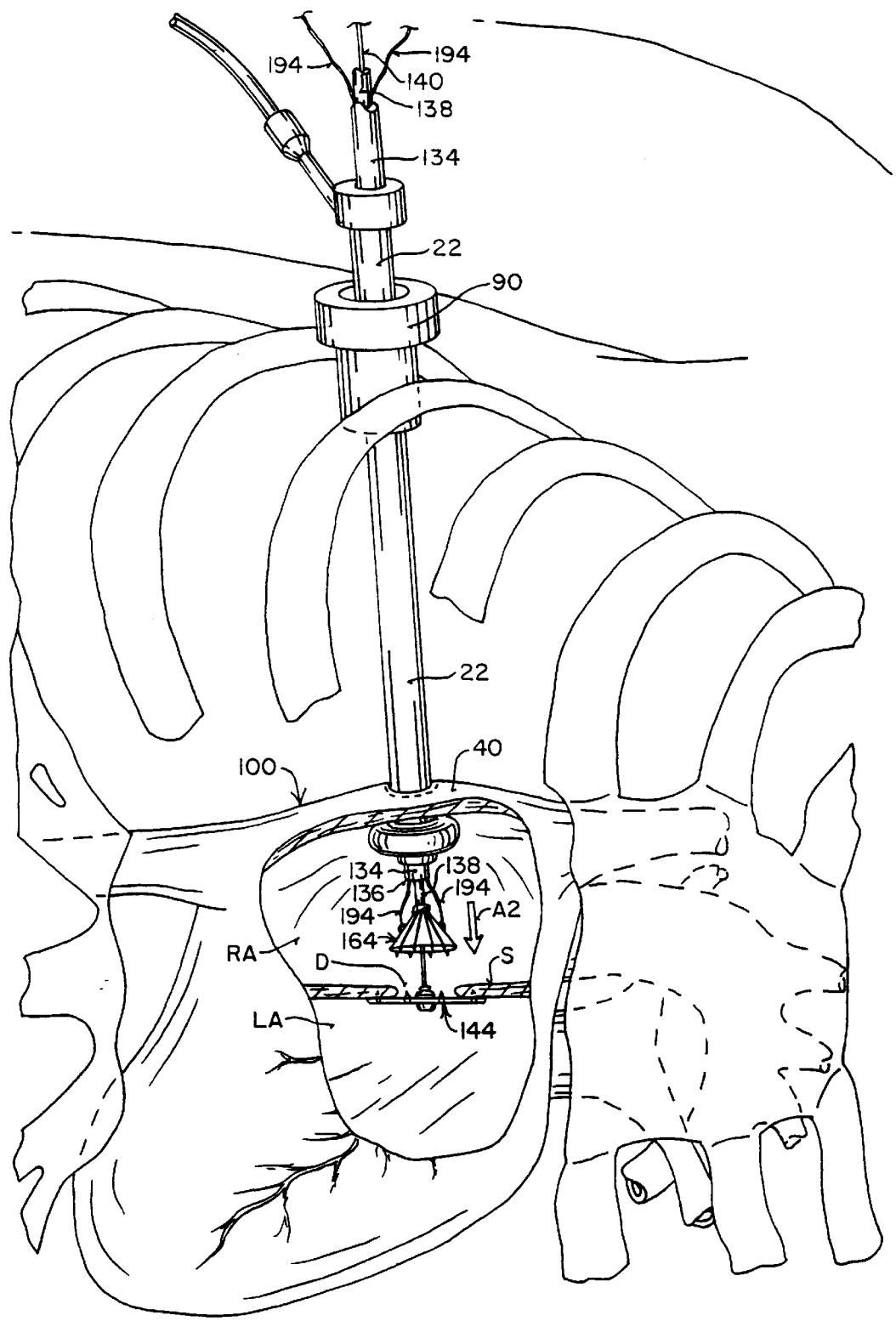
FIG. 16 is a front cut-away view of a patient's chest showing the deployment of the proximal patch of FIG. 12 in the right side of the heart according to the method of the invention.

With distal patch 144 anchored in septum S, proximal patch 164 is next deployed in the right atrium RA, as illustrated in FIG. 16. This is accomplished by pulling delivery shaft 134 proximally to provide some space between its distal end 136 and septum S. Outer control rod 138 is then advanced distally relative to delivery shaft 134 to deploy proximal patch 164 out of delivery shaft 134 in the direction of arrow A2. Proximal patch 164 and outer control rod 138 slide relative to inner control rod 140, which is maintained in tension to keep distal patch 144 against septum S.

Figure 17:
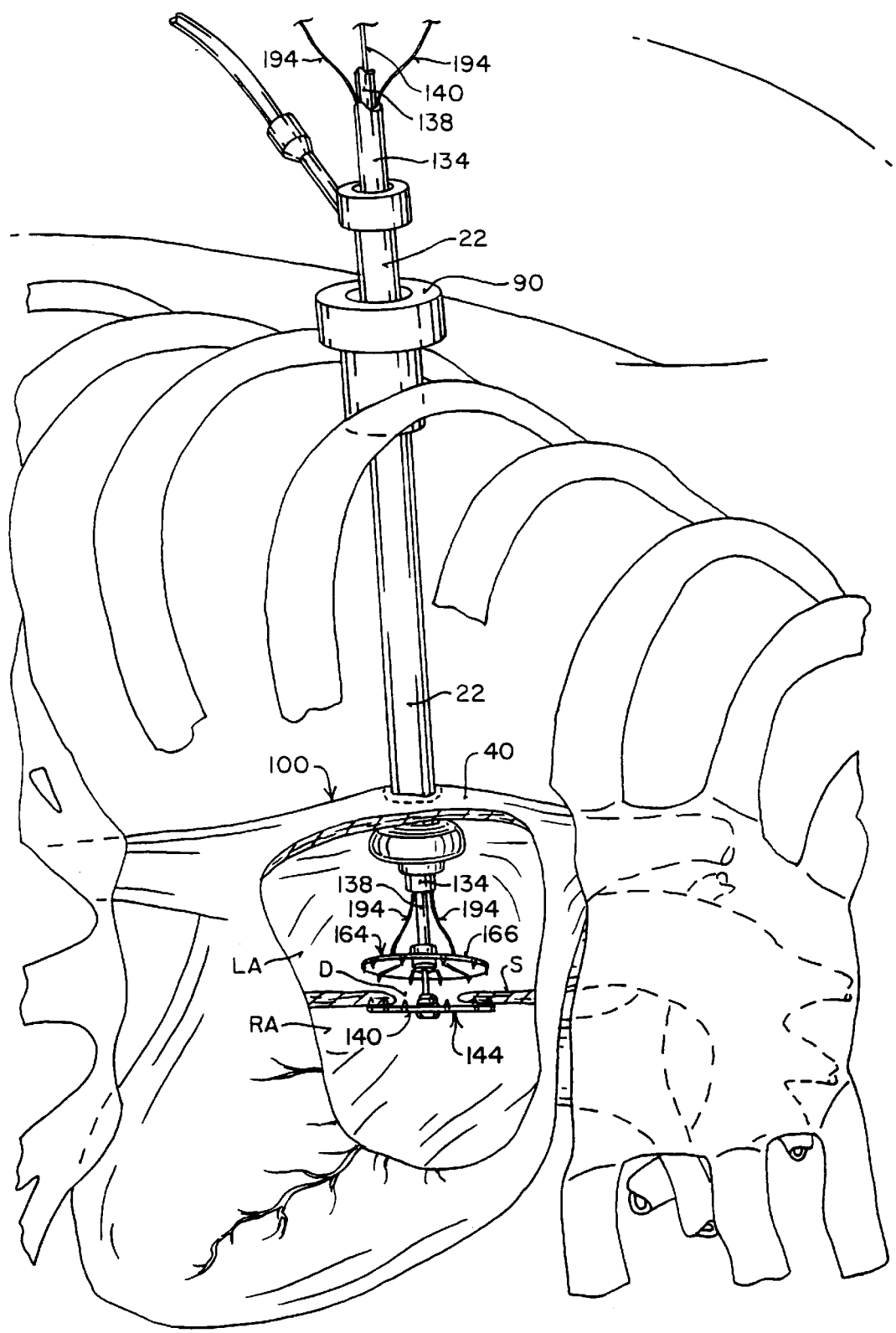
FIG. 17 is a front cut-away view of a patient's chest showing the expansion of the proximal patch of FIG. 12 in the right side of the heart according to the method of the invention.
Figure 18:
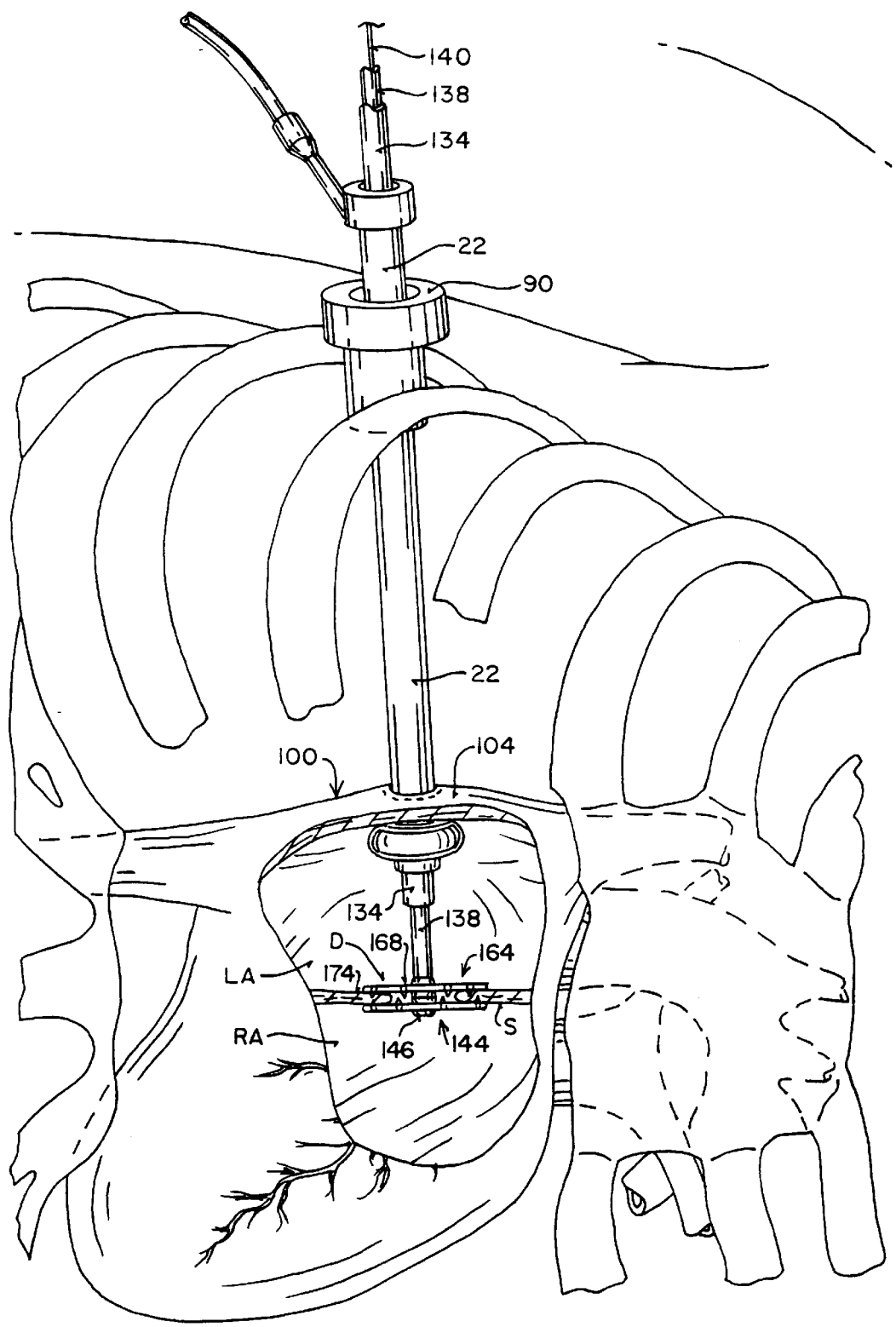
FIG. 18 is a front cut-away view of a patient's chest showing the attachment of the proximal patch to the distal patch to repair the septal defect according to the method of the invention.

As shown in FIG. 17, tie wires 194 are then tensioned so as to urge struts 166 outward into a radially expanded position in which proximal patch 164 is generally disk-shaped and parallel to septum S. As illustrated in FIG. 18, outer control rod 138 and proximal patch 164 are then advanced distally over inner control rod 140 until hub 168 of the proximal patch engages and snaps into hub 146 of distal patch 144. Points 174 on the ends of struts 166 partially penetrate septum S to anchor the patch in position. Tie lines 194 are removed from proximal patch 164, by, for example, cutting the tie lines with a cutting instrument introduced through access device 22 after removal of delivery shaft 134. Alternatively, tie lines 194 may be looped through suture loops 184 on proximal patch 164 so that both ends extend out of the chest cavity, in which case one end of each tie line is simply pulled through the suture loop to remove the tie line.

It will be understood to those of ordinary skill in the art that a variety of different types of actuators of well-known construction may be employed at the proximal end of delivery means 132 to allow the user to selectively deploy defect repair device 130 in the heart. In one embodiment, not pictured, a handle is fixed to the proximal end of delivery shaft 134 which is suitable for being grasped in the user's hand. A pair of slidable buttons are mounted to the handle, one being coupled to the proximal end of the inner control rod 140 and the second being coupled to the proximal end of outer control rod 138. In this way, the user can independently deploy distal patch 144 and proximal patch 164 by sliding the respective buttons on the handle. A passage is also provided in the handle in communication with the interior of delivery shaft 134 to allow tie wires 194 to extend out of the delivery shaft outside of the patient's body.

Figure 19:
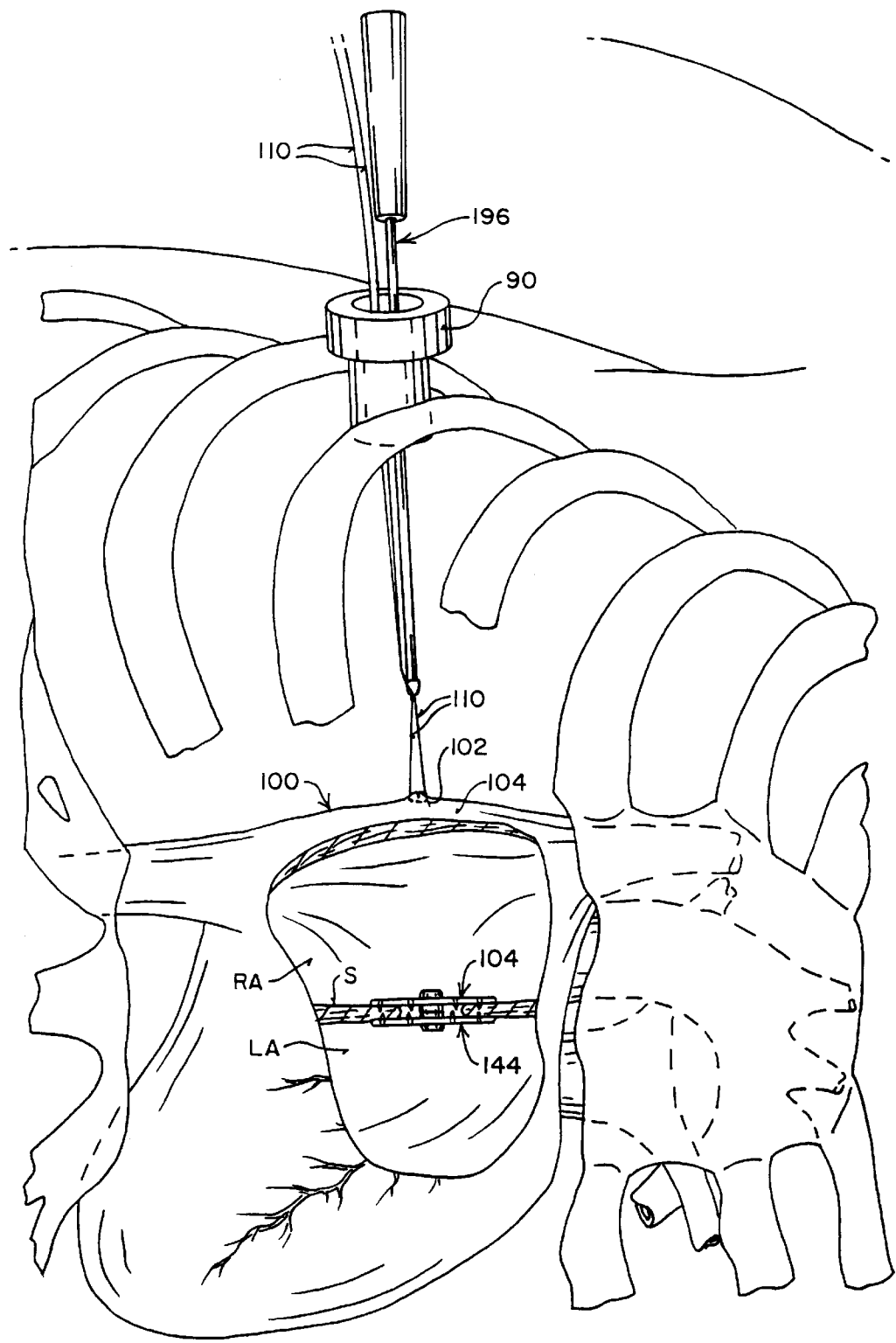
FIG. 19 is a front cut-away view of a patient's chest showing the closure of the penetration in the muscular wall of the heart according to the method of the invention.

Delivery shaft 134, along with inner control rod 140 and outer control rod 138, are then removed from the chest cavity through access device 22. If desired, the defect repair may be inspected by placing an endoscope with a transparent bulb or balloon over its distal end through access device 22 into right atrium RA. The bulb or balloon is positioned against septum S and/or proximal patch 164 to inspect the position of the patch and to determine whether the septal defect has been completely occluded. Shunting of blood may also be detected using TEE or other ultrasonic technique. If patch position is satisfactory, access device 22 may be removed from the patient. Balloon 32 (if used) is deflated, and access device 22 is withdrawn from the penetration in heart wall 104. As shown in FIG. 19, sutures 110 are pulled tight as access device 22 is withdrawn to close the penetration without significant loss of blood from the heart. Knots are tied in sutures 110, usually extracorporeally, and slid into the chest cavity and against heart wall 104 using an endoscopic knot pusher 196 introduced through access port 90. This may be done under visualization with an endoscope introduced through a separate access port 90 (not shown in FIG. 19). Sutures 110 are then trimmed off with a pair of endoscopic scissors.

Figure 20:
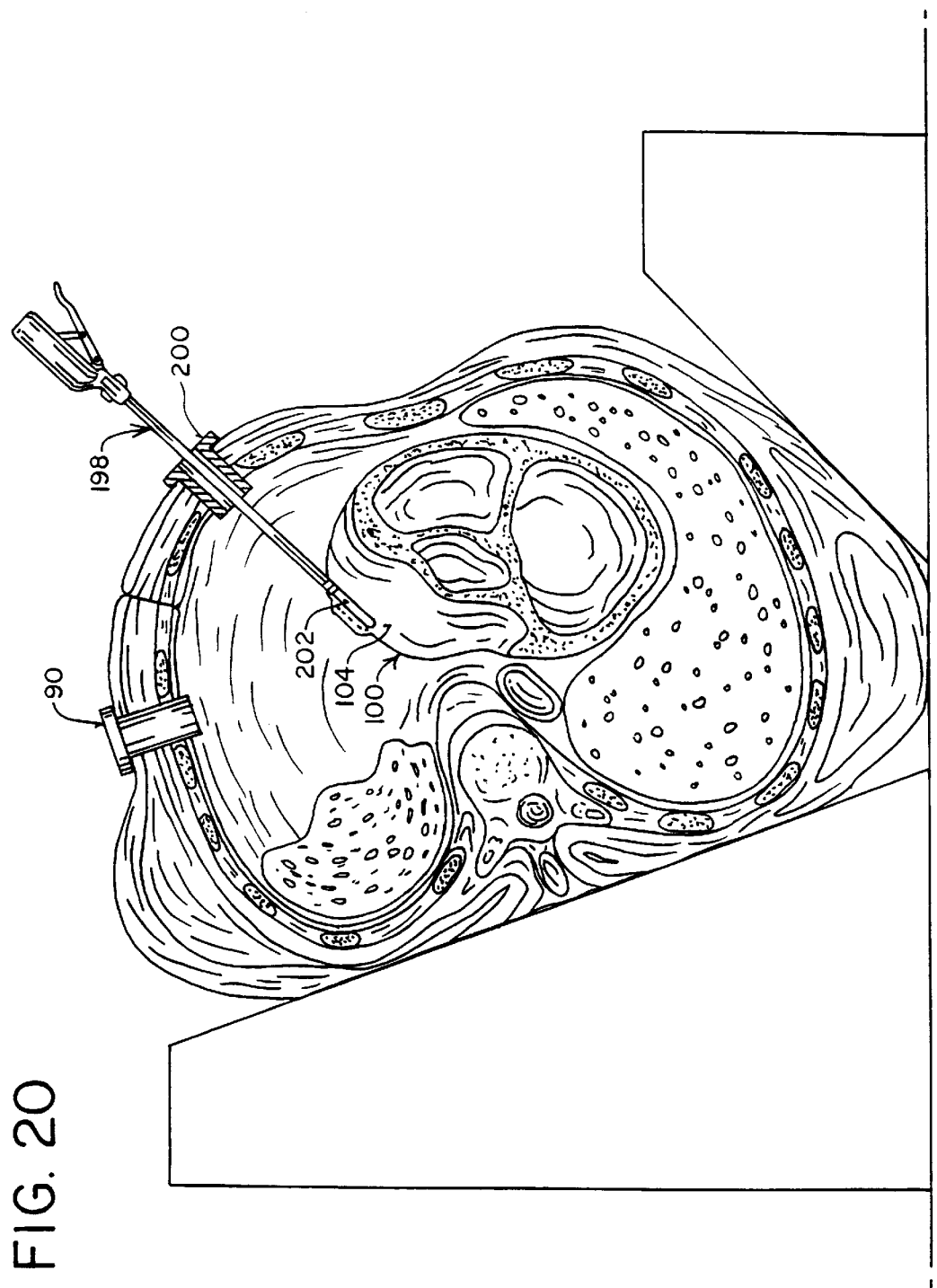
FIG. 20 is a transverse cross-sectional view of the patient's chest showing an alternative technique for closing the penetration in the muscular wall of the heart according to the method of the invention.

An alternative method of closing the penetration in the heart wall is illustrated in FIG. 20. In this technique, an endoscopic staple applier is used to apply one or more staples to the heart wall across the penetration. A staple applier such as, for example, an AutoSuture™ Powered Multifire Endo TA60 device available from United States Surgical Corp. of Norwalk, Conn., may be utilized. Under visualization using an endoscope positioned in an access port 90, stapler 198 is introduced through an access port 200 in the anterior wall of the patient's chest so that the anvils 202 are generally parallel to heart wall 104. The heart wall around the penetration is pursed up using endoscopic forceps so that anvils 202 can be positioned around a portion of the myocardium that includes the penetration. The stapler is then actuated, applying a row of staples through the heart wall across the penetration to seal it closed.

With the penetration in heart wall 104 closed, the procedure is completed by removing all access ports 90 and closing all percutaneous incisions. The right lung is re-inflated, the endotracheal tube is removed, and the patient is recovered from anesthesia.

Figure 23:
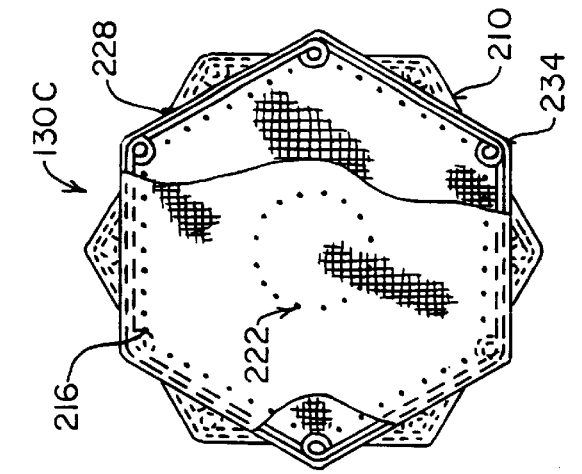
FIG. 21A, 22A, and 23 are top partial cut-away views of alternative embodiments of a septal defect repair device according to the principles of the invention.
Figure 21A:
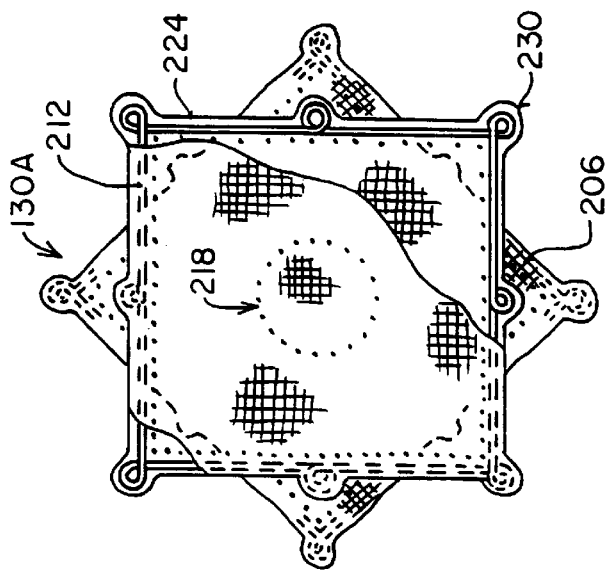
Figure 21B:
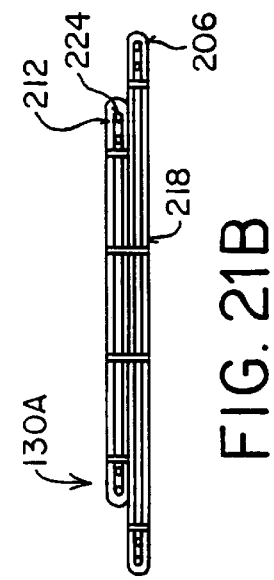

Additional embodiments of defect repair device 130 of the invention are illustrated in FIGS. 21A–21B, 22A–22B, 23, and 24A–24B. Defect repair devices 130A, 130B, 130C of FIGS. 21–23 each include a distal patch 206, 208, 210, and a proximal patch 212, 214, 216. The patches are a flexible, biocompatible, and blood impervious material, preferably conducive to endothelialization after implantation. Suitable materials include polyester mesh, knit fabrics of expanded polytetrafluoroethylene treated for low porosity, absorbable polyhydroxybutyrate, autologous pericardium, bovine or porcine pericardium, polyurethane and polypropylene mesh. The proximal and distal patches are attached together in a parallel relationship by an attachment means 218, 220, 222 forming a ring at the center of the patches. Attachment means 218 may comprise a single suture in a circular running stitch, a plurality of individual knotted suture loops, rivets, or other fasteners, or a circular series or continuous line of adhesive bonding or heat welding. A wire support frame 224, 226, 228 is attached around the outer edges of the distal and proximal patches, preferably by folding the outer edges of the patch around the frame and suturing or bonding the patch to itself, thereby enclosing the support frame within the patch material. On each patch, support frame 224, 226, 228 is preferably a single continuous wire of Nitinol™, a superelastic nickel-titanium alloy available from Raychem Corporation, titanium, or stainless steel. Support frame 224, 226, 228 includes a plurality of loops 230, 232, 234 formed in the plane of each patch to allow for longitudinal flexing and bending of the frame to facilitate collapsing the patches during introduction. The loops may be formed outwardly to lie outside of the periphery of each side of the frame as illustrated in FIG. 21A, or inwardly to lie within the periphery of the frame as illustrated in FIGS. 22 and 23.

Figure 22A:
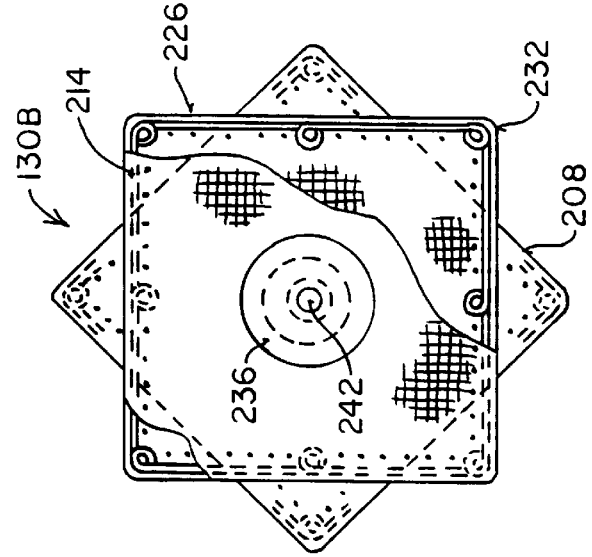
Figure 22B:
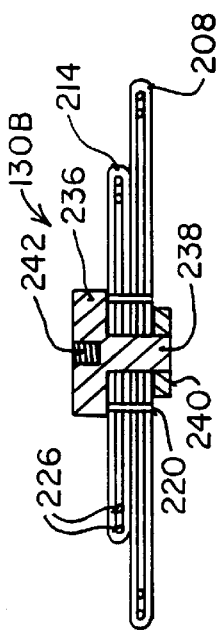
FIGS. 21B and 22B are side cross-sectional views of the septal defect repair devices of FIGS. 21A and 22A, respectively.

In the embodiment of FIGS. 22A–22B, defect repair device 130B includes a central hub 236 attached to distal and proximal patches 208, 214. Hub 236 has a post 238 extending through patches 208, 214, and a retainer 240 threaded or press-fit onto the distal end of post 238, thereby fixing hub 236 to the patches. Hub 236 also has a threaded hole 242 in its proximal end to which an introducer shaft may be threadably coupled. By allowing defect repair device 130 to be coupled to an introducer shaft via hub 236, the user is given a higher degree of control in positioning and repositioning the patch, as described more fully below. It should be understood that any of the embodiments in FIGS. 21A–21B and 23 may be provided with a hub like hub 236 of FIG. 22.

Patches 212, 214, 216 may have any of a variety of shapes including square or rectangular (FIGS. 21 and 22), hexagonal (FIG. 23), triangular, octagonal, pentagonal, circular, oval, or other shape. A defect repair device like those disclosed in U.S. Pat. No. 5,334,217 to Das, which is incorporated herein by reference, may also be utilized in conjunction with the present invention.

Figure 24A:
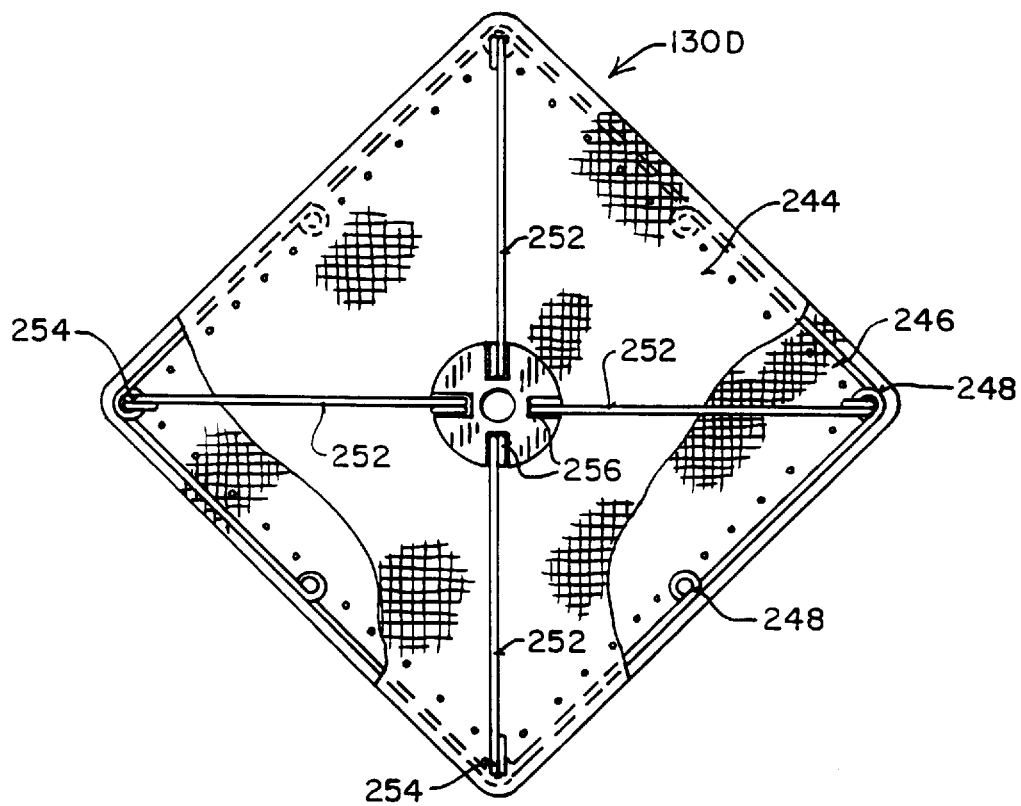
FIG. 24A is a top partial cut-away view of a further embodiment of a septal defect repair device according to the principles of the invention.
Figure 24B:
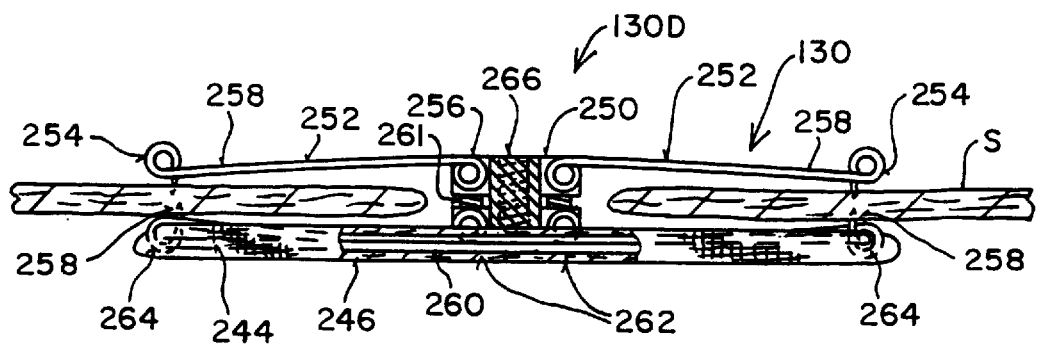
FIG. 24B is a side partial cut-away view of the septal defect repair device of FIG. 24A.

FIGS. 24A–24B illustrate still another embodiment of defect repair device 130. In this embodiment, defect repair device 130D has a distal patch 244 of a flexible, biocompatible material attached to a wire frame 246, much like distal patches 206, 208, 210 of FIGS. 21–23. Wire frame 246 may be continuous wire of stainless steel, Nitinol™, or other biocompatible, resilient metal or polymer, and may include a plurality of loops 248 like those shown in FIGS. 21–23. Rather than being attached to a proximal patch like the above-described embodiments, however, distal patch 244 of FIG. 24 is attached to a central hub 250, to which are coupled a plurality of radially-extending struts 252 on the proximal side of patch 244 and parallel thereto. While defect repair device 130D is pictured with four such struts in FIGS. 24A–24B, struts 252 may be between three and twelve in number. Struts 252 are Nitinol, stainless steel, or other flexible, resilient biocompatible metal or polymer, and are coupled to hub 250 in such a way that the outer ends 254 of struts 252 are biased toward patch 244 and deflectable away from patch 244 about an axis perpendicular to the central axis of hub 250. An additional patch (not shown) may be attached to struts 252 to provide patches on both sides of septum S, although in most cases, a single patch on the higher pressure side of the septum (the left side of the heart) is sufficient to prevent interatrial or interventricular blood flow through a septal defect.

In the embodiment shown, the inner ends 256 of struts 252 are formed in a loop which acts as a torsion spring to bias the struts toward patch 244. Alternatively, inner ends 256 may be straight and anchored directly to hub 250, wherein each strut 252 acts as a leaf spring biased toward patch 244. Optionally, distal struts 260 coupled to hub 250 may be provided adjacent to or attached to patch 244, distally and parallel to struts 252, so as to compressively engage septum S between the two sets of struts, as shown in FIG. 24B. In the embodiment shown, each of struts 252 is formed with one of distal struts 260 from a single continuous length of wire, with a first loop at the inner end 256 of each strut 252, and a second loop at the inner end 262 of each distal strut 260. A retainer 261, which may be a snap-ring, band, or loop of suture, retains struts 252 and distal struts 260 on hub 250. Struts 252, 260 may be round in cross-section, or rectangular so as to increase the moment of inertia in the transverse direction so that the struts tend to bend only about an axis perpendicular to the central axis of hub 250. Outer ends 254, 264 of struts 252 and distal struts 260 may include a sharp point 258 oriented generally perpendicular to the straight portion of the strut so as to partially penetrate septum S, as shown in FIG. 24B. Points 258 may alternatively be made long enough so that the points completely penetrate septum S, allowing visual inspection of strut deployment by observing emergence of each point on the opposite side of the septum. In one embodiment, outer ends 254 are formed in a 270° loop so that points 258 attain a perpendicular orientation. Hub 250 includes a threaded hole 266 which may be coupled to an introducer shaft.

Figure 25A:
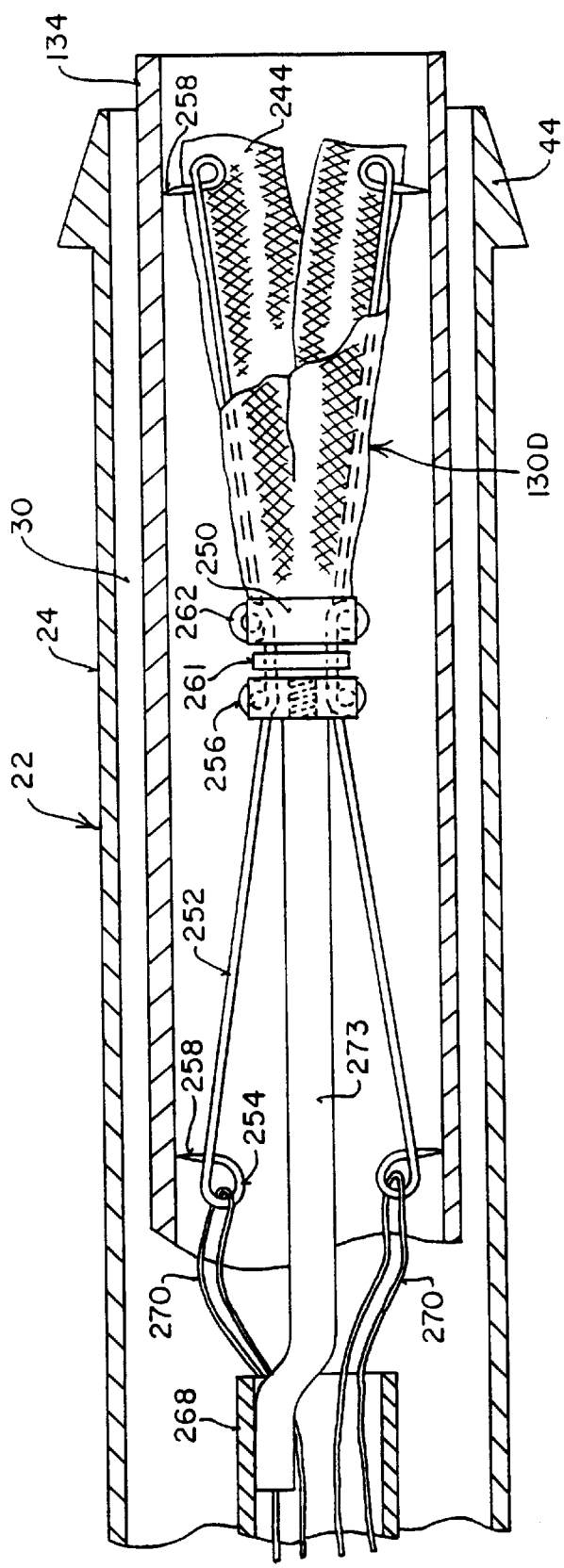
FIG. 25A is a side cut-away view of the septal defect repair device of FIGS. 24A–24B positioned in a collapsed configuration within a delivery shaft.

Defect repair device 130D of FIG. 24A is shown in FIG. 25A in a collapsed configuration within delivery shaft 134 for introduction into the heart through access device 22. Hub 250 is threadably mounted to a rod 273 attached to the end of an elongated tubular introducer shaft 268 to facilitate deployment of repair device 130D within the heart. Patch 244 and distal struts 260 are collapsed together distally of hub 250, while struts 252 are collapsed together proximally of hub 250. Spring loops at the inner ends 256, 262 of struts 252, 260 bias the struts outwardly against the inner wall of delivery shaft 134. A retraction wire 270, which may be a length of suture or wire, is attached to the outer end 254 of each strut 252 and extend through the interior of introducer shaft 268. After deployment of repair device 130D, retraction wires 270 may by used to retract the device back into delivery shaft 134 to reposition or remove the device. By tensioning retraction wires 270 from outside of the patient's body, struts 252 are re-collapsed and repair device 130 may be pulled back into delivery shaft 134. Preferably, retraction wires 270 are looped through outer ends 254 of the struts so that both ends of the retraction wires extend out of the body through delivery shaft 134. In this way, once repair device 130D is deployed satisfactorily, retraction wires 270 may be removed by simply pulling one end. Short lengths of suture or wire (not shown) may also be connected between outer ends 254 of adjacent pairs of struts 252, and a retraction wire 270 then looped through each short length. This configuration helps to maintain spacing between struts 252 and prevent tangling. Alternatively, a single retraction wire may extend through all of the loops at the outer ends of struts 252, with both ends of the single retraction wire extending out of the patient's body through delivery shaft 134.

Figure 25B:
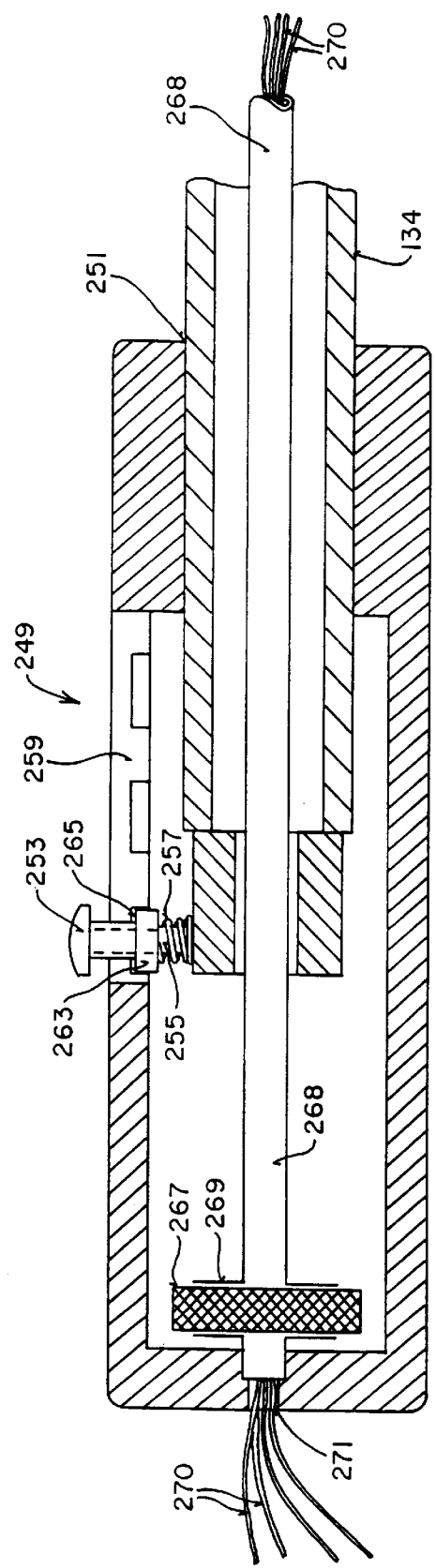
FIG. 25B is a side cut-away view of an actuator handle for deployment of the septal defect repair device of FIGS. 24–24B.

FIG. 25B illustrates an exemplary embodiment of an actuator handle 249 mounted to a proximal end of delivery shaft 134 for deploying repair device 130D. Delivery shaft 134 is slidably received within an axial bore 251 in a distal end of actuator handle 249. An actuator button 253 is slidably mounted to a post 255 attached to a proximal end of delivery shaft 134, and is biased outwardly by a spring 257. Button 253 extends through an axial channel 259 in actuator handle 249, and has an enlarged inner portion 263 which is slidably received within detents 265 at spaced-apart positions along channel 259. In this way, button 253 is locked in position when enlarged inner portion 263 is received in detents 265, and to move delivery shaft 134, button 253 is pushed inward and either proximally (to deploy repair device 130D) or distally (to retact repair device 130D). Detents 265 are positioned so as to correspond respectively with repair device 130D being fully retracted within delivery shaft 134, distal patch 244 being deployed from delivery shaft 134, and struts 252 being deployed from delivery shaft 134. Introducer shaft 268 extends out of the proximal end of delivery shaft 134 and is rotatably mounted to the proximal end of actuator handle 249. A rotatable knob 267 is mounted near the proximal end of introducer shaft 268 and is exposed through a slot 269 in the side of actuator handle 249 to allow rotation of introducer shaft 268 for decoupling from repair device 130D. Retraction wires 270 extend through the interior of introducer shaft 268 and extend out of actuator handle 249 through a hole 271 in the proximal end thereof.

FIGS. 26A and 26B illustrate the deployment of defect repair device 130D of FIGS. 24A–24B. Repair device 130D is delivered through access device 22 (not shown) into the heart in the collapsed configuration of FIG. 25 within delivery shaft 134. In the case of an atrial septal defect, delivery shaft 134 is introduced so that its distal end 136 is on the left atrial side of septum S, as shown in FIG. 26A. Introducer shaft 268 is then advanced distally relative to delivery shaft 134 until patch 244 is deployed from the distal end 136 of the delivery shaft. Upon deployment, distal struts 260 and/or frame 246 (not shown) of patch 244 spring outwardly to an expanded configuration in which patch 244 is generally flat and parallel to septum S within the left atrium. Delivery shaft 134 and introducer shaft 268 are then pulled proximally so that patch 244 engages septum S and points 258 on distal struts 260 penetrate into septum S. Delivery shaft 134 is then pulled further proximally relative to introducer shaft 268 so that struts 252 are deployed from delivery shaft 134, allowing them to spring outwardly and toward septum S, anchoring patch 244 in position as shown in FIG. 26B.

If the position of patch 244 is not satisfactory, retraction wires 270 may be tensioned to retract struts 252 back into delivery shaft 136. Introducer shaft 268 may then be pulled proximally to retract patch 244 back into the delivery shaft, or introducer shaft 268 may be pushed distally to disengage patch 244 from septum S, then manipulated to reposition the patch at the desired location. Struts 252 are then re-deployed in the manner described above. Once patch 244 is positioned satisfactorily on septum S, retraction wires 270 are removed from struts 252, introducer shaft 268 is decoupled from hub 250, and the introducer shaft and delivery shaft 134 are removed from the heart. Access device 22 is then removed from the heart, the penetration in the heart wall is closed, and the procedure completed as described above.

It should be noted that in any of the foregoing embodiments of defect repair device 130, a portion of the patient's own pericardium may be excised and mounted to the frame or struts of the defect repair device as a patch. In an exemplary embodiment, endoscopic scissors and graspers are introduced through access ports 90 and used to cut and remove a portion of pericardium of suitable size to cover the septal defect. Exterior to the chest cavity, the pericardial patch is then sutured onto a wire frame similar to frames 224, 226, 228 of FIGS. 21–23, or onto struts like struts 252, 260 of FIGS. 24–26. If desired, two pericardial patches may be mounted to two frames or two sets of struts interconnected by a hub to provide patches on both sides of the cardiac septum. Once the pericardial patch is attached to the frame or struts, the defect repair device is introduced into the heart through access device 22 and attached to the cardiac septum as described above. Advantageously, the use of the patient's own pericardium reduces the risk of biologic incompatibility and other potential complications of artificial patch materials.

In another embodiment of the invention, illustrated in FIGS. 27–33, an apparatus and method are provided for closure of septal defects using sutures, rather than patch-type defect repair devices. In this embodiment, a plurality of needles 274 are mounted to a distal end 276 of an introducer shaft 278. Needles 274 are held parallel to introducer shaft 278 in a generally circular arrangement coaxial with the introducer shaft. Needles 274 may be between 2 and 12 in number, and preferably are 4, 6, or 8 in number, depending upon the size of the defect to be closed. A length of suture thread 275 (best seen in FIG. 28) extends between each pair of needles 274, each pair having one needle on opposite sides of an imaginary line separating needles 274 into two equal groups.

Figure 27:
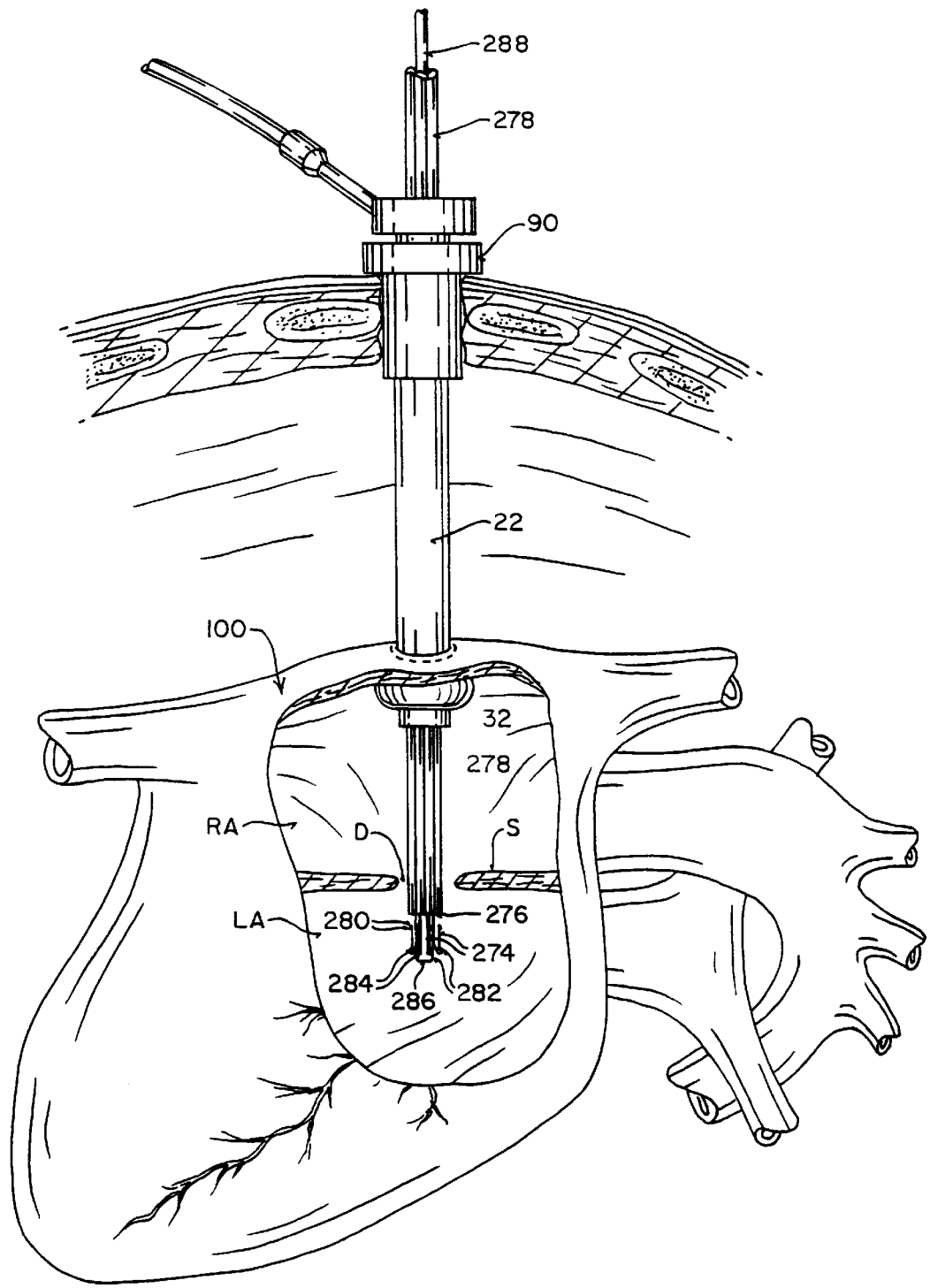
FIGS. 27 is a front cut-away view of a patient's chest showing the introduction of a suturing device into the heart for repairing a septal defect in an alternative embodiment of the method of the invention.

Introducer shaft 278 is preferably a rigid material such as stainless steel for optimum control in manipulating and positioning needles 274 from outside of the chest cavity. Alternatively, all or a distal portion of introducer shaft 278 may be a flexible material and may include means for deflecting or steering distal end 276, such as pull wires anchored internally to distal end 276 and extending through the introducer shaft to an actuator at the proximal end for selectively tensioning the pull wires. Introducer shaft 278 may be used to introduce needles 274 through access device 22 into the right atrium RA, and through septal defect D into left atrium LA, as illustrated in FIG. 27. Needles 274 have sharp distal tips 280 oriented so as to point in a proximal direction toward septum S from left atrium LA, and are held removably at their proximal ends 282 in needle holders 284 extending distally from the distal end of introducer shaft 278. Needle holders 284 comprise flexible rods of stainless steel, titanium, Nitinol® (Raychem Corp.), or a biocompatible polymer, having a needle holding cup 285 (seen more clearly in FIGS. 28–29) at their distal ends in which needles 274 are inserted.

An expandable element 286 is disposed concentrically within the space surrounded by needles 274 distal to introducer shaft 278. Expandable element 286 may comprise an inflatable balloon having an interior in communication with an inflation tube 288 extending through an inner lumen in introducer shaft 278. Alternatively, expandable element 286 may comprise a rigid camming element such as a disk, cylinder, or ball fixed to the end of a movable shaft 288.

Figure 28:
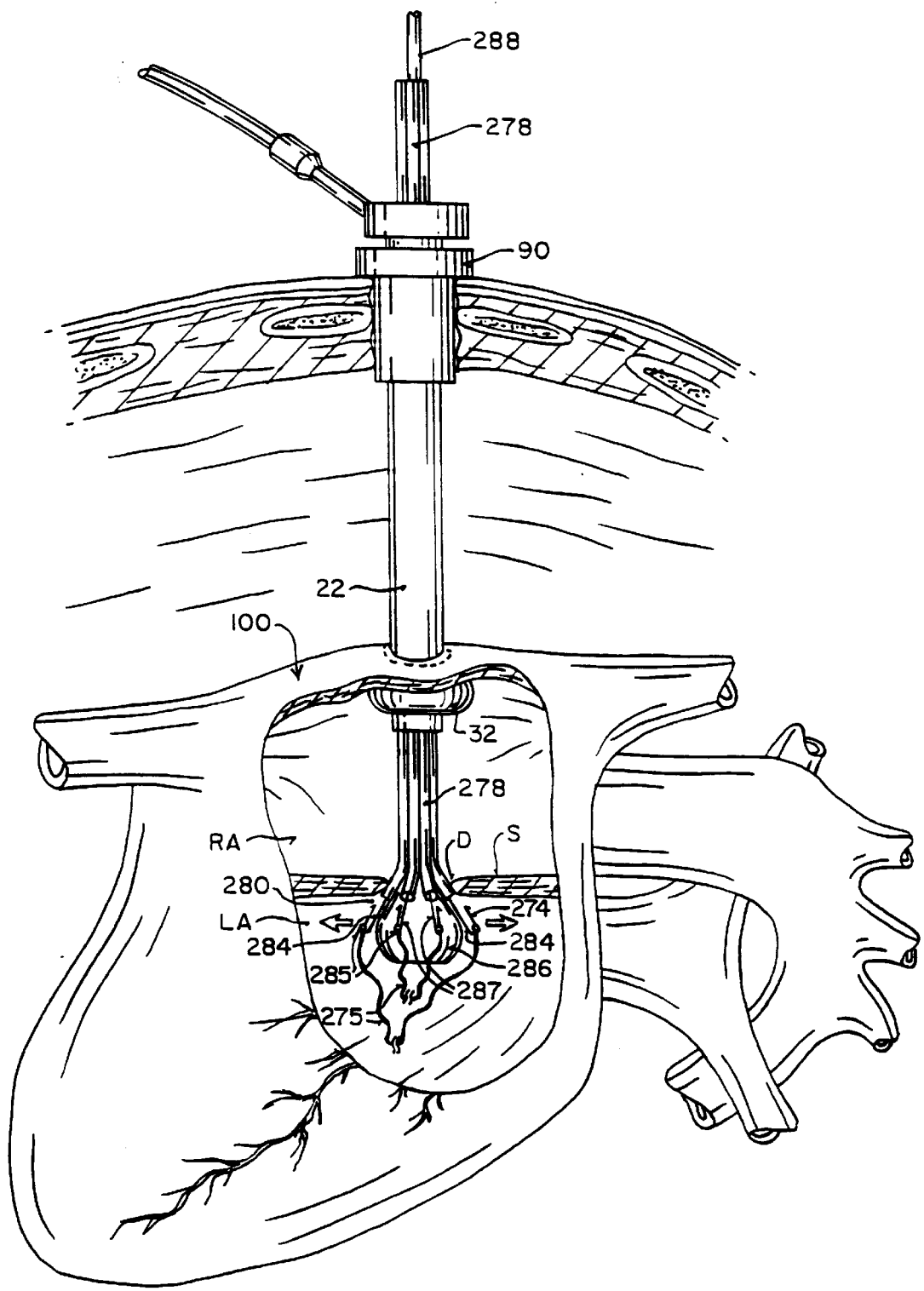
FIG. 28 is a front cut-away view of a patient's chest showing the expansion of a plurality of needles at the distal end of the suturing device according to the method of the invention.

As illustrated in FIG. 28, expandable element 286 is expanded by, e.g., introducing an inflation fluid through inflation tube 288. Expandable member 286 urges needle holders 284 outward so that distal tips 280 are pointed toward septum S around the periphery of defect D.

Figure 29A:
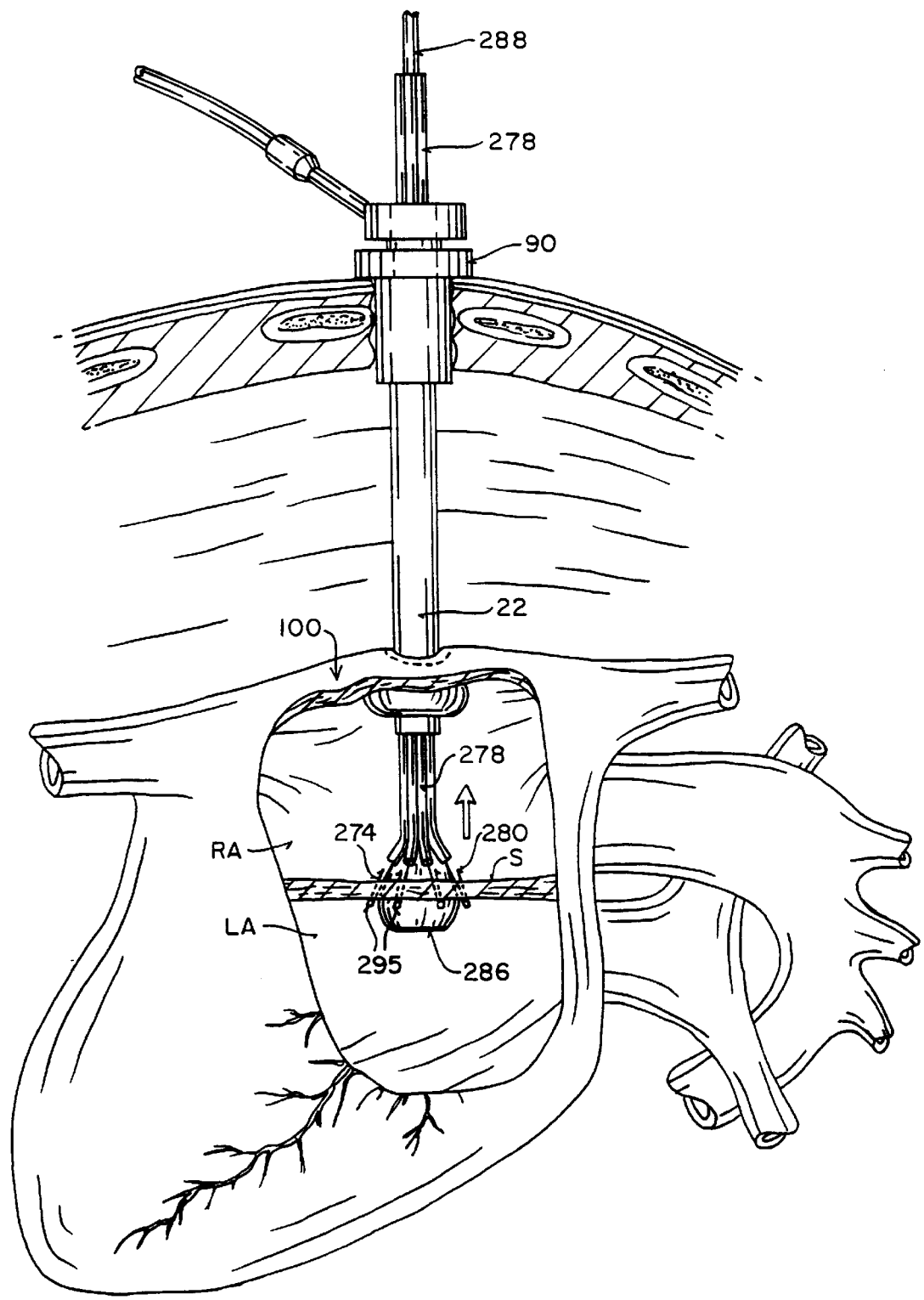
FIG. 29A is a front cut-away view of a patient's chest showing drawing the plurality of needles through the cardiac septum according to the method of the invention.
Figure 29B:
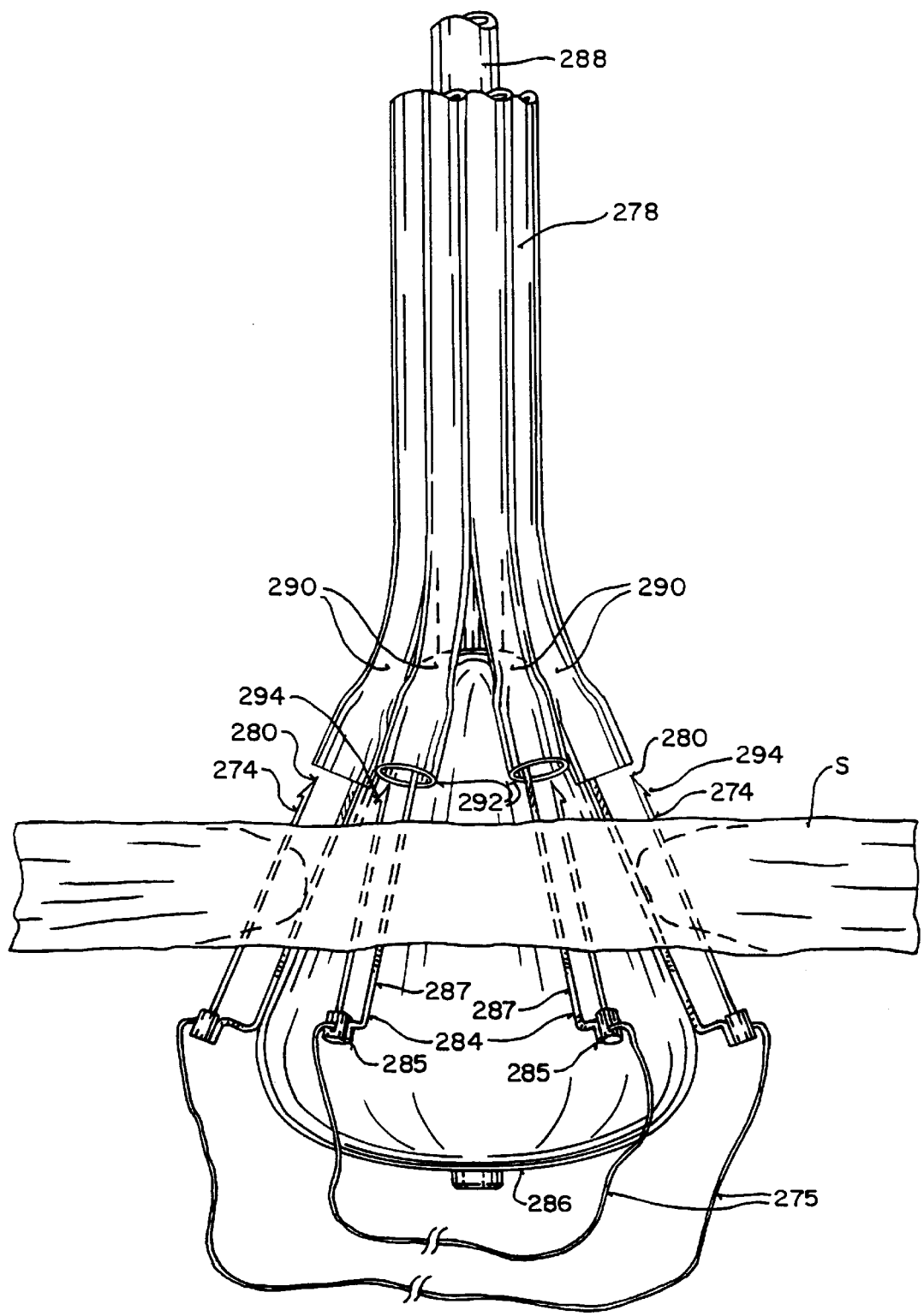
FIG. 29B is a side view of the cardiac septum in the patient's chest of FIG. 29A showing the position of the needles through the cardiac septum according to the method of the invention.

With needle holders 284 in a radially-expanded position, introducer shaft 278 is drawn proximally relative to access device 22 so that needle distal tips 280 penetrate septum S, as shown in FIGS. 29A–29B. It can be seen that cups 285 on needle holder 284 are held in an offset relationship to flexible rods 287 so that when rods 285 engage septum S at the periphery of defect D, needles 274 are spaced outwardly a predetermined distance from the edge of the defect to ensure adequate spacing and "bite" on the septal tissue. Preferably, each needle 274 penetrates septum S about 1–3 mm from the edge of defect D.

As best seen in FIG. 29B, introducer shaft 278 may comprise a plurality of axial tubes 290 in which needle holders 284 are disposed. Needle holders 284 are slidable within tubes 290 so that needles 274 may be moved proximally relative to tubes 290 until distal tips 280 enter the open distal ends 292 of tubes 290. A distal portion of tubes 290 may be flared or widened to facilitate receiving needles 274. A means for capturing needles 274 (not shown) is provided within tubes 290 near distal ends 292, such as a porous mesh or screen of a biocompatible material such as Gore-Tex®, cotton, or Dacron, which may be penetrated by distal tips 280 of needles 274. A barb 294 is provided on needles 274 just proximal to distal tips 280 which may be caught in the needle capturing means within tubes 290 to retain needles 274 therein. Once needles 274 are captured within tubes 290, introducer shaft 278 is drawn proximally relative to needle holders 284, pulling needles 274 through septum S. Expandable member 286 may then be deflated, and expandable member 286 along with needle holders 284 are then pulled proximally through defect D. Introducer shaft 278 (to which needles 274 are attached at distal ends 290), introducer shaft 278, and inflation tube 288 are then withdrawn from the heart through access device 22.

Figure 30A:
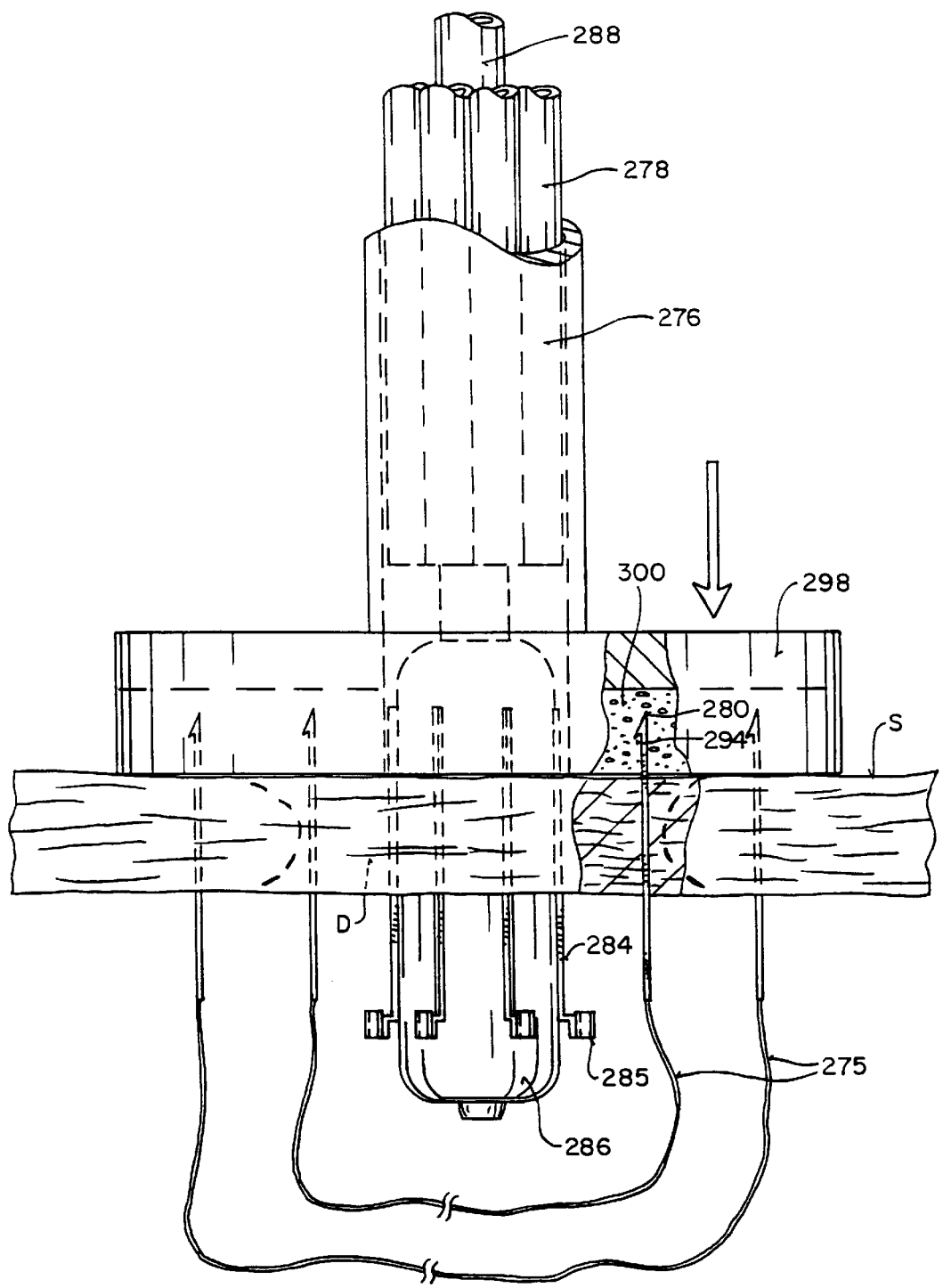
FIG. 30A is a side view of the cardiac septum of FIG. 29B showing capturing the needles in a capture disk according to the method of the invention.

In an alternative embodiment, illustrated in FIGS. 30A–30B, the means for capturing needles 290 comprises an outer sleeve 296 slidably disposed over introducer shaft 278. Outer sleeve 296 has a capture disk 298 on its distal end which has a penetrable outer layer 300 comprising a porous mesh, sponge, or screen of a biocompatible material such as Gore-Tex®, cotton, or Dacron. To capture needles 274, as shown in FIG. 30A, expandable member 286 is deflated, and outer sleeve 296 is slid distally over introducer shaft 278 until distal tips 280 of needles 274 penetrate outer layer 300 of capture disk 298. Barbs 294 are caught in the porous material of outer layer 300. Outer sleeve 296 may then be drawn proximally relative to introducer shaft 278 as shown in FIG. 30B, pulling needles 274 through septum S. Expandable member 286 and needle holders 284 are then withdrawn through defect D. Outer sleeve 296 (to which needles 274 are attached), introducer shaft 278, and inflation tube 288 are then withdrawn from the heart through access device 22.

Capture disk 298 may be a flexible foam or solid material such as natural or synthetic rubber (e.g. silicone), thermoplastic elastomer, or polyurethane so as to be collapsible for introduction and removal from the heart through access device 22. Alternatively, capture disk 298 may be an expandable member such as an inflatable balloon or expandable basket which allows introduction and removal through access device 22 in a collapsed state, and expansion into an expanded state within the heart for capturing needles 274. In either case, capture disk 298 has sufficient rigidity when expanded to allow needles 274 to penetrate outer layer 300 without the capture disk over-flexing or collapsing.

As a further alternative technique for capturing needles 274 after they have penetrated septum S, needles 274 are removed from cups 285 by pushing distally on needle holders 284. Expandable member 286 is then deflated and withdrawn through defect D along with needle holders 284. Introducer shaft 278, inflation tube 288 and needle holders 284 are then withdrawn from the heart through access device 22, leaving needles 274 extending through septum S. An elongated endoscopic needle driver (not shown) may then be introduced through access device 22 into the heart, and, under visualization with ultrasound, an endoscope, or fluoroscope, the needle driver is used to grasp each needle 274 and pull it through septum S and out of the heart through access device 22.

Figure 31B:
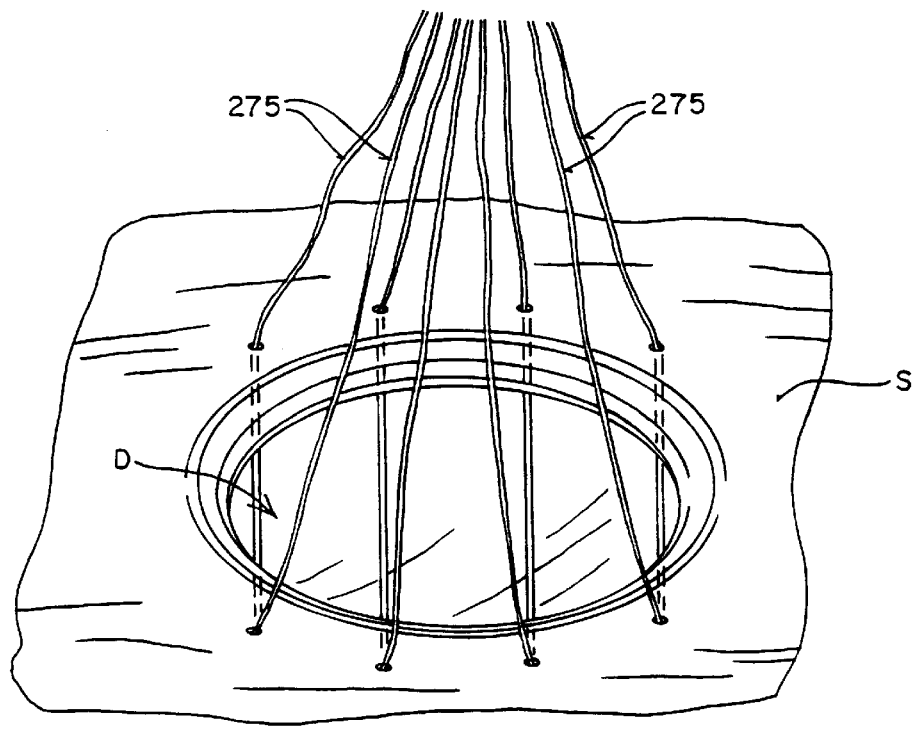
FIGS. 31B–31C are perspective views of the cardiac septum of FIG. 31A showing tensioning and tying the sutures to close the septal defect according to the method of the invention.
Figure 31C:
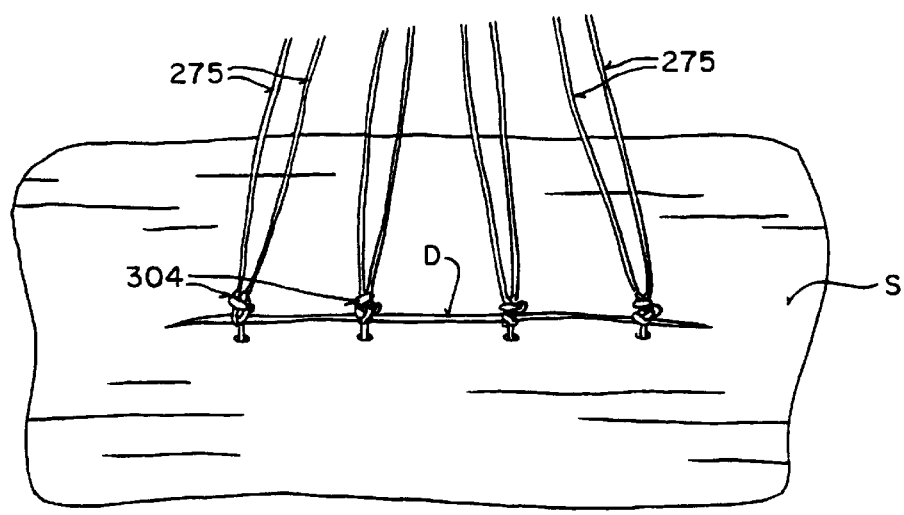

When needles 274 have been withdrawn from the heart, at least one, and usually two to six loops of suture (depending upon the number of needle pairs used), will have been formed across defect D, as illustrated in FIG. 31A–31B. Suture threads 275 are long enough, usually at least about 30 cm in length, to extend across defect D and through septum S, with both ends extending out of the heart and chest cavity through access device 22. In this way, sutures 275 may be tensioned to draw defect D closed, and knots formed extracorporeally and pushed into the heart through access device 22 using an elongated endoscopic knot pusher. As shown in FIG. 31C, a plurality of knots 304 are formed in each suture 275 and pushed against septum S to ensure tight closure of defect D. Sutures 275 are then trimmed using elongated endoscopic scissors introduced through access device 22. Complete closure and absence of shunting is verified using transesophageal echocardiography or one of the other visualization techniques outlined above.

Figure 32A:
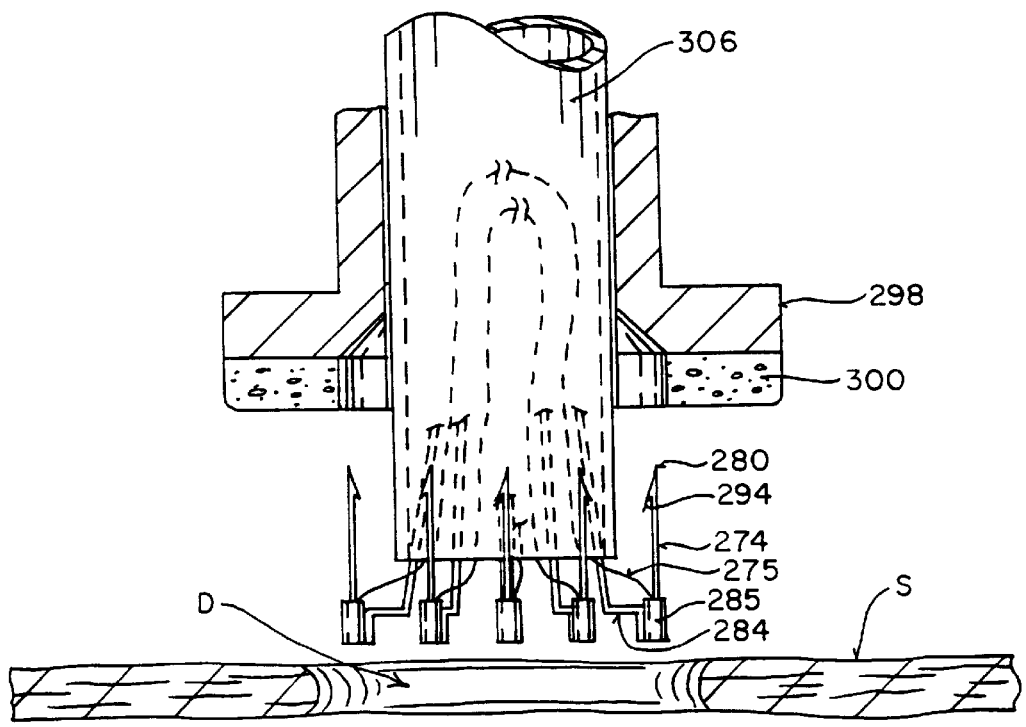
FIGS. 32A–32D are side views of an alternative embodiment of a suture-type septal defect repair device according to the invention, showing the deployment of the needles in the cardiac septum and the capture of the needles according to the method of the invention.
Figure 32B:
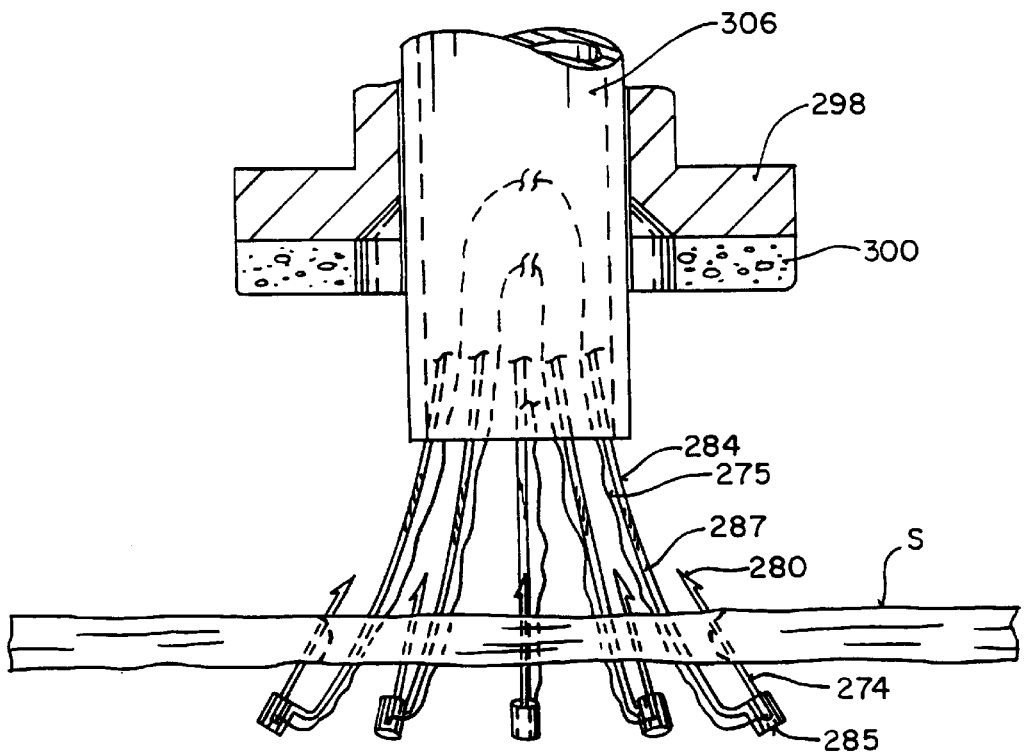

An alternative embodiment of a septal defect repair device according to the invention is illustrated in FIGS. 32A–32D. This embodiment of defect repair device 130 is in many respects similar to that described above in connection with FIGS. 27–30, the major difference being that needle holders 284 are pre-shaped so as to be biased outward into the radially-expanded configuration shown in FIG. 32B. Needle holders 284 may be stainless steel, a shape-memory alloy such as nickel-titanium, or another flexible and resilient metal or polymer. Needle holders 284 may be long enough to extend entirely out of the body cavity through access device 22, or they may be attached to an introducer shaft (not shown) as in the above embodiments. As shown in FIG. 32A, a restraining sleeve 306 is slidably positioned over needle holders 284 and may be advanced distally relative to the needle holders to urge needle holders 284 inward into a collapsed position for introduction through access device 22 and through defect D. A distal portion of needle holders 284 is pre-shaped in an outward bend or curve so that, when restraining sleeve 306 is retracted, needle holders 284 return to a radially-expanded position in which needles 274 are positioned outside of a circle defined by the diameter of defect D. As in previous embodiments, needle holding cups 285 are offset relative to rods 287 of needle holders 284 so that needle holders 284 move outward until rods 287 engage septum S at the periphery of defect D. Needles 274 are then positioned at a predetermined spacing from the edge of defect D to ensure adequate "bite" into septal tissue.

Figure 32C:
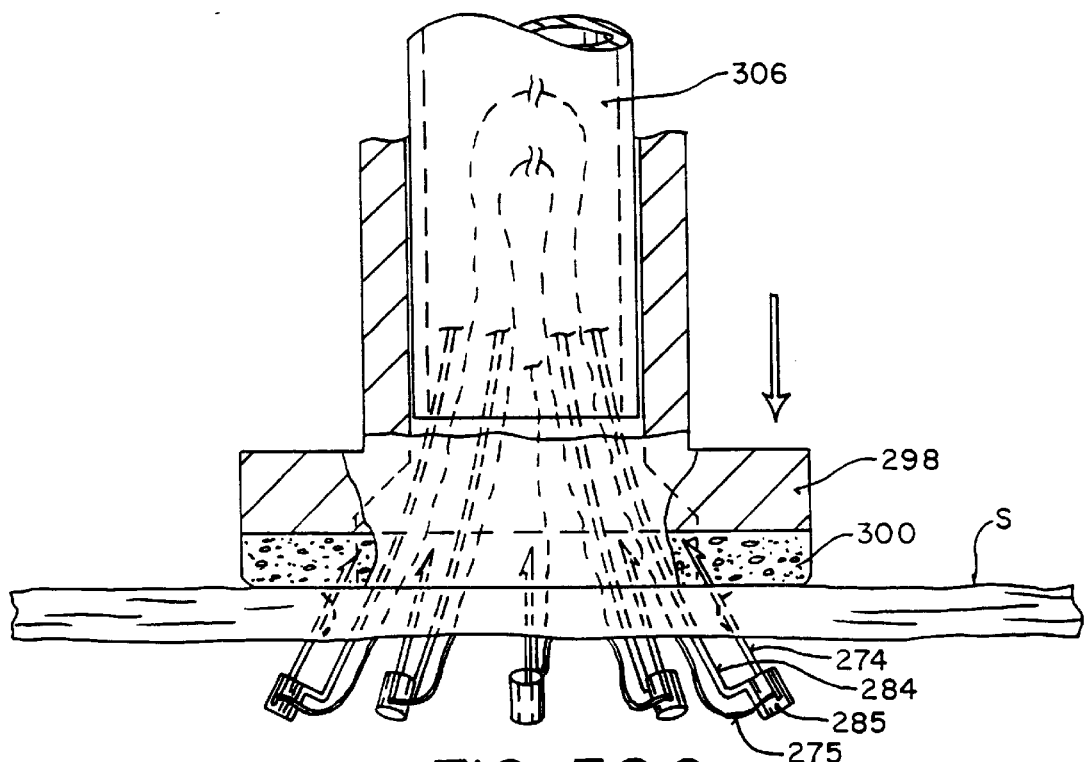
Figure 32D:
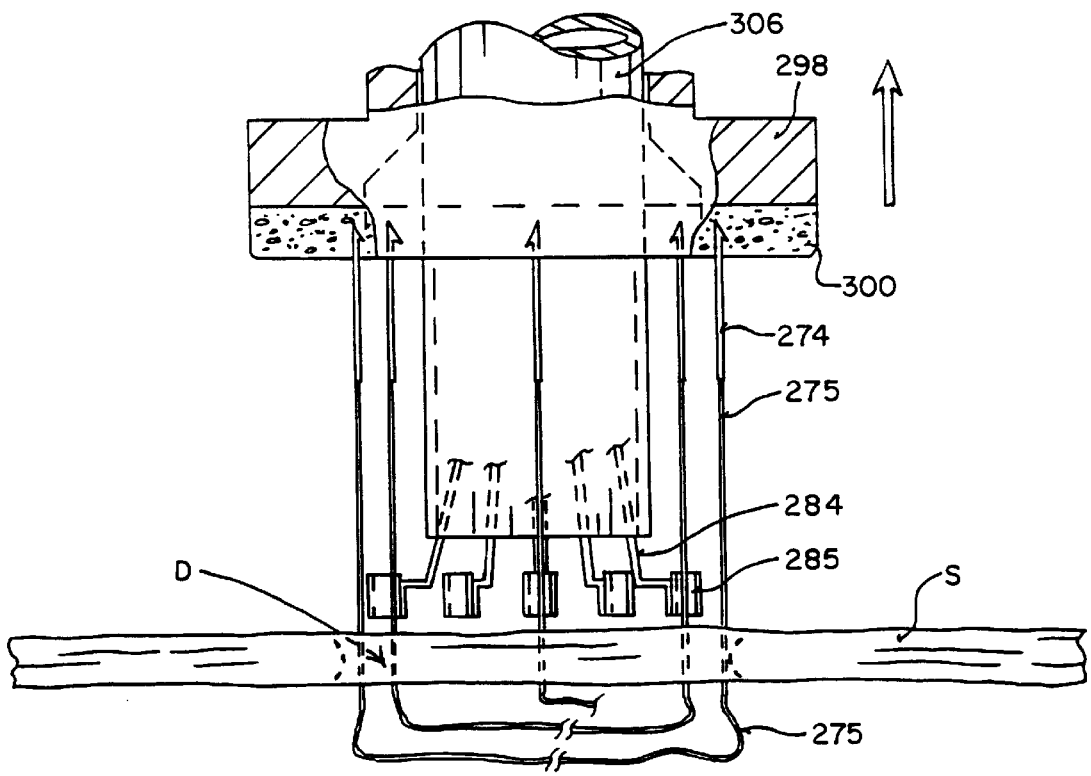

The embodiment of the defect repair device of FIGS. 32A–32D is otherwise similar to the embodiments of FIGS. 27–31 described above. As shown in FIGS. 32C–32D, after needles 274 have been drawn through septum S around defect D, the needles are captured by means of a capture disk 298 with a porous outer layer 300, or by another means such as endoscopic needle drivers introduced through access device 22, as described above. After capture of needles 274, restraining sleeve 306 is advanced distally to collapse needle holders 284 inward, and needle holders 284, restraining sleeve 306, capture disk 298, and needles 274 are withdrawn from the heart through access device 22. This leaves sutures 275 extending across defect D as shown in FIGS. 31A–31B; sutures 275 are then tensioned, knots are formed in sutures 275 extracorporeally, and the knots are pushed into the heart and against septum S using an endoscopic knot pusher, closing defect D as illustrated in FIG. 31C. A suitable knot pusher is disclosed in copending application Ser. No. 08/288,674, entitled "Surgical Knot Pusher and Method of Use," filed Aug. 10, 1994, now U.S. Pat. No. 5,601,576 the disclosure of which is hereby incorporated herein by reference.

It should be noted that while the method of the invention has been described in connection with the repair of atrial septal defects, it will be understood to those of ordinary skill in the art that the invention will be equally applicable to repair of ventricular septal defects, patent ductus arteriosus, and other defects of the heart. Access device 22 may also be introduced through a wall of the right ventricle, left atrium, pulmonary artery, or pulmonary vein rather than the right atrium. Alternatively, access device 22 may be introduced into the right atrium as previously described, with access to the right ventricle or pulmonary artery obtained from the right atrium through the tricuspid valve. Devices and techniques similar to those described above for atrial septal defects may be used for repairing ventricular defects and patent ductus arteriosus. Other repair devices designed specifically for ventricular septal defects and patent ductus arteriosus which are useful in the method of the present invention are described in U.S. Pat. No. 3,874,388, which has been incorporated herein by reference. The defect repair devices of the invention may also be used to repair the penetration in the heart wall made by access device 22, and to repair other types of defects, holes, incisions, or punctures in other organs and tissue structures.

Figure 33:
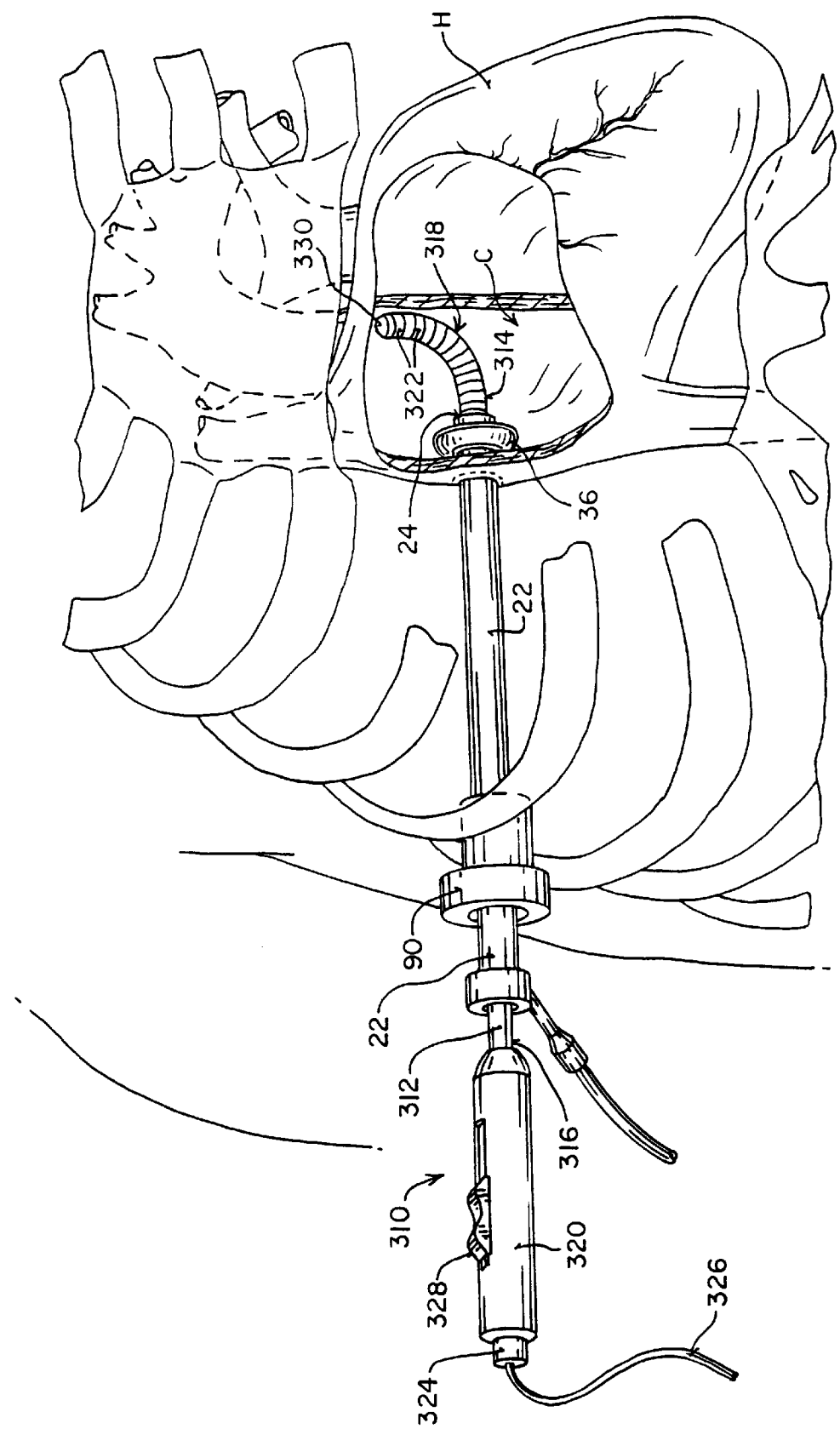
FIG. 33 is a front cut-away view of a patient's chest showing an electrophysiology device according to the invention positioned through the access device of FIG. 1 in a method of electrophysiological treatment according to the invention.
Figure 34:
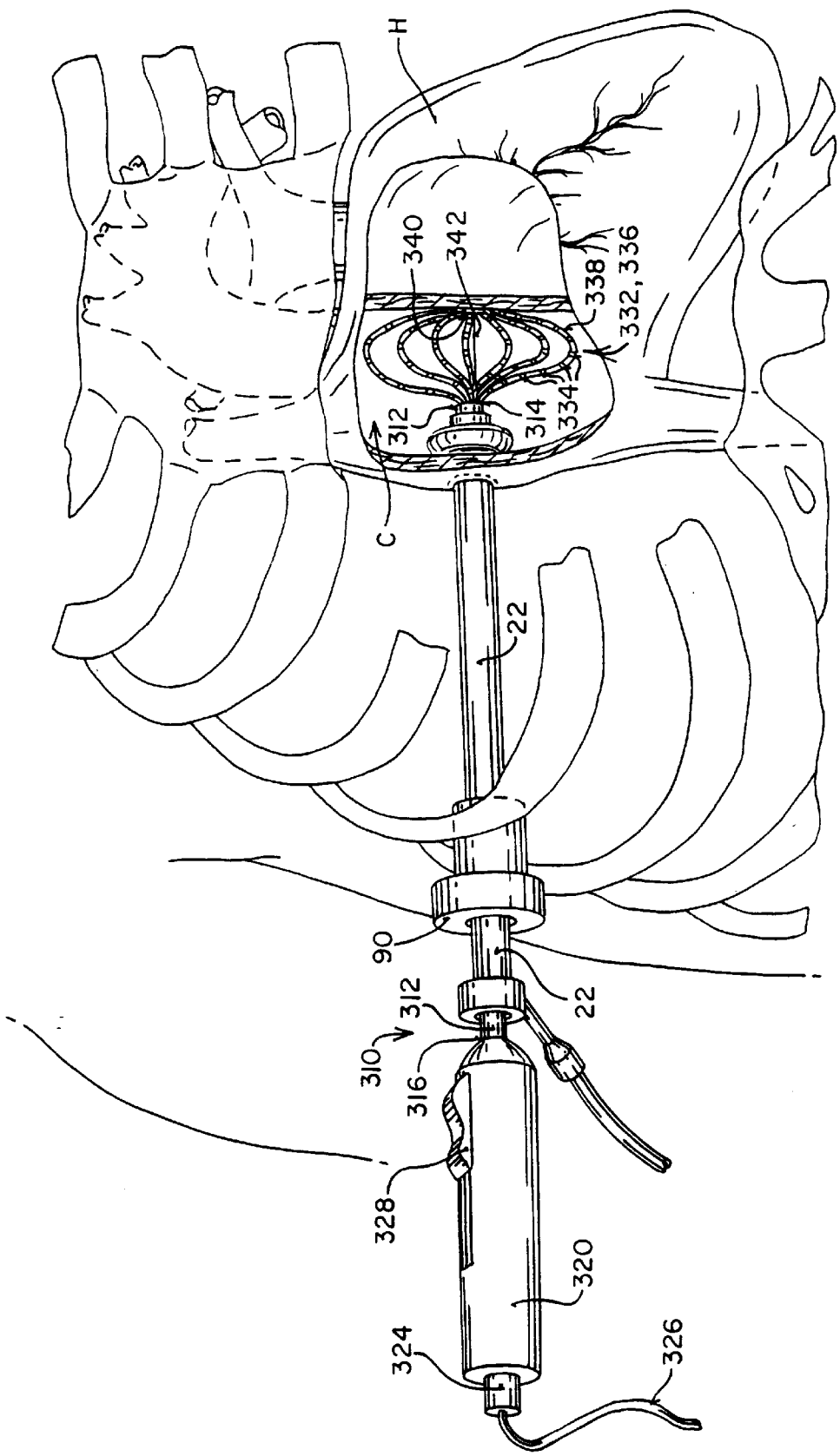
FIG. 34 is a front cut-away view of a patient's chest showing an alternative embodiment of an electrophysiology device according to the invention positioned through the access device of FIG. 1 in a method of electrophysiological treatment according to the invention.

In addition to repair of atrial and ventricular septal defects and patent ductus arteriosus, the devices and methods of the invention also facilitate various other intracardiac interventions, including electrophysiological mapping and ablation. FIGS. 33 and 34 illustrate two embodiments of an electrophysiological device according to the invention. In the embodiment of FIG. 33, an electrophysiology device 310 is introduced through access device 22 into a chamber C of the heart H. Electrophysiology device 310 includes a rigid shaft 312 having a distal end 314 and a proximal end 316. Usually, at least one inner lumen (not shown in FIG. 33) extends through shaft 312 between distal end 314 and proximal end 316. A flexible and pre-shaped or deflectable tip 318 is attached to distal end 314. A handle 320 is attached to proximal end 316. A plurality of conductive electrode bands 322 are mounted to deflectable tip 318, each electrode band being separately electrically coupled by means of wires (not shown) within shaft 312 to a connector 324 on handle 320. Connector 324 is adapted to be coupled to a cord 326 which is connected to a radiofrequency generator or electrocardiography machine (not shown) used in conventional mapping and ablation procedures. An actuator 328 is slidably coupled to handle 320 and is connected to deflectable tip 318 by at least one pull wire (not shown) extending slidably through an inner lumen in shaft 312 and attached internally to deflectable tip 318 near its distal end 330. In this way, sliding actuator 328 proximally on handle 320 deflects deflectable tip 318 into a curved configuration, as illustrated in FIG. 33. Of course, various types of actuators may be used for deflection of deflectable tip 318, including shapable or deflectable handles, joy-sticks, levers, pistol grips, and the like. In addition, shaft 312 may be rotatably coupled to handle 320, and a rotator knob (not shown) may be attached to shaft 312 near proximal end 316 to allow deflectable tip 318 to be rotated about the longitudinal axis of shaft 312. Exemplary mechanisms for actuation and deflection of deflectable tip 318 and other features which may be incorporated into electrophysiology device 310 are disclosed in U.S. Pat. Nos. 4,960,134, 5,318,525, 5,368,592, 5,364,351, and 5,313,943, which are incorporated herein by reference. While these patents disclose highly flexible, endovascular electrophysiology catheters for introduction transluminally from a peripheral vessel into the heart, it will be understood to those of ordinary skill in the art that any of the features of endovascular electrophysiology devices may be easily incorporated into the more rigid, thoracoscopic electrophysiology device of the invention.

Shaft 312 has a length which is long enough to extend from within chamber C of heart H through access device 22 outside of the patient, usually being 20–30 cm in length. Shaft 312 is preferably rigid, usually being made of stainless steel (with insulated electrodes and wires) or of a rigid biocompatible polymer, so as to facilitate precise and controllable positioning of deflectable tip 318 from outside of the chest cavity using handle 320. Deflectable tip 318 is a non-conductive, flexible and biocompatible polymer such as polyurethane, silicone, thermoplastic elastomer, polyolefin, polyamide, or a fluoropolymer.

In an alternative embodiment, illustrated in FIG. 34, electrophysiology device 310 includes, rather than a deflectable tip 318 as in the previous embodiment, an expandable electrode array 332 attached to distal end 314 of shaft 312. In a preferred embodiment, electrode array 332 comprises a plurality of electrode bands 334 mounted in spaced-apart positions to an expandable basket 336. Expandable basket 336 includes a plurality of axially-oriented beams 338, which are preferably a non-conductive, flexible and resilient polymer such as a polyolefin or polyamide, or a metal such as stainless steel or nickel-titanium alloy with an insulative coating to electrically isolate each of electrode bands 334. Beams 338 are coupled together at their distal ends 340, and at their proximal ends are attached to shaft 312. In one embodiment, shaft 312 is a polymeric tubular extrusion, and beams 338 are formed integrally with shaft 312 as part of the same extrusion, by, for example cutting axial slits in a distal portion of shaft 312. As in the embodiment of FIG. 33, each of electrode bands 334 is independently electrically coupled to connector 324 by a wire extending through an inner lumen in shaft 312.

Expandable basket 336 is movable between a collapsed configuration suitable for introduction through access device 22 and an expanded configuration in which electrode bands 334 are spread apart into a three-dimensional array, positioned at various distances both radially outward from and distal to shaft 312, as shown in FIG. 34. In this way, electrode bands 334 may be simultaneously positioned at a number of locations around the interior wall of chamber C. To move expandable basket 336 between the collapsed and expanded configurations, a variety of different mechanisms may be utilized. In one embodiment, a pull wire 342 is coupled to distal ends 340 of beams 338, and extends slidably through a lumen in shaft 312 for attachment to actuator 328. In this way, actuator 328 may be slid in a proximal direction to exert a compressive force on beams 338, causing beams 338 to bow outward into the expanded configuration. When pressure is released from actuator 328, beams 338 recoil to their unstressed, straight configuration.

In addition to the embodiment illustrated, various types of structures may be used for electrode array 332, including those disclosed in U.S. Pat. Nos. 4,699,147, 4,660,571, 4,628,937, 4,522,212, 5,313,943, and 5,327,889, which are incorporated herein by reference. Although these patents describe endovascular electrophysiological catheters, it will be understood to those of ordinary skill in the art that the electrode array configurations, structures and deployment mechanisms disclosed may be easily adapted to the larger diameter, shorter and more rigid thoracoscopic electrophysiology device of the present invention.

Electrophysiology device 310 may be used for either mapping or ablation of conduction pathways in the heart. In use, electrophysiology device 310 is introduced into chamber C of heart H through inner lumen 30 of access device 22. Chamber C may be the left or right ventricle, or left or right atrium, depending upon where the target site for mapping or ablation is located. If the target site is in the higher pressure left side of the heart, access device 22 is provided with a hemostasis seal in inner lumen 30 to allow introduction of electrophysiology device 310 without significant leakage of blood. For the device of FIG. 33, deflectable tip 318 is substantially straight and undeflected during introduction. For the device of FIG. 34, expandable basket 336 is in a collapsed state in which beams 338 are substantially straight and aligned with shaft 312 during introduction. Once introduced into chamber C, deflectable tip 318 is deflected (in the embodiment of FIG. 33) or expandable basket 336 is expanded into an expanded configuration (in the embodiment of FIG. 34) by sliding actuator 328 on handle 320. Under visualization using transesophageal echocardiography or one of the other techniques described above, electrodes 322, 334 are positioned at the desired location against the wall of chamber C by manipulating the device with handle 320. The relatively short distance between the user and the interior of chamber C, as well as the rigidity of shaft 312, facilitate exceptionally controllable and precise manipulation of the device relative to endovascular catheter-based electrophysiology devices.

When electrodes 322, 334 have been positioned at the desired site in chamber C, conduction pathways can be mapped by measuring the electrical potential between selected electrodes with sensitive electrocardiographic equipment. When aberrant pathways are found, they may be ablated by applying radiofrequency current from a radiofrequency generator through a selected electrode or electrodes on electrophysiology device 310 to the myocardial tissue. These techniques may be used to diagnose and/or treat ventricular tachycardias, ventricular fibrillation, supraventricular tachycardias such as Wolff-Parkinson-White Syndrome, atrial fibrillation, and other conduction-related diseases. Ablation may also be performed using a medical laser transmitted through an optical fiber introduced into the heart through access device 22, by techniques analogous to the endovascular laser ablation techniques disclosed in U.S. Pat. No. 5,104,393, which is incorporated herein by reference.

In addition, thoracoscopic, endovascular, or open surgical devices and techniques may be used in conjunction with the devices and methods of the present invention. For example, electrophysiology device 310 may be used to ablate selected cardiac tissue within the heart based on mapping information generated using endovascular mapping catheters or thoracoscopic mapping devices. Alternatively, electrophysiology device 310 may be used for mapping conduction pathways in the heart, which are then treated by means of thoracoscopic, endovascular, or open-chest techniques. Such a technique could be used for treatment of ventricular and supraventricular tachycardias. Similarly, to treat atrial fibrillation, after intracardiac mapping has been performed using the electrophysiology device of the invention and/or endovascular mapping techniques, mechanical, laser, or RF cutting devices may be introduced through access device 22, and precise incisions or ablation lines may be made in the myocardium to create a directed conduction pathway between the sinoatrial node and the atrioventricular node to perform a Cox "maze" procedure.

After the electrophysiology procedure is completed, deflectable tip 318 is returned to its straightened configuration or expandable basket 336 is collapsed so that beams 338 are again straight and aligned with shaft 312. Electrophysiology device 310 is then removed from the chest cavity through access device 22.

In addition to repair of atrial and ventricular septal defects and cardiac mapping and ablation, the devices and techniques of the invention are useful in a variety of other intracardiac procedures. Low-profile, elongated instruments may be introduced through access device 22 to inspect and repair the mitral, tricuspid, pulmonary or aortic valves. Commissurotomy may be performed, for example, by introducing a cutting instrument and incising the valve commissures to separate the valve leaflets. Transmyocardial laser revascularization may be performed by introducing a laser-transmitting optical fiber through access device 22 and using the laser to drill new blood-carrying conduits into the myocardium from within the heart chambers. Cutters, graspers, biters, and the like may be introduced through access device 22 to cut and remove unwanted tissue or other material from the heart and great vessels, such as thrombus (e.g. pulmonary thrombectomy), myxomas, neoplasms, vegetations, calcifications, and tissues affected by hypertrophic obstructive cardiopmyopathy. Catheters may also be introduced through access device 22 for positioning in the pulmonary artery, coronary sinus, or other locations for perfusion, drug delivery, fluid venting, and other purposes. Advantageously, many of these procedures can be performed while the heart is beating, without the need to place the patient on cardiopulmonary bypass and to induce cardioplegic arrest. In addition, these procedures can be performed without the need for a median sternotomy or other gross thoracotomy, reducing greatly the pain, recovery time, morbidity, and mortality associated with open heart surgery.

While the above is a complete description of the preferred embodiments of the invention, it will be understood to one of ordinary skill in the art that certain modifications, substitutions, improvements and additions may be made without departing from the scope thereof, which is defined by the appended claims.

What is claimed is:

1. A method of performing an electrophysiological ablating procedure to ablate cardiac tissue in an interior chamber of a patient's heart, the method comprising steps of:

forming a first opening in a patient's chest, the first opening passing through the chest wall and into the patient's thoracic cavity;

forming a second opening in the wall of the patient's heart, the second opening passing through the wall of the heart and into an interior chamber of the heart;

providing a cardiac access device having a distal end and a lumen for receiving an electrophysiological instrument;

positioning at least the distal end of the cardiac access device through the first and second openings and into the interior chamber of the heart;

providing an electrophysiological ablating instrument comprising at least one electrode configured to deliver electrical current, the electrode being coupled to a source of electrical current;

positioning the electrophysiological ablating instrument in the lumen of the cardiac access device so that at least the electrode extends out of the distal end of the cardiac access device; and contacting cardiac tissue with the electrode and delivering current to the tissue to ablate at least selected portions of the tissue.

2. The method of 1, wherein the electrode of the electrophysiological ablating instrument is coupled to a source of radiofrequency current, and the radiofrequency current is delivered to the cardiac tissue through the electrode.

3. The method of claim 1, wherein the electrophysiological ablating instrument comprises a plurality of electrodes which contact and deliver current to the cardiac tissue.

4. The method of claim 1, wherein the first opening is formed in the chest wall so as to pass through an intercostal space between adjacent ribs, and the cardiac access device is positioned through the intercostal space and through the second opening in the wall of the heart.

5. The method of claim 4, wherein the patient's ribs and sternum remain substantially intact during each of said steps.

6. The method of claim 1, wherein said steps are carried out while the patient's heart is beating, and further comprising the step of forming a hemostatic seal between the cardiac access device and the wall of the heart to inhibit blood loss through the second opening.

7. The method of claim 1, further comprising the step of deflecting a distal end of the electrophysiological instrument to position the electrode adjacent an interior wall of the heart.

8. A method of performing an electrophysiological mapping procedure in an interior chamber of a patient's heart, the method comprising steps of:

forming a first opening in a patient's chest, the first opening passing through the chest wall and into the patient's thoracic cavity;

forming a second opening in the wall of the patient's heart, the second opening passing through the wall of the heart and into an interior chamber of the heart;

providing a cardiac access device having a distal end and a lumen for receiving an electrophysiological instrument;

positioning at least the distal end of the cardiac access device through the first and second openings and into the interior chamber of the heart;

providing an electrophysiological mapping instrument comprising at least two electrodes configured to contact cardiac tissue, the electrodes being coupled to a device for detecting electrical potential between the electrodes;

positioning the electrophysiological mapping instrument in the lumen of the cardiac access device so that at least the electrodes extend out of the distal end of the cardiac access device; and contacting cardiac tissue with the electrodes on the electrophysiological mapping instrument and detecting the electrical potential between the electrodes to map conduction pathways in the cardiac tissue.

9. The method of claim 8, wherein the first opening is formed in the chest wall so as to pass through an intercostal space between adjacent ribs, and the cardiac access device is positioned through the intercostal space and through the second opening in the wall of the heart.

10. The method of claim 9, wherein the patient's ribs and sternum remain substantially intact during each of said steps.

11. The method of claim 8, wherein said steps are carried out while the patient's heart is beating, and further comprising the step of forming a hemostatic seal between the cardiac access device and the wall of the heart to inhibit blood loss through the second opening.

12. The method of claim 8, wherein the contacting step is carried out by moving the electrodes from a first position in which they are out of contact with the cardiac tissue to a second position in which they are in contact with the cardiac tissue.

13. The method of claim 12, wherein the electrophysiological instrument comprises an expandable mechanism supporting the electrodes, and the expandable mechanism is moved from a collapsed orientation to an expanded orientation to move the electrodes from the first position to the second position and into contact with the cardiac tissue.

14. The method of claim 8, further comprising, after said contacting step, steps of:

providing an electrophysiological ablating instrument comprising at least one electrode configured to deliver electrical current, the electrode being coupled to a source of electrical current;

positioning the electrophysiological ablating instrument in the lumen of the cardiac access device so that at least the electrode extends out of the distal end of the cardiac access device; and contacting cardiac tissue with the electrode and delivering current to the tissue to ablate at least selected portions of the tissue.

* * * * *